US011008580B2

(12) United States Patent
Allen et al.

(10) Patent No.: US 11,008,580 B2
(45) Date of Patent: *May 18, 2021

(54) REGULATION OF GENE EXPRESSION BY TEMPORAL OR LEAF SPECIFIC PROMOTERS

(71) Applicant: MONSANTO TECHNOLOGY LLC, St. Louis, MO (US)

(72) Inventors: Edwards M. Allen, O'Fallon, MO (US); Sara E. Heisel, Labadie, MO (US); Sergey Ivashuta, Ballwin, MO (US); Elysia K. Krieger, Kirkwood, MO (US); Jennifer Lutke, Ballwin, MO (US); Robert J. Meister, St. Peters, MO (US); Yuanji Zhang, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/958,026

(22) Filed: Apr. 20, 2018

(65) Prior Publication Data

US 2018/0237791 A1  Aug. 23, 2018

Related U.S. Application Data

(63) Continuation of application No. 15/065,416, filed on Mar. 9, 2016, now Pat. No. 9,976,152, which is a continuation of application No. 14/191,825, filed on Feb. 27, 2014, now Pat. No. 9,315,819, which is a continuation of application No. 12/665,338, filed as application No. PCT/US2008/068276 on Jun. 26, 2008, now Pat. No. 8,697,949, which is a continuation of application No. 11/768,264, filed on Jun. 26, 2007, now Pat. No. 8,314,290.

(51) Int. Cl.
C12N 15/82 (2006.01)

(52) U.S. Cl.
CPC ....... *C12N 15/8218* (2013.01); *C12N 15/827* (2013.01); *C12N 15/8216* (2013.01); *C12N 15/8217* (2013.01); *C12N 15/8225* (2013.01); *C12N 15/8234* (2013.01); *C12N 15/8238* (2013.01); *C12N 15/8254* (2013.01); *C12N 15/8265* (2013.01); *C12N 15/8275* (2013.01); *C12N 15/8279* (2013.01); *C12N 15/8285* (2013.01); *C12N 15/8286* (2013.01); *C12N 15/8289* (2013.01); *Y02A 40/146* (2018.01)

(58) Field of Classification Search
None
See application file for complete search history.

(56) References Cited

U.S. PATENT DOCUMENTS

| | | |
|---|---|---|
| 5,004,863 A | 4/1991 | Umbeck |
| 5,015,580 A | 5/1991 | Christou et al. |
| 5,159,135 A | 10/1992 | Umbeck |
| 5,416,011 A | 5/1995 | Hinchee et al. |
| 5,463,174 A | 10/1995 | Moloney et al. |
| 5,550,365 A | 3/1996 | Fischhoff et al. |
| 5,518,908 A | 5/1996 | Corbin et al. |
| 5,538,880 A | 7/1996 | Lundquist et al. |
| 5,550,318 A | 8/1996 | Adams et al. |
| 5,569,834 A | 10/1996 | Hinchee et al. |
| 5,591,616 A | 1/1997 | Hiei et al. |
| 5,633,435 A | 5/1997 | Barry et al. |
| 5,750,848 A | 5/1998 | Krüger et al. |
| 5,750,871 A | 5/1998 | Moloney et al. |
| 5,763,245 A | 6/1998 | Greenplate et al. |
| 5,780,708 A | 7/1998 | Lundquist et al. |
| 5,824,877 A | 10/1998 | Hinchee et al. |
| 5,837,848 A | 11/1998 | Ely et al. |
| 5,846,797 A | 12/1998 | Strickland |
| 5,888,732 A | 3/1999 | Hartley et al. |
| 5,914,451 A | 6/1999 | Martinell et al. |
| 5,981,840 A | 11/1999 | Zhao et al. |
| 6,084,089 A | 7/2000 | Mine et al. |
| 6,118,047 A | 9/2000 | Anderson et al. |
| 6,140,078 A | 10/2000 | Sanders et al. |
| 6,153,812 A | 11/2000 | Fry et al. |
| 6,160,208 A | 12/2000 | Lundquist et al. |
| 6,194,636 B1 | 2/2001 | McElroy et al. |

(Continued)

FOREIGN PATENT DOCUMENTS

| | | |
|---|---|---|
| WO | WO 1995/06128 | 3/1995 |
| WO | WO 1995/006722 | 3/1995 |

(Continued)

OTHER PUBLICATIONS

Andersen et al, 2019, Genetics, 21:71-87.*
Allen et al., "Evolution of microRNA genes by inverted duplication of target gene sequences in *Arabidopsis thaliana*," *Nature Genetics*, 36:1282-1290 (2004).
Allen et al., "microRNA-Directed Phasing during Trans-Acting siRNA Biogenesis in Plants," *Cell*, 121:207-221(2005).
Altschul et al., "Basic Local Alignment Search Tool," *Journal of Molecular Biology*, 215:403-410 (1990).
Altschul et al., "Gapped BLAST and PSI-BLAST: a new generation of protein database search programs," *Nucleic Acids Research*, 25:3389-3402 (1997).

(Continued)

*Primary Examiner* — Jason Deveau Rosen
(74) *Attorney, Agent, or Firm* — Arnold & Porter Kaye Scholer LLP; Amanda Carmany-Rampey; David R. Marsh

(57) ABSTRACT

This invention provides molecular constructs and methods for the temporally specific control of gene expression in plants or in plant pests or pathogens. More specifically, this invention provides plant miRNA genes having novel circadian expression patterns that are useful for designing recombinant DNA constructs for temporally specific expression of at least one gene. Also provided are non-natural transgenic plant cells, plants, and seeds containing in their genome a recombinant DNA construct of this invention.

13 Claims, 6 Drawing Sheets

Specification includes a Sequence Listing.

(56) References Cited

U.S. PATENT DOCUMENTS

| | | |
|---|---|---|
| 6,207,879 B1 | 3/2001 | McElroy et al. |
| 6,232,526 B1 | 5/2001 | McElroy et al. |
| 6,252,138 B1 | 6/2001 | Karimi et al. |
| 6,277,608 B1 | 8/2001 | Hartley et al. |
| 6,288,312 B1 | 9/2001 | Christou et al. |
| 6,294,714 B1 | 9/2001 | Matsunaga et al. |
| 6,372,965 B1 | 4/2002 | Lightner et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,426,446 B1 | 7/2002 | McElroy et al. |
| 6,426,448 B1 | 7/2002 | Booth, Jr. et al. |
| 6,429,357 B1 | 8/2002 | McElroy et al. |
| 6,433,252 B1 | 8/2002 | Kriz et al. |
| 6,437,217 B1 | 8/2002 | McElroy et al. |
| 6,583,338 B2 | 6/2003 | McElroy et al. |
| 6,624,344 B1 | 9/2003 | Rangan et al. |
| 6,759,575 B2 | 7/2004 | Michiels et al. |
| 6,872,872 B1 | 3/2005 | Lightner et al. |
| 7,002,058 B2 | 2/2006 | Martinell et al. |
| 7,060,876 B2 | 6/2006 | Hiei et al. |
| 7,393,632 B2 | 7/2008 | Cheo et al. |
| 7,414,125 B2 | 8/2008 | Zhu et al. |
| 7,723,568 B2 | 5/2010 | Lutfiyya et al. |
| 8,143,480 B2 | 3/2012 | Axtell et al. |
| 8,314,290 B2 * | 11/2012 | Allen ............... C12N 15/8216 800/278 |
| 2002/0007051 A1 | 2/2002 | Cheo et al. |
| 2002/0133852 A1 | 9/2002 | Hauge et al. |
| 2003/0049612 A1 | 3/2003 | Echt et al. |
| 2003/0005491 A1 | 6/2003 | Hauge et al. |
| 2003/0167537 A1 | 9/2003 | Jiang |
| 2004/0087030 A1 | 5/2004 | Armstrong et al. |
| 2004/0098761 A1 | 5/2004 | Trick et al. |
| 2004/0115642 A1 | 6/2004 | Fu |
| 2004/0123347 A1 | 6/2004 | Hinchey et al. |
| 2004/0126845 A1 | 7/2004 | Eenennaam et al. |
| 2004/0216189 A1 | 10/2004 | Houmard et al. |
| 2004/0244075 A1 | 12/2004 | Cai et al. |
| 2005/0005321 A1 | 1/2005 | Martinell et al. |
| 2005/0120415 A1 | 1/2005 | Aukerman |
| 2005/0144669 A1 | 6/2005 | Reinhart et al. |
| 2006/0021087 A1 | 1/2006 | Baum et al. |
| 2006/0200878 A1 | 9/2006 | Lutfiyya et al. |
| 2007/0011761 A1 | 1/2007 | Thai et al. |
| 2007/0079393 A1 | 4/2007 | McCutchen et al. |

FOREIGN PATENT DOCUMENTS

| | | |
|---|---|---|
| WO | WO 2002/062129 | 8/2002 |
| WO | WO 2002/057471 | 5/2003 |
| WO | WO 2005/007829 A2 | 1/2005 |
| WO | WO 2005/011816 | 11/2005 |
| WO | WO 2005/110068 A8 | 2/2006 |

OTHER PUBLICATIONS

Ambros et al., "A uniform system for microRNA annotation," *RNA Society*, 9:277-279 (2003).
Arteaga-Vazquez et al., "A Family of MicroRNAs Present in Plants and Animals," *Plant Cell*, 18:3355-3369 (2006).
Aslandis et al., "Ligation-independent cloning of PCR products (LIC-PCR)" *Nucleic Acids Research*, 18:6069-6074 (1990).
Bartel D., "MircoRNAs: Genomics, Biogenesis, Mechanism, and Function," *Cell*, 116:281-297 (2004).
Bayer et al., "Programmable ligand-controlled riboregulators of eukaryotic gene expression," *Nature Biotechnology*, 23:337-343 (2005).
Becker et al., "Fertile transgenic wheat from microprojectile bombardment of scutellar tissue," *Plant Journal*, 5:299 (1994).
Boutros et al., "Genome-Wide RNAi Analysis of Growth and Viability in *Drosophilia* Cells," *Science*, 303:832-835 (2004).
Bytebier et al., "T-DNA organization in tumor cultures and transgenic plants of the monocotyledon *Asparagus officinalis*," *Procedures of the National Academy of Sciences USA*, 84:5345 (1987).
Cheng et al., "Production of fertile transgenic peanut (*Arachis hypogaea* L.) plants using *Agrobacterium tumefaciens*," *Plant Cell Reports*, 15:653 (1996).
Davidson et al., "Engineering regulatory RNAs," *Trends in Biotechnology*, 23:109-112 (2005).
De Amicis et al., "Intercodon dinucleotides affect codon choice in plant genes," *Nucleic Acid Research*, 28:3339-3346 (2000).
De Framond et al., "Mini-Ti: A New Vector Strategy for Plant Genetic Engineering," *Biotechnology*, 1:262-269 (1983).
Du et al., "A systemic analysis of the silencing effects of an active siRNA at all single-nucleotide mismatched target sites," *Nucleic Acids Research*, 33:1671-1677 (2005).
Dugas et al., "MicroRNA regulation of gene expression in plants," *Current Opinion in Plant Biology*, 7:512-520 (2004).
Erdmann et al., "The non-coding RNAs as riboregulators," *Nucleic Acids Research*, 29:189-193 (2001).
Gendel, "Sequence Databases for Assessing the Potential Allergenicity of Proteins Used in Transgenic Foods," *Advances in Food Nutrition Research*, 42:63-92 (1998).
Gottesman S., "Micros for microbes: non-coding regulatory RNAs in bacteria," *Trends Genetics*, 21:399-404 (2005).
Griffiths-Jones et al., "Rfam: an RNA family database," *Nucleic Acids Research*, 31:439-441 (2003).
Griffiths-Jones et al. "Rfam: annotating non-coding RNAs in complete genomes," *Nucleic Acids Research*, 33:121-124 (2005).
Hoekema et al., "A binary plant vector strategy based on separation of vir- and T-region of the *Agrobacterium tumefaciens* Ti-plasmid," *Nature*, 303:179 (1983).
Isaacs et al., "Engineered riboregulators enable post-transcriptional control of gene expression," *Nature Biotechnology*, 22:841-847 (2004).
Jones-Rhoades et al., Computational Identification of Plant MicroRNAs and Their Targets, Including (2004) *Mol. Cell*, 14:787-799.
Jones-Rhoades et al., "MicroRNAs and Their Plant Regulatory Roles in Plants," *Annual Review of Plant Biology*, 57:19-53 (2006).
Katoh et al., "Specific residues at every third position of siRNA shape its efficient RNAi activity," *Nucleic Acids Research*, 4:e27 (2007).
Kertbundit et al., "In vivo random β-glucronidase gene fusions in *Arabdopsis thaliana*," *Procedures of the National Academy of Sciences USA*, 5212-5216 (1991).
Kidner et al. , "Spatially restricted microRNA directs leaf polarity through AGRONAUTE1," *Nature*, 428:81-84 (2004).
Kim et al., "Synthetic dsRNA Dicer substrates enhance RNAi potency and efficacy," *Nature Biotechnology*, 6:376-385 (2005).
Llave et al., "Cleavage of Scarecrow-like mRNA Targets Directed by a Class of *Arabidopsis* miRNA," *Science*, 297:2053-2056 (2002).
Lytle et al., *Proceedings of the National Academy of Sciences USA*, 104:9667-9672 (2007).
Mallory et al., "MicroRNA control of PHABULOSA in leaf development: importance of pairing to the microRNA 5' region," *The EMBO Journal*, 23:3356-3364 (2004).
Mandal et al., "Gene Regulation by Riboswitches," *Molecular Cell Biology*, 5:451-463 (2004).
Mandal et al., "Adenine riboswitches and gene activation by disruption of a transcription terminator," *Nature Structure Molecular Cell Biology*, 11:29-35 (2004).
Margulies et al., "Genome sequencing in microfabricated high-density picolitre reactors," *Nature*, 437:376-380 (2005).
Masoud et al., "Constitutive expression of inducible β-1, 3-glucanase in alfalfa reduces disease severity caused by the oomycete pathogen *Phytophthora megasperma* f. sp *medicaginis*, but does not reduce disease severity of chitin-containing fungi," *Transgenic Research*, 5:313 (1996).
Millar, *Journal of Experimental Botany*, 55(395):277-283 (2004).
Millar et al., "The *Arabodopsis* GAMYB-Like Genes, MYB33 and MYB65, are MicroRNA-Regulated Genes That Redundantly Facilitate Anther Development," *Plant Cell*, 17:705-721 (2005).
Murchison et al., "miRNAs on the move: miRNA biogenesis and the RNAi machinery," *Current Opinion Cell Biology*, 16:223-229 (2004).

(56) References Cited

OTHER PUBLICATIONS

Palatnik et al., "Control of leaf morphogenesis by microRNAs," *Nature*, 425:257-263 (2003).
Parizotto et al., "In vivo investigation of the transcription, processing, endonucleolytic activity, and functional relevance of the spatial distribution of a plant miRNA," *Genes Dev.*, 18:2237-2242 (2004).
Radke et al., "Transformation and regeneration of *Brassica rapa* using *Agrobacterium tumefaciens*," *Plant Cell Reports*, 11:499-505 (1992).
Rashtchian et al., "Uracil DNA Glycoslase-Mediated Cloning of Polymerase Chain Reaction-Amplified DNA: Application to Genomic and cDNA Cloning," Analytical Biochemistry, 206:91-97, (1992).
Reinhart et al., "MicroRNAs in plants," *Genes & Development*, 16:1616-1626 (2002).
Reynolds et al., "Rational siRNA design for RNA interference," *Nature Biotechnology*, 22:326-330 (2004).
Rhoades et al., "Prediction of Plant MicroRNA Targets," *Cell*, 110:513-520 (2002) <http://www.cell.com/cell/fulltext/S0092-8674(02)00863-2>.
Rombauts et al. "Computational Approaches to Identify Promoters and cis-Regulatory Elements in Plant Genomes," *Plant Physiology*, 132:1162-1176 (2003).
Schwab et al., "Specific Effects of MicroRNAs on the Plant Transcriptome," *Developmental Cell*, 8:517-527 (2005) < http://www.cell.com/developmental-cell/pdf/S1534-5807(05)00022-5.pdf>.
Steeves et al., "Transgenic soybeans expressing siRNAs specific to a major sperm protein gene suppress *Heterodera glycines* reproduction," *Functional Plant Biology*, 33:991-999 (2006).
Sudarsan et al., "Metabolite-binding RNA domains are present in the genes of eukaryotes," *RNA*, 9:644-647 (2003).
Sun et al., "A Highly Efficient Transformation Protocol for Micro-Tom, a Model Cultivar for Tomato Function Genomics," *Plant Cell Physiology*, 47:426-431 (2006).
Sunkar et al., "Novel and Stress-Regulated MicroRNAs and Other Small RNAs from *Arabidopsis*," *Plant Cell*, 16:2001-2019 (2004).
Tang, G., "siRNA and miRNA: an insight into RISCs," *Trends Biochemical Sciences*, 30:106-14 (2005).
Tomari et al., "MicroRNA Biogenesis: Drosha Can't Cut It without a Partner," *Current Biology*, 15:R61-64 (2005).
Toriyama et al., "Transgenic Rice Plants After Direct Gene Transfer Into Protoplasts," *Bio/Technology*, 6:10 (1988).
Vasil et al., "Herbicide Resistant Fertile Transgenic Wheat Plants Obtained by Microprojectile Bombardment of Regenerable Embryogenic Callus," *Bio/Technology*,10:667 (1992).
Wan et al., "Generation of Large Numbers of Independently Transformed Fertile Barley Plants," *Plant Physiology*, 104:37-48 (1994).
Winkler et al., "Thiamine derivatives bind messenger RNAs directly to regulate bacterial gene expression," *Nature*, 419:952-956 (2002).
Xie et al., "Expression of *Arabidopsis* MIRNA Genes," *Plant Physiology*, 138:2145-2154 (2005).
Zeng et al., "Both natural and designed micro RNAs can inhibit the expression of cognate mRNAs when expressed in human cells," *Molecular Cell*, 9:1327-1333 (2002) < http://www.cell.com/molecular-cell/pdf/S1097-2765(02)00541-5.pdf >.
Zeng et al., "Efficient Processing of Primary microRNA Hairpins by Drosha Requires Flanking Nonstructured RNA Sequences," *Journal of Biological Chemistry*, 280:27595-27603 (2005).
Zhang Y., "miRU: an automated plant miRNA target prediction server," *Nucleic Acids Research*, 33: W701-704 (2005).
Zhang et al., "Transgenic rice plants produced by electroporation-mediated plasmid uptake into protoplasts," *Plant Cell Reports*, 7:379 (1988).

\* cited by examiner

FIGURE 2

Glycine max miRMON1 miRNA precursor (fold-back portion of SEQ ID NO. 7)

```
>MRT3847_253879C.2

94 acaggaucguccugagaccaaaugagcagcuga 126
       |||.|  ||  ||||||| ||  ||||||||||||
   185 uguucccgcuggacucuugucuacucgucgacu 153
```

GSE = one or more gene suppression elements
GEE = one or more gene expression elements

A

B

REGULATION OF GENE EXPRESSION BY TEMPORAL OR LEAF SPECIFIC PROMOTERS

PRIORITY CLAIMS AND REFERENCE TO RELATED APPLICATIONS

This application is a continuation of U.S. patent application Ser. No. 15/065,416, filed Mar. 9, 2016, which is a continuation of U.S. patent application Ser. No. 14/191,825, filed Feb. 27, 2014, which is a continuation of U.S. patent application Ser. No. 12/665,338, filed Apr. 23, 2010, which is a U.S. National Stage of International Application No. PCT/US2008/068276, filed Jun. 26, 2008, which is a continuation of U.S. patent application Ser. No. 11/768,264, filed Jun. 26, 2007, all of which are incorporated by reference in their entirety herein.

INCORPORATION OF SEQUENCE LISTINGS

A computer readable form of a sequence listing is filed with this application by electronic submission and is incorporated into this application by reference in its entirety. The sequence listing is contained in the file named P34148US04_SEQ.txt, which is 30,013 bytes in size (measured in operating system MS windows) and was created on Apr. 19, 2018.

FIELD OF THE INVENTION

The present invention discloses molecular constructs and methods for the temporally specific control of gene expression in plants or in plant pests or pathogens. More particularly, this invention discloses novel plant miRNA genes that endogenously exhibit temporally specific expression. Also disclosed are recombinant DNA constructs for temporally specific expression of at least one gene, and non-natural transgenic plant cells, plants, and seeds containing in their genome a recombinant DNA construct of this invention. Further provided are methods of temporally specific expression of at least one gene using recombinant DNA constructs of this invention.

BACKGROUND OF THE INVENTION

MicroRNAs (miRNAs) are non-protein coding RNAs, generally of between about 19 to about 25 nucleotides (commonly about 20-24 nucleotides in plants), that guide cleavage in trans of target transcripts, negatively regulating the expression of genes involved in various regulation and development pathways (Bartel (2004) *Cell*, 116:281-297). In some cases, miRNAs serve to guide in-phase processing of siRNA primary transcripts (see Allen et al. (2005) *Cell*, 121:207-221). MicroRNA (MIR) genes have identifying characteristics, including conservation among plant species, a stable foldback structure, and processing of a specific miRNA/miRNA* duplex by Dicer-like enzymes (Ambros et al. (2003) *RNA*, 9:277-279). These characteristics have been used to identify miRNAs and their corresponding genes in plants (Xie et al. (2005) *Plant Physiol.*, 138:2145-2154; Jones-Rhoades and Bartel (2004) *Mol. Cell*, 14:787-799; Reinhart et al. (2002) *Genes Dev.*, 16:1616-1626; Sunkar and Zhu (2004) *Plant Cell*, 16:2001-2019).

Many microRNA genes (MIR genes) have been identified and made publicly available in a database ('miRBase", available on line at microrna.sanger.ac.uk/sequences; also see Griffiths-Jones et al. (2003) *Nucleic Acids Res.*, 31:439-441). Additional MIR genes and mature miRNAs are also described in U. S. Patent Application Publications 2005/0120415 and 2005/144669A1, which is incorporated by reference herein. MIR gene families appear to be substantial, estimated to account for 1% of at least some genomes and capable of influencing or regulating expression of about a third of all genes (see, for example, Tomari et al. (2005) *Curr. Biol.*, 15:R61-64; G. Tang (2005) *Trends Biochem. Sci.*, 30:106-14; Kim (2005) *Nature Rev. Mol. Cell Biol.*, 6:376-385). MIR genes have been reported to occur in intergenic regions, both isolated and in clusters in the genome, but can also be located entirely or partially within introns of other genes (both protein-coding and non-protein-coding). For a recent review of miRNA biogenesis, see Kim (2005) *Nature Rev. Mol. Cell Biol.*, 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA. See, for example, FIG. 1 in Kim (2005) *Nature Rev. Mol. Cell Biol.*, 6:376-385.

Maturation of a mature miRNA from its corresponding precursors (pri-miRNAs and pre-miRNAs) differs appreciably between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length, whereas in animals 22 nucleotide long miRNAs are most commonly found. For a recent review of miRNA biogenesis in both plants and animals, see Kim (2005) *Nature Rev. Mol. Cell Biol.*, 6:376-385. Additional reviews on miRNA biogenesis and function are found, for example, in Bartel (2004) *Cell*, 116:281-297; Murchison and Hannon (2004) *Curr. Opin. Cell Biol.*, 16:223-229; and Dugas and Bartel (2004) *Curr. Opin. Plant Biol.*, 7:512-520. Furthermore, although one recent report describes a miRNA (miR854) from *Arabidopsis* that also is found in animals (Arteaga-Vazquez et al. (2006) *Plant Cell*, 18:3355-3369), miRNA conservation generally appears to be kingdom-specific. Animal miRNAs have many characteristic dissimilar to their plant counterparts, including shorter miRNA precursor fold-backs (about 90 nucleotides in animals versus about 180 nucleotides in plants) with the mature miRNA sequence tending to be found at the base of the stem, a higher number of mismatches within the foldback, and deriviation from from polycistronic messages. Aimal miRNAs generally anneal imperfectly to the 3' untranslated region (UTR) of their target mRNA, and although functional miRNA recognition sites have not been identified in coding sequence or in the 5' UTR, animal miRNAs have been shown to bind to the 5' UTR of mRNAs encoded by recombinant constructs and to suppress translation (Lytle et al. (2007) *Proc. Natl. Acad. Sci. USA*, 104: 9667-9672). In contrast, most plant miRNAs are characterized by having perfect or near-perfect complementarity to their target sequence, which is usually in the coding region, with only a few examples of miRNAs having binding sites within the UTRs of the target mRNA; see Rhoades et al. (2002) *Cell*, 110:513-520; Jones-Rhoades et al. (2006) *Annu. Rev. Plant Biol.*, 57:19-53. These differences between plant and animal miRNAs make it generally unlikely that miRNAs will be processed and function across kingdoms.

Various utilities of miRNAs, their precursors, their recognition sites, and their promoters are described in detail in U. S. Patent Application Publication 2006/0200878 A1, incorporated by reference in its entirety herein. For example, transgenic expression of miRNAs (whether a naturally occurring sequence or an artificial sequence) is useful to regulate expression of the miRNA's target gene or genes. Animal miRNAs have been utilized as precursors to express specific miRNAs in animal cells; for example, the human miR-30 precursor was expressed as the native sequence and as a modified (artificial or engineered) miRNA in cultured cells (Zeng et al. (2002) *Mol. Cell,* 9:1327-1333, and Zeng et al. (2005) *J. Biol. Chem.,* 280:27595-27603). A single mature miRNA is precisely processed from a given miRNA precursor, and therefore such "artificial" or engineered miRNAs offer an advantage over double-stranded RNA (dsRNA) in that only a specific and predictable miRNA sequence is expressed, limiting potential off-target effects.

MiRNAs have been found to be expressed in very specific cell types in *Arabidopsis* (see, for example, Kidner and Martienssen (2004) *Nature,* 428:81-84, Millar and Gubler (2005) *Plant Cell,* 17:705-721). Suppression by a miRNA can be limited to a side, edge, or other division between cell types, and is believed to be required for proper cell type patterning and specification (see, for example, Palatnik et al. (2003) *Nature,* 425:257-263). Inclusion of a miRNA recognition site in a transgenically expressed transcript is also useful in regulating expression of the transcript; for example, suppression of a GFP reporter gene containing an endogenous miR171 recognition site was found to limit expression to specific cells in transgenic *Arabidopsis* (Parizotto et al. (2004) *Genes Dev.,* 18:2237-2242). Recognition sites of miRNAs have been validated in all regions of an mRNA, including the 5' untranslated region, coding region, and 3' untranslated region, indicating that the position of the miRNA target site relative to the coding sequence may not necessarily affect suppression (see, e. g., Jones-Rhoades and Bartel (2004) *Mol. Cell,* 14:787-799, Rhoades et al. (2002) *Cell,* 110:513-520, Allen et al. (2004) *Nat. Genet.,* 36:1282-1290, Sunkar and Zhu (2004) *Plant Cell,* 16:2001-2019). Expression of a transgene having a sequence that has modified to delete an endogenous miRNA recognition site permits expression of that transgene in a manner unregulated by the endogenous miRNA that would natively bind to the miRNA recognition site. Because miRNAs are important regulatory elements in eukaryotes, transgenic suppression of miRNAs is useful for manipulating biological pathways and responses. Importantly, promoters of miRNA genes can have very specific expression patterns (e. g., cell-specific, tissue-specific, temporally or developmentally specific, or inducible), and thus are useful in recombinant constructs to induce such specific transcription of a DNA sequence to which the promoter is operably linked.

In plants, many aspects of development, carbon assimilation, and nutrient uptake are regulated by day length. Manipulation of gene expression profiles, for example, by extending the expression or changing the circadian profile of transcript expression, is useful for changing the phenotype of the plant. For example, yield increase can be achieved by changing expression of genes related to carbon assimilation, e. g., carbon assimilation genes that are typically expressed only during the daytime can be modified to have extended periods of expression. Alternatively, the circadian cycle of the plant could be adjusted by changing expression profiles of the central clock.

10) Disclosed herein are miRNA genes having novel circadian expression patterns. These miRNA genes and their encoded mature miRNAs are useful, e. g., for modulating gene expression (see, for example, Palatnik et al. (2003) *Nature,* 425:257-263; Mallory et al. (2004) *Curr. Biol.,* 14:1035-1046), to serve as scaffolds or sequence sources for engineered (non-naturally occurring) miRNAs that are designed to target sequences other than the transcripts targetted by the naturally occurring miRNA sequence (see, for example, Parizotto et al. (2004) *Genes Dev.,* 18:2237-2242, and U.S. Patent Application Publications 2004/3411A1, 2005/0120415, which are incorporated by reference herein), and to stabilize dsRNA. A recognition site of a circadian miRNA gene is particularly useful as a relatively short sequence that can be added (e. g., to the non-coding regions of a transcript) to regulate control of a transcript. A miRNA gene itself (or its native 5' or 3' untranslated regions, or its native promoter or other elements involved in its transcription) is useful as a target sequence for gene suppression, where suppression of the miRNA encoded by the miRNA gene is desired. Promoters of circadian miRNA genes are useful in recombinant constructs to induce such temporally specific transcription of a DNA sequence to which they are operably linked.

SUMMARY OF THE INVENTION

11) In one aspect, this invention provides a recombinant DNA construct transcribable in a plant cell for temporally specific expression of at least one gene, wherein the expression of at least one gene is modulated by part or all of a circadian plant miRNA gene. The part or all of a circadian plant miRNA gene that modulates the expression of at least one gene is, in various embodiments, a mature miRNA natively transcribed from the circadian plant miRNA gene, or a promoter of a circadian plant miRNA gene (that is, DNA exhibiting temporally specific promoter activity in a plant and that is, or is derived from, the endogenous promoter of a circadian plant miRNA gene).

12) In a further aspect, this invention provides non-natural transgenic plant cells having in their genome a recombinant DNA construct transcribable in the plant cell for temporally specific expression of at least one gene, wherein the expression of at least one gene is modulated by part or all of a circadian plant miRNA gene. Also provided are a non-natural transgenic plant containing the transgenic plant cell of this invention, a non-natural transgenic plant grown from the transgenic plant cell of this invention, and non-natural transgenic seed produced by the transgenic plants, as well as commodity products produced from a non-natural transgenic plant cell, plant, or seed of this invention.

13) In yet another aspect, this invention provides methods of temporally regulating expression of a gene, including expressing in a plant a recombinant DNA construct of this invention, whereby the expression of at least one gene is modulated by part or all of a circadian miRNA gene of the plant, resulting in temporally specific expression of the at least one gene.

14) In still further aspects, this invention provides recombinant DNA constructs for modulating mesophyll expression of a transgene, methods for their use, and non-natural transgenic plant cells, plants, and seeds containing such constructs.

15) Other specific embodiments of the invention are disclosed in the following detailed description.

BRIEF DESCRIPTION OF THE DRAWINGS

17) FIG. 2 depicts part of the Gm-miRMON1 precursor (SEQ ID NO. 7) with the predicted fold-back structure, as described in Example 1. The mature Gm-miRMON1 miRNA (SEQ ID NO. 1) is indicated by the nucleotides in bold font within the fold-back.

Figure 5:
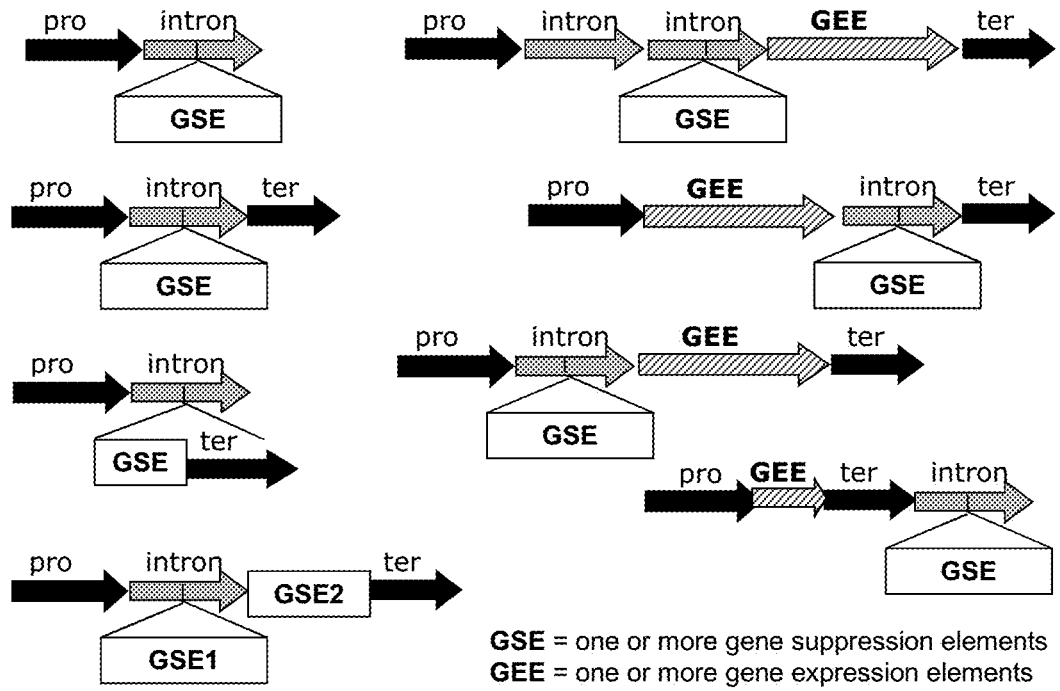
Figure 5:
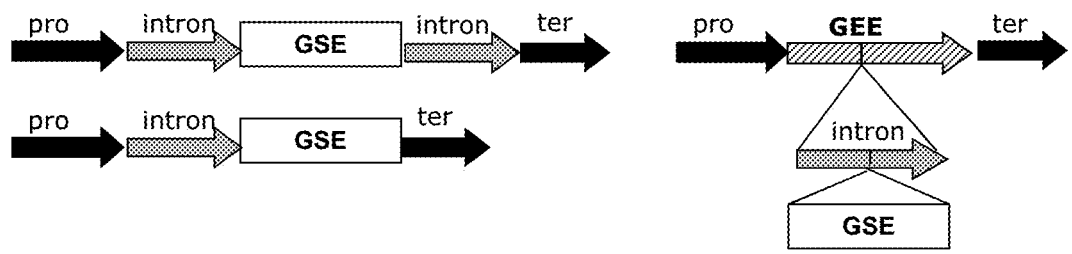

20) FIG. 5 schematically depicts non-limiting recombinant DNA constructs including gene suppression elements as described in Example 5. Panel A schematically depicts non-limiting examples of recombinant DNA constructs that illustrate arrangement of components of the construct. Panel B schematically depicts examples of prior art recombinant DNA constructs. For use in Agrobacterium-mediated transformation of plant cells, at least one T-DNA border is generally included in each construct (not shown). These constructs include a promoter element ("pro"), an intron flanked on one or on both sides by non-protein-coding DNA, an optional terminator element ("ter"), at least one first gene suppression element ("GSE" or "GSE1") for suppressing at least one first target gene, and, optionally, include at least one second gene suppression element ("GSE2") for suppressing at least one second target gene, at least one gene expression element ("GEE") for expressing at least one gene of interest, or both. In embodiments containing a gene expression element, the gene expression element can be located adjacent to (outside of) the intron. In one variation of this embodiment (not shown), the gene suppression element (embedded in an intron flanked on one or on both sides by non-protein-coding DNA) is located 3' to the terminator. In other constructs of the invention (not shown), a gene suppression element (not intron-embedded) is located 3' to the terminator.

Figure 6:
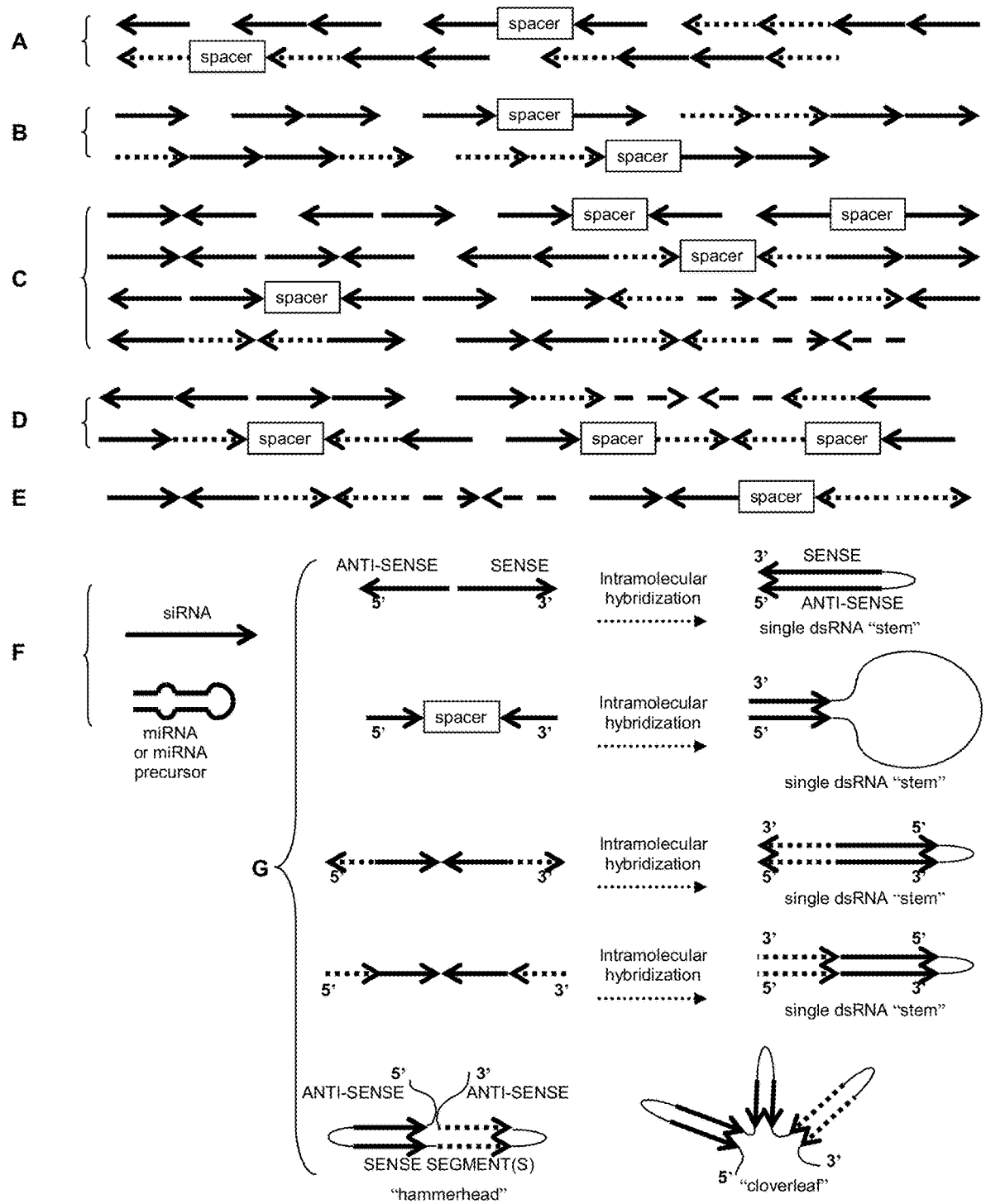

21) FIG. 6 depicts various non-limiting examples of gene suppression elements useful in recombinant DNA constructs of this invention, as described in Example 5. Where drawn as a single strand (Panels A through E), these are conventionally depicted in 5' to 3' (left to right) transcriptional direction, where the arrows indicate anti-sense sequence (arrowhead pointing to the left), or sense sequence (arrowhead pointing to the right). Where drawn as double-stranded (anti-parallel) transcripts (Panels F and G), the 5' and 3' transcriptional directionality is as shown. Solid lines, dashed lines, and dotted lines indicate sequences that target different target genes.

DETAILED DESCRIPTION OF THE INVENTION

22) Unless defined otherwise, all technical and scientific terms used have the same meaning as commonly understood by one of ordinary skill in the art to which this invention belongs. Generally, the nomenclature used and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art. Where a term is provided in the singular, the inventors also contemplate aspects of the invention described by the plural of that term. The nomenclature used and the laboratory procedures described below are those well known and commonly employed in the art. Where there are discrepancies in terms and definitions used in references that are incorporated by reference, the terms used in this application shall have the definitions given. Other technical terms used have their ordinary meaning in the art that they are used, as exemplified by a variety of technical dictionaries. The inventors do not intend to be limited to a mechanism or mode of action. Reference thereto is provided for illustrative purposes only.

Recombinant DNA Constructs for Temporally Specific Expression

23) In one aspect, this invention provides a recombinant DNA construct transcribable in a plant cell for temporally specific expression of at least one gene, wherein the expression of at least one gene is modulated by part or all of a circadian plant miRNA gene. This invention also provides non-natural transgenic plant cells and non-natural transgenic plants having in their genome any of the recombinant DNA constructs disclosed herein.

24) By temporally specific expression is meant expression that varies regularly and predictably over the period of a single day/night cycle, rather than expression that varies regularly and predictably over longer periods (e. g., annual seasons or ontogenic development). Thus, in many embodiments, temporally specific expression is circadian expression, that is, expression that varies with a periodicity of approximately 24 hours, which may or may not be acutely or immediately influenced by naturally occurring cues such as the naturally occurring light/dark periods or temperature increases/decreases of a normal day/night cycle. Environmental cues such as light quality or quantity or temperature can entrain (or even "reset") an endogenous "molecular clock" to appropriately synchronize it with existing environmental conditions. Plants' endogenous molecular clocks and the environmental stimuli that are involved in establishing and maintaining biologically appropriate circadian periodicity are reviewed by Miller (2004) J. Exp. Botany, 55:277-283.

25) Various embodiments of temporally specific expression include substantially diurnal expression, substantially nocturnal expression, light-induced expression, or light-suppressed expression, and a combination of these. Temporally specific expression can be characterized by a single period of expression during a single day/night cycle, or can be characterized by more than one period of expression during a single day/night cycle (e. g., crepuscular expression or bimodal expression primarily at dawn and at dusk). Overlap is possible between expression that is due to a molecular clock and expression that is acutely or immediately influenced by light or temperature.

26) "Circadian plant miRNA gene" refers generally to a gene encoding a miRNA precursor, or the endogenous promoter of such a gene, or to the mature miRNA that is natively transcribed from such a gene. Circadian plant miRNA genes natively exhibit circadian expression, e. g., substantially diurnal expression, substantially nocturnal expression, light-induced expression, or light-suppressed expression. Non-limiting examples of circadian plant miRNA genes disclosed herein include a miR390, TAS3 ta-siRNAs, miR393, mir156, mir159, and miRMON1, as further described in the Examples. The part or all of a circadian plant miRNA gene that modulates the expression of at least one gene can, for example, include a mature miRNA natively transcribed from the circadian plant miRNA gene, or a promoter of a circadian plant miRNA gene (that is, DNA exhibiting temporally specific promoter activity in a plant and that is, or is derived from, the endogenous promoter of a circadian plant miRNA gene).

27) In one aspect, this invention provides a recombinant DNA construct transcribable in a plant cell for temporally specific expression of at least one gene, wherein the expression of at least one gene is modulated by part or all of a circadian plant miRNA gene. The recombinant DNA construct of this invention can—but does not necessarily—encode either or both of: (1) the part or all of a circadian plant miRNA gene that modulates the expression of at least one gene, and (2) the gene whose expression is controlled by the part or all of a circadian plant miRNA.

28) In one embodiment, the recombinant DNA construct transcribable in a plant cell for temporally specific expression of at least one gene, wherein the expression of at least one gene is modulated by part or all of a circadian plant miRNA gene, includes (a) DNA encoding an exogenous miRNA recognition site that is recognizable by a mature miRNA natively transcribed from the circadian plant miRNA gene, and (b) DNA encoding the at least one gene; and the expression of at least one gene is decreased during time periods when the mature miRNA is transcribed relative to expression during time periods when the mature miRNA is not transcribed. In one non-limiting example, a recombinant DNA construct includes DNA encoding an exogenous miRNA recognition site that is recognized by a mature miRNA natively transcribed from a circadian plant miRNA gene, and DNA that encodes at least one polypeptide; translation of the polypeptide is decreased during time periods when the mature miRNA is transcribed relative to translation during time periods when the mature miRNA is not transcribed. In another non-limiting example, a recombinant DNA construct of this invention includes DNA encoding an exogenous miRNA recognition site that is recognized by a mature miRNA natively transcribed from a circadian plant miRNA gene, and DNA that transcribes to a non-coding gene suppression element (such as are described below under the heading "Gene Suppression Elements") that suppresses an endogenous target gene of the plant (or of a pest or pathogen of the plant) in which the construct is transcribed; the target gene is suppressed to a lesser degree during time periods when the mature miRNA is transcribed relative to time periods when the mature miRNA is not transcribed.

29) In another embodiment of the recombinant DNA construct transcribable in a plant cell for temporally specific expression of at least one gene, wherein the expression of at least one gene is modulated by part or all of a circadian plant miRNA gene, the recombinant DNA construct includes a promoter of a circadian plant miRNA gene operably linked to DNA encoding the at least one gene. In a non-limiting example, the recombinant DNA construct includes a promoter of a circadian plant miRNA gene operably linked to a transgene transcription unit, e. g., for expressing coding DNA. In another non-limiting example, the recombinant DNA construct includes a promoter of a circadian plant miRNA gene operably linked to a non-coding gene suppression element for suppressing a target gene.

30) Some embodiments of the recombinant DNA construct of this invention include both a transgene transcription unit for expressing at least one gene of interest and a gene suppression element for suppressing a target gene, either or both of which can be modulated by part or all of a circadian plant miRNA. In a non-limiting example, the recombinant DNA construct includes a constitutive promoter operably linked to an gene suppression element that is embedded in an intron, and to a transgene transcription unit that transcribes to a mRNA including an exogenous miRNA recognition site that is recognized by a mature miRNA natively transcribed from a circadian plant miRNA gene; such a construct transcribes to a gene suppression element that constitutively suppresses its target gene, and to an mRNA whose expression is decreased during time periods when the mature miRNA is transcribed relative to expression during time periods when the mature miRNA is not transcribed.

31) Other aspects of this invention provide a corollary approach to control of temporally specific expression and include a recombinant DNA construct to provide non-circadian expression of a gene that is natively under the control of an endogenous circadian plant miRNA gene. One embodiment is a recombinant DNA construct that encodes a transgene that derived from a gene natively under the control of an endogenous circadian plant miRNA gene (i. e., a gene that natively includes in its transcript a miRNA recognition site that is recognized by an endogenous mature miRNA natively transcribed from a circadian plant miRNA gene), but that is engineered to lack a miRNA recognition site that is recognized by an endogenous mature miRNA natively transcribed from a circadian plant miRNA gene. Another embodiment is a recombinant DNA construct for suppressing the endogenous circadian plant miRNA gene that natively causes circadian expression of the gene. Another embodiment is a recombinant DNA construct for expression of an endogenous circadian plant miRNA precursor under the control of a promoter other than its endogenous promoter. The mature miRNA (either as a native sequence or modified) is transcribed from the miRNA precursor in an expression pattern different from its native expression pattern; for example, a mature miRNA that is natively nocturnally expressed can be expressed under the control of a promoter having a different expression pattern, e. g., a constitutive or diurnal or inducible promoter. Promoters of use in these embodiments are described below under "Promoters". This approach is useful for suppressing expression of endogenous genes natively containing recognition sites for the mature miRNA in an expression pattern different from the native pattern.

32) Thus, in various embodiments, the recombinant DNA construct can include one or more elements selected from: (a) a promoter functional in a plant cell; (b) a transgene transcription unit; (c) a gene suppression element; and (d) a transcription regulatory/transcript stabilizing element; these are described below, see especially the discussion under the headings "Promoters", "Transgene Transcription Units", "Gene Suppression Elements", and "Transcription Regulatory Elements".

33) The recombinant DNA constructs disclosed herein are made by techniques known in the art, such as those described under the heading "Making and Using Recombinant DNA Constructs" and illustrated in the working Examples. The recombinant DNA construct is particularly useful for making non-natural transgenic plant cells, non-natural transgenic plants, and non-natural transgenic seeds as discussed below under "Making and Using Transgenic Plant Cells and Transgenic Plants".

Genes for Temporally Specific Expression

34) The at least one gene for temporally specific expression (i. e., whose expression is controlled by the part or all of a circadian plant miRNA) includes coding DNA (e. g., a transgene transcription unit encoding a polypeptide), non-coding DNA (e. g., a gene suppression element that encodes no polypeptide), or both, and can include any gene or genes of interest for which temporally specific expression is desired. The at least one gene for temporally specific expression can be, but is not necessarily, encoded by the recombinant DNA construct of this invention. The at least one gene can include an native (non-transgenic) gene endogenous to the plant cell, a gene endogenous to a invertebrate pest or viral, bacterial, or fungal pathogen of the plant, a transgene to be expressed in the plant cell, or any combination of these. The at least one gene can include a single gene or allele or multiple genes or alleles. The at least one gene can include a selectable marker or reporter gene.

35) In many embodiments, at least one gene for temporally specific expression is a target gene for temporally specific suppression. In one example, the at least one gene for temporally specific expression includes a gene suppression element, and the gene suppression element can suppress any target gene. Gene suppression elements and target genes are described below under "Gene Suppression Elements" and "Target Genes".

Recombinant DNA Constructs Encoding an Exogenous miRNA Recognition Site

36) In one embodiment, the recombinant DNA construct includes (a) DNA encoding an exogenous miRNA recognition site that is recognizable by a mature miRNA natively transcribed from the circadian plant miRNA gene, and (b) DNA encoding the at least one gene; and the expression of at least one gene is decreased during time periods when the mature miRNA is transcribed relative to expression during time periods when the mature miRNA is not transcribed. Non-limiting embodiments of the method include those wherein the circadian miRNA gene encodes a mature miRNA selected from the group consisting of a miR390, TAS3 ta-siRNAs, miR393, mir156, mir159, and miRMON1 (as described in the Examples). In a non-limiting example, the recombinant DNA construct includes (a) DNA encoding an exogenous miRNA recognition site that is recognizable by Gm-miRMON1 (SEQ ID NO. 1), and (b) DNA encoding the at least one gene; and the expression of at least one gene is substantially decreased at night relative to expression during the day.

37) The at least one miRNA recognition site is exogenous, that is, occurring in other than a naturally occurring or native context. The exogenous miRNA recognition site is positioned in the recombinant DNA construct in a location such that, upon transcription, the resulting transcript is recognized and bound by the mature miRNA (when endogenously transcribed) and the resulting transcript/miRNA duplex is cleaved, resulting in a decrease in expression of the gene during time periods when the mature miRNA is transcribed relative to expression during time periods when the mature miRNA is not transcribed. One or more (identical or different) exogenous miRNA recognition sites can be variously located in RNA transcribed from the recombinant DNA construct: (a) in the 5' untranslated region of an mRNA, (b) in the 3' untranslated region of an mRNA, (c) within an mRNA, (d) within non-coding transcript (for example, within part of a non-coding gene suppression element). Inclusion of the exogenous miRNA recognition site within a coding region may be constrained by the requirements of the amino acid sequence, but is generally possible if the inclusion does not produce translated polypeptides with undesirable characteristics (e. g., loss or decrease of function).

38) Cleavage of a target RNA transcript by a miRNA and the subsequent suppression of the target RNA are dependent on base pairing between the mature miRNA and its cognate miRNA recognition site. Thus, the exogenous miRNA recognition site preferably has sufficient sequence complementarity to the mature circadian plant miRNA to allow recognition and binding by the mature miRNA. In plants, sequence complementarity of a miRNA and its recognition site is typically high, e. g., perfect complementarity between 19, 20, or 21 out of 21 nucleotides (in the case of a mature miRNA that is 21 nucleotides in length), that is, complementarity of about 90% or greater. A similar degree of complementarity is preferable for recognition sites for plant miRNAs of any length (e. g., 20, 21, 22, 23, and 24 nucleotides). The sequence requirements for mature miRNA binding to a recognition site, and methods for predicting miRNA binding to a given sequence, are discussed, for example, in Llave et al. (2002) *Science*, 297:2053-2056, Rhoades et al. (2002) *Cell*, 110:513-520, Jones-Rhoades and Bartel (2004)*Mol. Cell*, 14:787-799, Schwab et al (2005) *Developmental Cell*, 8:517-527, and Xie et al. (2005) *Plant Physiol.*, 138:2145-2154. When designing a circadian plant miRNA recognition site as well as its exact location in or adjacent to a messenger RNA, it is also preferable to avoid sequences that have undesirable characteristics, such sequences encoding undesirable polypeptides, as described below under the heading "Target Genes". Conversely, when designing messenger RNA as a transgene to be expressed, the unintentional introduction of an exogenous miRNA recognition site is avoided where suppression by an endogenous mature miRNA is not desired.

39) Expression of the at least one gene encoded by this embodiment of the recombinant DNA construct is decreased during time periods when the mature miRNA is transcribed relative to expression during time periods when the mature miRNA is not transcribed. Thus, in various embodiments of this recombinant DNA construct, the circadian plant miRNA gene is natively characterized by substantially diurnal transcription and the expression of at least one gene is substantially nocturnal; or the circadian plant miRNA gene is natively characterized by substantially nocturnal transcription and the expression of at least one gene is substantially diurnal; or the circadian plant miRNA gene is natively characterized by substantially light-induced transcription and the expression of at least one gene is substantially light-suppressed; or the circadian plant miRNA gene is natively characterized by substantially light-suppressed transcription and the expression of at least one gene is substantially light-induced. By "substantially diurnal transcription" is meant transcription that occurs predominantly during daytime. By "substantially nocturnal transcription" is meant transcription that occurs predominantly during nighttime. Diurnal and nocturnal transcription can be, but are not necessarily, immediately or directly influenced by the presence or absence of light; for example, a gene that natively has diurnal or nocturnal expression may continue to exhibit that expression pattern for at least a few days even if the normal light/dark cycle is interrupted or changed. In contrast, "light-induced" or "light-suppressed" transcription is immediately or directly influenced by the presence or absence of light (e. g., transcription that is induced by light provided artificially outside natural daylight hours).

Recombinant DNA Constructs Including a Circadian Plant miRNA Promoter

40) In another embodiment, the part or all of a circadian plant miRNA gene includes a promoter of a circadian plant miRNA gene, and the recombinant DNA construct includes the promoter operably linked to DNA encoding the at least one gene. The promoter can be any endogenous promoter of a circadian plant miRNA gene. Procedures for identifying these promoters and testing their promoter activity are known in the art (see, for example, the review of plant promoter identification by Rombauts et al. (2003) *Plant Physiol.*, 132:1162-1176), and non-limiting examples of such techniques are illustrated in the Examples below.

41) The promoter can be a promoter that is derived from the endogenous promoter of a circadian plant miRNA gene, so long as it has promoter function with a circadian expression pattern in a plant cell. The native sequence of a circadian plant miRNA gene promoter can be modified without loss of the desired promoter function, for example by truncation, nucleotide addition or removal, or by addition of promoter enhancing sequences. Typical promoter motifs such as CAAT and TATA box elements are preferably included in the promoter. Modified promoters can be tested for the desired promoter function by commonly employed techniques, such as by the use of test constructs including the promoter operably linked to a reporter gene such as gus, gfp, or luc, and transient or non-transient transformation assays such as those described below in the Examples. Promoters of use in this invention therefore include promoters derived from an endogenous promoter of a circadian plant miRNA gene and having promoter function with a circadian expression pattern in a plant cell, for example, a fragment including at least about 50, about 100, about 150, about 200, about 250, about 300, about 350, about 400, about 450, or about 500 contiguous nucleotides of an endogenous promoter of a circadian plant miRNA gene, or a fragment of at least 100 nucleotides having at least 85%, at least 90%, or at least 95% identity to a segment of equivalent length of an endogenous promoter of a circadian plant miRNA gene, wherein such a fragment has promoter function with a circadian expression pattern in a plant cell.

42) Non-limiting examples of a promoter of a circadian plant miRNA gene include the endogenous promoters of a miR390, TAS3 ta-siRNAs, miR393, mir156, mir159, and miRMON1 (see the working Examples below), as well as promoters derived from these, such as a promoter that includes a fragment of at least 100 nucleotides having at least 85%, at least 90%, or at least 95% identity to a segment of equivalent length of an endogenous promoter of a miR390, TAS3 ta-siRNAs, miR393, mir156, mir159, and miRMON1 and that exhibits circadian promoter activity in a plant. In a specific, non-limiting example, the promoter includes SEQ ID NO. 30 or includes at least 100 contiguous nucleotides having at least 95% sequence identity to a fragment of at least 100 contiguous nucleotides from nucleotides 1-394 of SEQ ID NO. 30, and exhibits circadian promoter activity in a plant, and the expression of at least one gene is substantially nocturnal.

43) Expression of the at least one gene encoded by the recombinant DNA construct mimics the endogenous expression pattern of the circadian plant miRNA gene whose promoter (or derivative promoter) is used in the recombinant DNA construct. For example, where the construct includes the promoter of a circadian plant miRNA gene natively having diurnal expression, the gene encoded by the construct will also exhibit diurnal expression, that is, the at least one gene has increased expression during time periods when the mature miRNA is natively transcribed relative to expression during time periods when the mature miRNA is not natively transcribed. Thus, in various embodiments of this recombinant DNA construct, the circadian plant miRNA gene is natively characterized by substantially diurnal transcription and the expression of at least one gene is substantially diurnal; or the circadian plant miRNA gene is natively characterized by substantially nocturnal transcription and the expression of at least one gene is substantially nocturnal; or the circadian plant miRNA gene is natively characterized by substantially light-induced transcription and the expression of at least one gene is substantially light-induced; or (d) the circadian plant miRNA gene is natively characterized by substantially light-suppressed transcription and the expression of at least one gene is substantially light-suppressed.

Promoters

44) Certain embodiments of this invention include a recombinant DNA construct including a promoter that is not a promoter of a circadian plant miRNA gene (for example, constructs including DNA encoding an exogenous miRNA recognition site that is recognizable by a mature miRNA natively transcribed from the circadian plant miRNA gene). In such cases, the promoter is preferably a promoter functional in a plant cell. In various embodiments, the promoter is selected from the group consisting of a constitutive promoter, a spatially specific promoter, a temporally specific promoter, a developmentally specific promoter, and an inducible promoter.

45) Non-constitutive promoters suitable for use with recombinant DNA constructs of the invention include spatially specific promoters, developmentally specific promoters, and inducible promoters. Spatially specific promoters can include organelle-, cell-, tissue-, or organ-specific promoters (e. g., a plastid-specific, a root-specific, a pollen-specific, or a seed-specific promoter for suppressing expression of the first target RNA in plastids, roots, pollen, or seeds, respectively). In many cases a seed-specific, embryo-specific, aleurone-specific, or endosperm-specific promoter is especially useful. Developmentally specific promoters can include promoters that tend to promote expression during certain developmental stages in a plant's growth cycle, or at different seasons in a year. Inducible promoters include promoters induced by chemicals or by environmental conditions such as, but not limited to, biotic or abiotic stress (e. g., water deficit or drought, heat, cold, high or low nutrient or salt levels, high or low light levels, or pest or pathogen infection). Of particular interest are microRNA promoters, especially those having a developmentally specific, spatially specific, or inducible expression pattern. An expression-specific promoter can also include promoters that are generally constitutively expressed but at differing degrees or "strengths" of expression, including promoters commonly regarded as "strong promoters" or as "weak promoters".

46) Promoters of particular interest include the following non-limiting examples: an opaline synthase promoter isolated from T-DNA of *Agrobacterium*; a cauliflower mosaic virus 35S promoter; enhanced promoter elements or chimeric promoter elements such as an enhanced cauliflower mosaic virus (CaMV) 35S promoter linked to an enhancer element (an intron from heat shock protein 70 of *Zea mays*); root specific promoters such as those disclosed in U.S. Pat. Nos. 5,837,848; 6,437,217 and 6,426,446; a maize L3 oleosin promoter disclosed in U.S. Pat. No. 6,433,252; a promoter for a plant nuclear gene encoding a plastid-localized aldolase disclosed in U. S. Patent Application Publication 2004/0216189; cold-inducible promoters disclosed in U.S. Pat. No. 6,084,089; salt-inducible promoters disclosed in U.S. Pat. No. 6,140,078; light-inducible promoters disclosed in U.S. Pat. No. 6,294,714; pathogen-inducible promoters disclosed in U.S. Pat. No. 6,252,138; and water deficit-inducible promoters disclosed in U.S. Patent Application Publication 2004/0123347 A1. All of the above-described patents and patent publications disclosing promoters and their use, especially in recombinant DNA constructs functional in plants are incorporated herein by reference.

47) Plant vascular- or phloem-specific promoters of interest include a rolC or rolA promoter of *Agrobacterium rhizogenes*, a promoter of a *Agrobacterium tumefaciens* T-DNA gene 5, the rice sucrose synthase RSs1 gene promoter, a *Commelina* yellow mottle badnavirus promoter, a coconut foliar decay virus promoter, a rice tungro bacilliform virus promoter, the promoter of a pea glutamine synthase GS3A gene, a invCD111 and invCD141 promoters of a potato invertase genes, a promoter isolated from *Arabidopsis* shown to have phloem-specific expression in tobacco by Kertbundit et al. (1991), a VAHOX1 promoter region, a pea cell wall invertase gene promoter, an acid invertase gene promoter from carrot, a promoter of a sulfate transporter gene Sultr1;3, a promoter of a plant sucrose synthase gene, and a promoter of a plant sucrose transporter gene.

48) The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer and a regulatory region (which can be cis-acting). See, for example, Isaacs et al. (2004) *Nat. Biotechnol.*, 22:841-847, Bayer and Smolke (2005) *Nature Biotechnol.*, 23:337-343, Mandal and Breaker (2004) *Nature Rev. Mol. Cell Biol.*, 5:451-463, Davidson and Ellington (2005) *Trends Biotechnol.*, 23:109-112, Winkler et al. (2002) *Nature*, 419:952-956, Sudarsan et al. (2003) *RNA*, 9:644-647, and Mandal and Breaker (2004) *Nature Struct. Mol. Biol.*, 11:29-35. Such "riboregulators" could be selected or designed for specific spatial or temporal specificity, for example, to regulate translation of the DNA encoding the recombinant miRNA precursor only in the presence (or absence) of a given concentration of the appropriate ligand. One non-limiting example is a riboregulator that is responsive to an endogenous ligand (e. g., jasmonic acid or salicylic acid) produced by the plant when under stress (e. g., abiotic stress such as water, temperature, or nutrient stress, or biotic stress such as attach by pests or pathogens); under stress, the level of endogenous ligand increases to a level sufficient for the riboregulator to begin transcription of the DNA encoding the recombinant miRNA precursor.

Transgene Transcription Units

49) A transgene transcription unit includes DNA sequence encoding a gene of interest. A gene of interest can include any coding or non-coding sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, and mammals. Non-limiting examples of a non-coding sequence to be expressed by a transgene transcription unit include, but not limited to, 5' untranslated regions, promoters, enhancers, or other non-coding transcriptional regions, 3' untranslated regions, terminators, intron, microRNAs, microRNA precursor DNA sequences, small interfering RNAs, RNA components of ribosomes or ribozymes, small nucleolar RNAs, RNA aptamers capable of binding to a ligand, and other non-coding RNAs. Non-limiting examples of a gene of interest further include, but are not limited to, translatable (coding) sequence, such as genes encoding transcription factors and genes encoding enzymes involved in the biosynthesis or catabolism of molecules of interest (such as amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A gene of interest can be a gene native to the cell (e. g., a plant cell) in which the recombinant DNA construct of the invention is to be transcribed, or can be a non-native gene. A gene of interest can be a marker gene, for example, a selectable marker gene encoding antibiotic, antifungal, or herbicide resistance, or a marker gene encoding an easily detectable trait (e. g., in a plant cell, phytoene synthase or other genes imparting a particular pigment to the plant), or a gene encoding a detectable molecule, such as a fluorescent protein, luciferase, or a unique polypeptide or nucleic acid "tag" detectable by protein or nucleic acid detection methods, respectively). Selectable markers are genes of interest of particular utility in identifying successful processing of constructs of the invention. Genes of interest include those genes also described above as target genes, under the heading "Target Genes". The transgene transcription unit can further include 5' or 3' sequence or both as required for transcription of the transgene.

Gene Suppression Elements

50) Various embodiments of the recombinant DNA constructs of this invention include DNA that transcribes to a non-coding gene suppression element that suppresses an endogenous target gene of the plant (or of a pest or pathogen of the plant) in which the construct is transcribed. Gene suppression elements include any DNA sequence (or RNA sequence encoded therein) designed to specifically suppress a target gene or genes of interest.

51) Suitable gene suppression elements are described in detail in U. S. Patent Application Publication 2006/0200878, incorporated herein by reference, and include one or more of:
  (a) DNA that includes at least one anti-sense DNA segment that is anti-sense to at least one segment of the target gene;
  (b) DNA that includes multiple copies of at least one anti-sense DNA segment that is anti-sense to at least one segment of the target gene;
  (c) DNA that includes at least one sense DNA segment that is at least one segment of the target gene;
  (d) DNA that includes multiple copies of at least one sense DNA segment that is at least one segment of the target gene;
  (e) DNA that transcribes to RNA for suppressing the target gene by forming double-stranded RNA and includes at least one anti-sense DNA segment that is anti-sense to at least one segment of the target gene and at least one sense DNA segment that is at least one segment of the target gene;

(f) DNA that transcribes to RNA for suppressing the target gene by forming a single double-stranded RNA and includes multiple serial anti-sense DNA segments that are anti-sense to at least one segment of the target gene and multiple serial sense DNA segments that are at least one segment of the target gene;

(g) DNA that transcribes to RNA for suppressing the target gene by forming multiple double strands of RNA and includes multiple anti-sense DNA segments that are anti-sense to at least one segment of the target gene and multiple sense DNA segments that are at least one segment of the target gene, and wherein the multiple anti-sense DNA segments and the multiple sense DNA segments are arranged in a series of inverted repeats;

(h) DNA that includes nucleotides derived from a plant miRNA;

(i) DNA that includes nucleotides of a siRNA;

(j) DNA that transcribes to an RNA aptamer capable of binding to a ligand; and (k) DNA that transcribes to an RNA aptamer capable of binding to a ligand, and DNA that transcribes to regulatory RNA capable of regulating expression of the target gene, wherein the regulation is dependent on the conformation of the regulatory RNA, and the conformation of the regulatory RNA is allosterically affected by the binding state of the RNA aptamer.

52) DNA elements for suppressing expression are described further in Example 5 and depicted in FIGS. 5 and 6. DNA that includes nucleotides derived from a plant miRNA includes native miRNA precursor sequence or native mature miRNA sequence that is expressed under non-native conditions (e. g., under the control of an exogenous promoter), engineered miRNA precursors or engineered mature miRNAs, and exogenous miRNA recognition sites (e. g., in a recombinant DNA construct including both a target gene and an exogenous miRNA recognition site, wherein endogenous expression of the corresponding mature miRNA results in suppression of the target gene).

Transcription Regulatory Elements

53) Recombinant DNA constructs of this invention can further include one or more transcription regulatory elements, i. e., elements that regulate the expression level of the recombinant DNA construct of this invention (relative to its expression in the absence of such regulatory elements). Non-limiting examples of suitable transcription regulatory elements include riboswitches (cis- or trans-acting) and miRNA recognition sites, as described in detail in U. S. Patent Application Publication 2006/0200878, incorporated herein by reference. Other examples of transcription regulatory elements include transcript stabilizing elements such as an RNA that assumes a secondary structure or three-dimensional configuration (e. g., a loop, stem-loop, pseudoknot) that confers on the transcript increased stability or increased half-life in vivo; an RNA aptamer that confers on the transcript increased cell or tissue specificity; and transcript destabilizing elements such as the SAUR destabilizing sequences described in detail in U. S. Patent Application Publication 2007/0011761, incorporated herein by reference.

Target Genes

54) The gene suppression element is designed to suppress one or more target genes. Target genes include genes endogenous to the transgenic plant cell or genes exogenous to the plant (such as transgenes or genes endogenous to a pest or pathogen of the plant). Non-limiting examples of suitable target genes also include amino acid catabolic genes (such as, but not limited to, the maize LKR/SDH gene encoding lysine-ketoglutarate reductase (LKR) and saccharopine dehydrogenase (SDH), and its homologues), maize zein genes, genes involved in fatty acid synthesis (e. g., plant microsomal fatty acid desaturases and plant acyl-ACP thioesterases, such as, but not limited to, those disclosed in U.S. Pat. Nos. 6,426,448, 6,372,965, and 6,872,872), genes involved in multi-step biosynthesis pathways, where it may be of interest to regulate the level of one or more intermediates, such as genes encoding enzymes for polyhydroxyalkanoate biosynthesis (see, for example, U.S. Pat. No. 5,750,848); and genes encoding cell-cycle control proteins, such as proteins with cyclin-dependent kinase (CDK) inhibitor-like activity (see, for example, genes disclosed in International Patent Application Publication Number WO 05007829A2). Target genes can include genes encoding undesirable proteins (e. g., allergens or toxins) or the enzymes for the biosynthesis of undesirable compounds (e. g., undesirable flavor or odor components). Thus, one embodiment of the invention is a non-natural transgenic plant or tissue of such a plant that is further improved by the suppression of allergenic proteins or toxins, e. g., a peanut, soybean, or wheat kernel with decreased allergenicity. Target genes can include genes involved in fruit ripening, such as polygalacturonase. Target genes can include genes where expression is preferably limited to a particular cell or tissue or developmental stage, or where expression is preferably transient, that is to say, where constitutive or general suppression, or suppression that spreads through many tissues, is not necessarily desired. Thus, other examples of suitable target genes include genes encoding proteins that, when expressed in transgenic plants, make the transgenic plants resistant to pests or pathogens (see, for example, genes for cholesterol oxidase as disclosed in U.S. Pat. No. 5,763,245); genes where expression is pest- or pathogen-induced; and genes which can induce or restore fertility (see, for example, the barstar/barnase genes described in U.S. Pat. No. 6,759,575); all the patents cited in this paragraph are incorporated by reference in their entirety herein.

55) The target gene can include a single gene or part of a single gene that is targetted for suppression, or can include, for example, multiple consecutive segments of a target gene, multiple non-consecutive segments of a target gene, multiple alleles of a target gene, or multiple target genes from one or more species. The target gene can be translatable (coding) sequence, or can be non-coding sequence (such as non-coding regulatory sequence), or both. Non-limiting examples of a target gene include non-translatable (non-coding) sequence, such as, but not limited to, 5' untranslated regions, promoters, enhancers, or other non-coding transcriptional regions, 3' untranslated regions, terminators, and introns. Target genes include genes encoding microRNAs (that is, the primary transcript encoding an endogenous microRNA, or the RNA intermediates processed from this primary transcript), small interfering RNAs, RNA components of ribosomes or ribozymes, small nucleolar RNAs, and other non-coding RNAs (see, for example, non-coding RNA sequences provided publicly at rfam.wustl.edu; Erdmann et al. (2001) *Nucleic Acids Res.*, 29:189-193; Gottesman (2005) *Trends Genet.*, 21:399-404; Griffiths-Jones et al. (2005) *Nucleic Acids Res.*, 33:121-124). Target genes can also include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

56) In some embodiments the target gene for suppression is an essential gene of an invertebrate pest. Essential genes include genes that are required for development of the invertebrate pest to a fertile reproductive adult. Essential genes include genes that, when silenced or suppressed, result in the death of the invertebrate pest (as an adult or at any developmental stage, including gametes) or in the invertebrate pest's inability to successfully reproduce (e. g., sterility in a male or female parent or lethality to the zygote, embryo, or larva). A description of nematode essential genes is found, e. g., in Kemphues, K. "Essential Genes" (Dec. 24, 2005), WormBook, ed. The *C. elegans* Research Community, WormBook, doi/10.1895/wormbook.1.57.1, available on line at www(dot)wormbook(dot)org. Soybean cyst nematode essential genes are disclosed in U.S. patent application Ser. No. 11/360,355, filed 23 Feb. 2006, specifically incorporated by reference herein. Non-limiting examples of invertebrate essential genes include major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, as well as other genes such as those disclosed in U. S. Patent Application Publication 2006/0021087 A1, PCT Patent Application PCT/US05/11816, and in Table II of U. S. Patent Application Publication 2004/0098761 A1, which are specifically incorporated by reference herein. A description of insect genes is publicly available at the *Drosophila* genome database (available on line at flybase.bio.indiana.edu/). The majority of predicted *Drosophila* genes have been analyzed for function by a cell culture-based RNA interference screen, resulting in 438 essential genes being identified; see Boutros et al. (2004) *Science*, 303:832-835, and supporting material available on line at www(dot)sciencemag(dot)org/cgi/content/full/303/5659/832/DC1. Other examples of essential insect genes include a gut cell protein, a membrane protein, an ecdysone receptor, ATPases such as gamma-ATPase, an amino acid transporter, a transcription factor, a peptidylglycine alpha-amidating monooxygenase; a cysteine protease, an amino-peptidase, a dipeptidase, a sucrase/transglucosidase, a translation elongation factor, an eukaryotic translation initiation factor 1A, a splicing factor, an apoptosis inhibitor; a tubulin protein, an actin protein, an alpha-actinin protein, a histone, a histone deacetylase, a cell cycle regulatory protein, a cellular respiratory protein; a receptor for an insect-specific hormonal signal, a juvenile hormone receptor, an insect peptidic hormone receptor; a protein regulating ion balance in a cell, a proton-pump, a Na/K pump, an intestinal protease; an enzyme involved in sucrose metabolism, a digestive enzyme, a trypsin-like protease and a cathepsin B-like protease.

57) Plant pest invertebrates include, but are not limited to, nematodes, molluscs (slugs and snails), and insects and arachnids. See also G. N. Agrios, "Plant Pathology" (Fourth Edition), Academic Press, San Diego, 1997, 635 pp., for descriptions of nematodes and flagellate protozoans, all of which are invertebrate pests of interest. See also the continually updated compilation of plant pests and the diseases caused by such on the American Phytopathological Society's "Common Names of Plant Diseases", compiled by the Committee on Standardization of Common Names for Plant Diseases of The American Phytopathological Society, 1978-2005, available online at apsnet(dot)org/online/common/top(dot)asp.

58) Non-limiting examples of invertebrate pests include cyst nematodes *Heterodera* spp. especially soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., foliar nematodes *Aphelenchus* spp. or *Aphelenchoides* spp., corn rootworms, *Lygus* spp., aphids and similar sap-sucking insects such as *phylloxera* (*Daktulosphaira vitifoliae*), corn borers, cutworms, armyworms, leafhoppers, Japanese beetles, grasshoppers, and other pest coleopterans, dipterans, and lepidopterans. Specific examples of invertebrate pests include pests capable of infesting the root systems of crop plants, e. g., northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), claybacked cutworm (*Agrotis gladiaria*), wireworm (*Melanotus* spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape colaspis (*Colaspis brunnea*), seedcorn beetle (*Stenolophus lecontei*), and slender seedcorn beetle (*Clivinia impressifrons*), as well as the parasitic nematodes listed in Table 6 of U.S. Pat. No. 6,194,636, which is specifically incorporated in its entirety by reference herein.

59) Invertebrate pests of particular interest, especially in but not limited to southern hemisphere regions (including South and Central America) include aphids, corn rootworms, *spodoptera*, noctuideae, potato beetle, *Lygus* spp., any hemipteran, homopteran, or heteropteran, any lepidopteran, any coleopteran, nematodes, cutworms, earworms, armyworms, borers, leaf rollers, and others. Arthropod pests specifically encompassed by this invention include various cutworm species including cutworm (*Agrotis repleta*), black cutworm (*Agrotis ipsilon*), cutworm (*Anicla ignicans*), granulate cutworm (*Feltia subterranea*), "gusano áspero" (*Agrotis malefida*); Mediterranean flour moth (*Anagasta kuehniella*), square-necked grain beetle (*Cathartus quadricollis*), flea beetle (*Chaetocnema* spp), rice moth (*Corcyra cephalonica*), corn rootworm or "vaquita de San Antonio" (*Diabotica speciosa*), sugarcane borer (*Diatraea saccharalis*), lesser cornstalk borer (*Elasmopalpus lignosellus*), brown stink bug (*Euschistus* spp.), corn earworm (*Helicoverpa zea*), flat grain beetle (*Laemophloeus minutus*), grass looper moth (Mods *latipes*), sawtoothed grain beetle (*Oryzaephilus surinamensis*), meal moth (*Pyralis farinalis*), Indian meal moth (*Plodia interpunctella*), corn leaf aphid (*Rhopalosiphum maidis*), brown burrowing bug or "chinche subterránea" (*Scaptocoris castanea*), greenbug (*Schizaphis graminum*), grain weevil (*Sitophilus zeamais*), Angoumois grain moth (*Sitotroga cerealella*), fall armyworm (*Spodoptera frugiperda*), cadelle beetle (*Tenebroides mauritanicus*), two-spotted spider mite (*Tetranychus urticae*), red flour beetle (*Triboleum castaneum*), cotton leafworm (*Alabama argillacea*), boll weevil (*Anthonomus grandis*), cotton aphid (*Aphis gossypii*), sweet potato whitefly (*Bemisia tabaci*), various *thrips* species (*Frankliniella* spp.), cotton earworm (*Helicoverpa zea*), "oruga bolillera" (e. g., *Helicoverpa* geletopoeon), tobacco budworm (*Heliothis virescens*), stinkbug (*Nezara viridula*), pink bollworm (*Pectinophora gossypiella*), beet armyworm (*Spodoptera exigua*), spider mites (*Tetranychus* spp.), onion thrips (*Thrips tabaci*), greenhouse whitefly (*Trialeurodes vaporarium*), velvetbean caterpillar (*Anticarsia gemmatalis*), spotted maize beetle or "astilo moteado" (*Astylus atromaculatus*), "oruga de la alfalfa" (*Colias lesbia*), "chinche marrón" or "chinche de los cuernos" (*Dichelops furcatus*), "alquiche chico" (Edessa miditabunda), blister beetles (Epicauta spp.), "barrenador del brote" (Epinotia aporema), "oruga verde del yuyo colorado" (*Loxostege bifidalis*), rootknot nematodes (*Meloidogyne* spp.), "oruga cuarteadora" (*Mocis repanda*), southern green stink bug (*Nezara viridula*), "chinche de la alfalfa" (*Piezodorus guildinii*), green cloverworm (*Plathypena scabra*), soybean looper (*Pseudoplusia includens*), looper moth "isoca medidora del girasol" (*Rachiplusia nu*), yellow woolybear (*Spilosoma virginica*), yellowstriped armyworm (*Spodoptera ornithogalli*), various root weevils (family Curculionidae), various wireworms (family Elateridae), and various white grubs (family Scarabaeidae). Nematode pests specifically encompassed by this invention include nematode pests of maize (*Belonolaimus* spp., *Trichodorus* spp., *Longidorus* spp., *Dolichodorus* spp., *Anguina* spp., *Pratylenchus* spp., *Meloidogyne* spp., *Heterodera* spp.), soybean (*Heterodera glycines, Meloidogyne* spp., *Belonolaimus* spp.), bananas (*Radopholus similis, Meloidogyne* spp., *Helicotylenchus* spp.), sugarcane (*Heterodera sacchari, Pratylenchus* spp., *Meloidogyne* spp.), oranges (*Tylenchulus* spp., *Radopholus* spp., *Belonolaimus* spp., *Pratylenchus* spp., *Xiphinema* spp.), coffee (*Meloidogyne* spp., *Pratylenchus* spp.), coconut palm (*Bursaphelenchus* spp.), tomatoes (*Meloidogyne* spp., *Belonolaimus* spp., Nacobbus spp.), grapes (*Meloidogyne* spp., *Xiphinema* spp., *Tylenchulus* spp., *Criconemella* spp.), lemon and lime (*Tylenchulus* spp., *Radopholus* spp., *Belonolaimus* spp., *Pratylenchus* spp., *Xiphinema* spp.), cacao (*Meloidogyne* spp., *Rotylenchulus reniformis*), pineapple (*Meloidogyne* spp., *Pratylenchus* spp., *Rotylenchulus reniformis*), papaya (*Meloidogyne* spp., *Rotylenchulus reniformis*), grapefruit (*Tylenchulus* spp., *Radopholus* spp. *Belonolaimus* spp., *Pratylenchus* spp., *Xiphinema* spp.), and broad beans (*Meloidogyne* spp.).

60) The recombinant DNA construct can be designed to be more specifically suppress the target gene, for example, by designing the recombinant DNA construct to encode a recombinant miRNA precursor that is processed to a mature miRNA that includes regions substantially non-complementary to a non-target gene sequence. Non-target genes can include any gene not intended to be silenced or suppressed, either in a plant containing the recombinant DNA construct or in organisms that may come into contact with the recombinant DNA construct. A non-target gene sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans).

61) In one embodiment, the target gene is a gene endogenous to a specific invertebrate pest species of interest, and the non-target gene is a gene or genes of one or more non-target species (such as a gene or genes of a plant species or a gene of a virus, fungus, bacterium, a non-target invertebrate, or vertebrate, even a human). One non-limiting example is where the recombinant DNA construct is designed to be processed to a mature miRNA for suppressing a target gene that is a gene endogenous to a single species (e. g., Western corn rootworm, *Diabrotica virgifera virgifera* LeConte) but not suppressing a non-target gene such as genes from related, even closely related, species (e. g., Northern corn rootworm, *Diabrotica barberi* Smith and Lawrence, or Southern corn rootworm, *Diabrotica undecimpunctata*).

62) In other embodiments (e. g., where it is desirable to suppress a target gene across multiple species), it may be desirable to design the recombinant DNA construct to be processed to a mature miRNA for suppressing a target gene sequence common to the multiple species in which the target gene is to be silenced. Thus, the miRNA processed from the recombinant DNA construct can be designed to be specific for one taxon (for example, specific to a genus, family, or even a larger taxon such as a phylum, e. g., arthropoda) but not for other taxa (e. g., plants or vertebrates or mammals). In one non-limiting example of this embodiment, the recombinant DNA construct can be designed to be processed to a mature miRNA for suppressing a target gene sequence common to aphids (Aphidoidea) but not target any gene sequence from other insects or invertebrates.

63) In another non-limiting example of this embodiment, a recombinant DNA construct for gene silencing in corn rootworm is designed to be processed to a mature miRNA for suppressing a target gene sequence common to all members of the genus *Diabrotica*. In a further example of this embodiment, such a *Diabrotica*-targetted recombinant DNA construct can be selected so as to not target any sequence from beneficial coleopterans (for example, predatory coccinellid beetles, commonly known as ladybugs or ladybirds) or other beneficial insect species.

64) The required degree of specificity of a recombinant DNA construct of this invention for silencing a target gene depends on various factors. Factors can include the size and nucleic acid sequence of the mature microRNA encoded by the recombinant DNA construct, and the relative importance of decreasing such a mature miRNA's potential to suppress non-target genes. In a non-limiting example, where such a mature miRNA is expected to be 22 base pairs in size, one particularly preferred embodiment includes DNA encoding a mature miRNA for silencing a target gene wherein the mature miRNA includes sequence that is substantially non-identical to a non-target gene sequence, such as fewer than 19, or fewer than 18, or fewer than 17, or fewer than 16, or fewer than 15 matches out of 22 contiguous nucleotides of a non-target gene sequence.

65) In some embodiments, it may be desirable to design the recombinant DNA construct to include regions predicted to not generate undesirable polypeptides, for example, by screening the recombinant DNA construct for sequences that may encode known undesirable polypeptides or close homologues of these. Undesirable polypeptides include, but are not limited to, polypeptides homologous to known allergenic polypeptides and polypeptides homologous to known polypeptide toxins. Publicly available sequences encoding such undesirable potentially allergenic peptides are available, for example, the Food Allergy Research and Resource Program (FARRP) allergen database (available at allergenonline(dot)com) or the Biotechnology Information for Food Safety Databases (available at www(dot)iit(dot)edu/~sgendel/fa(dot)htm) (see also, for example, Gendel (1998) *Adv. Food Nutr. Res.*, 42:63-92). Undesirable sequences can also include, for example, those polypeptide sequences annotated as known toxins or as potential or known allergens and contained in publicly available databases such as GenBank, EMBL, SwissProt, and others, which are searchable by the Entrez system (www(dot)ncbi(dot)nih(dot)gov/Entrez). Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish (allergenonline(dot)com). Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles (www(dot)ncbi(dot)nih(dot)gov/Entrez).

66) In one non-limiting example, the recombinant DNA construct is screened to eliminate those transcribable sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with AUG (ATG in the corresponding DNA), or on all possible reading frames, regardless of whether they start with an AUG (or ATG) or not. When a "hit" or match is made, that is, when a sequence that encodes a potential polypeptide with perfect homology to a known allergen or toxin over 8 contiguous amino acids (or at least about 35% identity over at least about 80 amino acids), is identified, the nucleic acid sequences corresponding to the hit can be avoided, eliminated, or modified when selecting sequences to be used in an RNA for silencing a target gene. In one embodiment the recombinant DNA construct is designed so no potential open reading frame that begins with AUG (ATG in the corresponding DNA) is included. Avoiding, elimination of, or modification of, an undesired sequence can be achieved by any of a number of methods known to those skilled in the art. In some cases, the result can be novel sequences that are believed to not exist naturally. For example, avoiding certain sequences can be accomplished by joining together "clean" sequences into novel chimeric sequences to be used in the recombinant DNA construct.

67) Applicants recognize that in some microRNA-mediated gene silencing, it is possible for imperfectly matching miRNA sequences to be effective at gene silencing. For example, it has been shown that mismatches near the center of a miRNA complementary site has stronger effects on the miRNA's gene silencing than do more distally located mismatches. See, for example, FIG. 4 in Mallory et al. (2004) *EMBO J.*, 23:3356-3364. In another example, it has been reported that both the position of a mismatched base pair and the identity of the nucleotides forming the mismatch influence the ability of a given siRNA to silence a target gene, and that adenine-cytosine mismatches, in addition to the G:U wobble base pair, were well tolerated (see Du et al. (2005) *Nucleic Acids Res.*, 33:1671-1677). Thus, a given strand of the recombinant DNA construct need not always have 100% sequence identity with the intended target gene, but generally would preferably have substantial sequence identity with the intended target gene, such as about 95%, about 90%, about 85%, or about 80% sequence identity with the intended target gene. Described in terms of complementarity, one strand of the recombinant DNA construct is preferably designed to have substantial complementarity to the intended target (e. g., a target messenger RNA or target non-coding RNA), such as about 95%, about 90%, about 85%, or about 80% complementarity to the intended target. In a non-limiting example, in the case of a recombinant DNA construct encoding a mature miRNA of 22 nucleotides, the encoded mature miRNA is designed to be is substantially but not perfectly complementary to 22 contiguous nucleotides of a target RNA; preferably the nucleotide at position 22 is unpaired with the corresponding position in the target RNA to prevent transitivity.

68) Persons of ordinary skill in the art are capable of judging the importance given to screening for regions predicted to be more highly specific to the target gene or predicted to not generate undesirable polypeptides, relative to the importance given to other criteria, such as, but not limited to, the percent sequence identity with the intended target gene or the predicted gene silencing efficiency of a given sequence. For example, a recombinant DNA construct of this invention is designed to be processed to a mature miRNA that is active across several target invertebrate pest species, and therefore one skilled in the art can determine that it is more important to include in the recombinant DNA construct DNA encoding a mature miRNA that is specific to the several invertebrate pest species of interest, but less important to screen for regions predicted to have higher gene silencing efficiency or for regions predicted to generate undesirable polypeptides.

Making and Using Recombinant DNA Constructs

69) The recombinant DNA constructs of this invention are made by any method suitable to the intended application, taking into account, for example, the type of expression desired and convenience of use in the plant in which the construct is to be transcribed. General methods for making and using DNA constructs and vectors are well known in the art and described in detail in, for example, handbooks and laboratory manuals including Sambrook and Russell, "Molecular Cloning: A Laboratory Manual" (third edition), Cold Spring Harbor Laboratory Press, N Y, 2001. An example of useful technology for building DNA constructs and vectors for transformation is disclosed in U. S. Patent Application Publication 2004/0115642 A1, incorporated herein by reference. DNA constructs can also be built using the GATEWAY™ cloning technology (available from Invitrogen Life Technologies, Carlsbad, Calif.), which uses the site-specific recombinase LR cloning reaction of the Integrase/att system from bacteriophage lambda vector construction, instead of restriction endonucleases and ligases. The LR cloning reaction is disclosed in U.S. Pat. Nos. 5,888,732 and 6,277,608, and in U. S. Patent Application Publications 2001/283529, 2001/282319 and 2002/0007051, which disclosures are specifically incorporated herein by reference. The GATEWAY™ Cloning Technology Instruction Manual, which is also supplied by Invitrogen, provides concise directions for routine cloning of any desired DNA into a vector comprising operable plant expression elements. Another alternative vector fabrication method employs ligation-independent cloning as disclosed by Aslandis et al. (1990) *Nucleic Acids Res.*, 18:6069-6074 and Rashtchian et al. (1992) *Biochem.*, 206:91-97, where a DNA fragment with single-stranded 5' and 3' ends is ligated into a desired vector which can then be amplified in vivo.

70) In certain embodiments, the DNA sequence of the recombinant DNA construct includes sequence that has been codon-optimized for the plant in which the recombinant DNA construct is to be expressed. For example, a recombinant DNA construct to be expressed in a plant can have all or parts of its sequence (e. g., the first gene suppression element or the gene expression element) codon-optimized for expression in a plant by methods known in the art. See, e. g., U.S. Pat. No. 5,500,365, incorporated by reference, for a description of codon-optimization methodology for plants; see also De Amicis and Marchetti (2000) *Nucleic Acid Res.*, 28:3339-3346.

Transgenic Plant Cells and Plants

71) Another aspect of this invention is a non-natural transgenic plant cell having in its genome a recombinant DNA construct transcribable in the plant cell for temporally specific expression of at least one gene, wherein the expression of at least one gene is modulated by part or all of a circadian plant miRNA gene. Also provided are a non-natural transgenic plant containing the non-natural transgenic plant cell of this invention, a non-natural transgenic plant grown from the non-natural transgenic plant cell of this invention, and non-natural transgenic seed produced by the non-natural transgenic plants. Such non-natural transgenic plant cells, plants, and seeds can be made using the techniques described below under the heading "Making and Using Transgenic Plant Cells and Transgenic Plants". This invention further provides a method of temporally regulating expression of a gene in a plant, including expressing in the plant a recombinant DNA construct transcribable in a plant cell for temporally specific expression of at least one gene, wherein the expression of at least one gene is modulated by part or all of a circadian plant miRNA gene, resulting in temporally specific expression of the at least one gene.

72) The non-natural transgenic plant of this invention includes plants of any developmental stage, and includes a non-natural transgenic regenerated plant prepared from the non-natural transgenic plant cells disclosed herein, or a non-natural transgenic progeny plant (which can be an inbred or hybrid progeny plant) of the regenerated plant, or non-natural transgenic seed of such a non-natural transgenic plant. Also provided is a non-natural transgenic seed having in its genome a recombinant DNA construct of this invention. The non-natural transgenic plant cells, non-natural transgenic plants, and non-natural transgenic seeds of this invention are made by methods well-known in the art, as described below under the heading "Making and Using Transgenic Plant Cells and Transgenic Plants".

73) The non-natural transgenic plant cell can include an isolated plant cell (e. g., individual plant cells or cells grown in or on an artificial culture medium), or can include a plant cell in undifferentiated tissue (e. g., callus or any aggregation of plant cells). The non-natural transgenic plant cell can include a plant cell in at least one differentiated tissue selected from the group consisting of leaf (e. g., petiole and blade), root, stem (e. g., tuber, rhizome, stolon, bulb, and corm) stalk (e. g., xylem, phloem), wood, seed, fruit (e. g., nut, grain, fleshy fruits), and flower (e. g., stamen, filament, anther, pollen, carpel, pistil, ovary, ovules).

74) The non-natural transgenic plant cell or non-natural transgenic plant of the invention can be any suitable plant cell or plant of interest. Both transiently transformed and stably transformed plant cells are encompassed by this invention. Stably transformed transgenic plants are particularly preferred. In many preferred embodiments, the non-natural transgenic plant is a fertile transgenic plant from which seed can be harvested, and the invention further claims non-natural transgenic seed of such transgenic plants, wherein the seed preferably also contains the recombinant construct of this invention.

75) In some embodiments of this invention, the non-natural plant is a non-natural transgenic plant, and all cells (with the possible exception of haploid cells) and tissues of the plant contain the recombinant DNA construct of this invention. In other embodiments, the non-natural plant is not completely transgenic, but includes both non-natural transgenic cells or tissues and non-transgenic cells or tissues (for example, transgenic tissue grafted onto non-transgenic tissue). In a non-limiting embodiment, the plant includes a non-transgenic scion and a transgenic rootstock including the transgenic plant cell, wherein the non-transgenic scion and transgenic rootstock are grafted together. Such embodiments are particularly useful where the plant is one that is commonly vegetatively grown as a scion grafted onto a rootstock (wherein scion and rootstock can be of the same species or variety or of different species or variety); non-limiting examples include grapes (e. g., wine grapes and table grapes), apples, pears, quince, avocados, citrus, stone fruits (e. g., peaches, plums, nectarines, apricots, cherries), kiwifruit, roses, and other plants of agricultural or ornamental importance.

76) Also encompassed by this invention are non-natural plants that are not transgenic in the sense of having had recombinant DNA introduced into their genome, but are non-natural plants having a genome that has been artificially modified by means other than recombinant DNA technology. Such artificial modifications of the native genomic sequence include insertions, deletions, substitutions, frame shifts, transpositions, duplications, and inversions. Artificial modification of a native genomic sequence is achieved by any means, including mutagenesis by chemicals (such as methane sulfonate, methyl methane sulfonate, diethylsulfate), nitrosoguanidine, and other alkylating agents, base analogues such as 5-bromo-deoxyuridine, interchelating agents such as ethidium bromide, crosslinking agents such as platinum, and oxidating agents such as nitrous acid or reactive oxygen species) or mutagenesis by physical treatments (such as exposure to ultraviolet light, radioactive isotopes, or ionizing radiation). Such mutagenesis can be random or non-random (e. g., site-directed mutagenesis). Mutagenesis can be carried out with intact plants, plant tissues, or plant cells. One non-limiting example of mutagenesis is treatment of maize pollen with an alkylating agent. Mutagenesis is generally carried out on a population, following screening of that population to allow selection of individuals having the desired property. These non-natural plants are useful in ways similar to those described below for transgenic plants; for example, they can be grown for production of seed or other harvestable parts, or used to grow progeny generations (including hybrid generations).

Making and Using Transgenic Plant Cells and Transgenic Plants

77) Where a recombinant DNA construct of this invention is used to produce a transgenic plant cell, transgenic plant, or transgenic seed of this invention, transformation can include any of the well-known and demonstrated methods and compositions. Suitable methods for plant transformation include virtually any method by which DNA can be introduced into a cell, such as by direct delivery of DNA (e. g., by PEG-mediated transformation of protoplasts, by electroporation, by agitation with silicon carbide fibers, and by acceleration of DNA coated particles), by *Agrobacterium*-mediated transformation, by viral or other vectors, etc. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and U.S. Pat. No. 6,399,861 (maize), and U.S. Pat. No. 6,403,865 (maize), all of which disclosures are specifically incorporated by reference.

78) Another preferred method of plant transformation is *Agrobacterium*-mediated transformation. In one preferred embodiment, the transgenic plant cell of this invention is obtained by transformation by means of *Agrobacterium* containing a binary Ti plasmid system, wherein the *Agro-*

*bacterium* carries a first Ti plasmid and a second, chimeric plasmid containing at least one T-DNA border of a wild-type Ti plasmid, a promoter functional in the transformed plant cell and operably linked to a gene suppression construct of the invention. See, for example, the binary system described in U.S. Pat. No. 5,159,135, specifically incorporated by reference. Also see De Framond (1983) *Biotechnology,* 1:262-269; and Hoekema et al., (1983) *Nature,* 303:179. In such a binary system, the smaller plasmid, containing the T-DNA border or borders, can be conveniently constructed and manipulated in a suitable alternative host, such as *E. coli*, and then transferred into *Agrobacterium*.

79) Detailed procedures for *Agrobacterium*-mediated transformation of plants, especially crop plants, include, for example, procedures disclosed in U.S. Pat. Nos. 5,004,863, 5,159,135, 5,518,908, 5,846,797, and 6,624,344 (cotton); U.S. Pat. Nos. 5,416,011, 5,569,834, 5,824,877, 5,914,451 6,384,301, and 7,002,058 (soy); U.S. Pat. No. 5,591,616 5,981,840, and 7,060,876 (maize); U.S. Pat. Nos. 5,463,174 and 5,750,871 (brassicas, including rapeseed and canola), and in U. S. Patent Application Publications 2004/0244075 (maize), 2004/0087030 (cotton) and 2005/0005321 (soy), all of which are specifically incorporated by reference. Additional procedures for *Agrobacterium*-mediated transformation are disclosed in WO9506722 (maize). Similar methods have been reported for many plant species, both dicots and monocots, including, among others, peanut (Cheng et al. (1996) *Plant Cell Rep.,* 15: 653); asparagus (Bytebier et al. (1987) *Proc. Natl. Acad. Sci. U.S.A.,* 84:5345); barley (Wan and Lemaux (1994) *Plant Physiol.,* 104:37); rice (Toriyama et al. (1988) *Bio/Technology,* 6:10; Zhang et al. (1988) *Plant Cell Rep.,* 7:379; wheat (Vasil et al. (1992) *Bio/Technology,* 10:667; Becker et al. (1994) *Plant J.,* 5:299), alfalfa (Masoud et al. (1996) *Transgen. Res.,* 5:313); brassicas (Radke et al. (1992) *Plant Cell Rep.,* 11:499-505); and tomato (Sun et al. (2006) *Plant Cell Physiol.,* 47:426-431). See also a description of vectors, transformation methods, and production of transformed *Arabidopsis thaliana* plants where transcription factors are constitutively expressed by a CaMV35S promoter, in U. S. Patent Application Publication 2003/0167537 A1, specifically incorporated by reference. Transgenic plant cells and transgenic plants can also be obtained by transformation with other vectors, such as, but not limited to, viral vectors (e. g., tobacco etch potyvirus (TEV), barley stripe mosaic virus (BSMV), and the viruses referenced in Edwardson and Christie, "The Potyvirus Group: Monograph No. 16, 1991, Agric. Exp. Station, Univ. of Florida), plasmids, cosmids, YACs (yeast artificial chromosomes), BACs (bacterial artificial chromosomes) or any other suitable cloning vector, when used with an appropriate transformation protocol, e. g., bacterial infection (e.g., with *Agrobacterium* as described above), binary bacterial artificial chromosome constructs, direct delivery of DNA (e. g., via PEG-mediated transformation, desiccation/inhibition-mediated DNA uptake, electroporation, agitation with silicon carbide fibers, and microprojectile bombardment). It would be clear to one of ordinary skill in the art that various transformation methodologies can be used and modified for production of stable transgenic plants from any number of plant species of interest.

80) Transformation methods to provide transgenic plant cells and transgenic plants containing stably integrated recombinant DNA are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos or parts of embryos, and gametic cells such as microspores, pollen, sperm, and egg cells. Any cell from which a fertile plant can be regenerated is contemplated as a useful recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (e. g., various media and recipient target cells, transformation of immature embryos, and subsequent regeneration of fertile transgenic plants) are disclosed, for example, in U.S. Pat. Nos. 6,194, 636 and 6,232,526 and U. S. Patent Application Publication 2004/0216189, which are specifically incorporated by reference.

81) In general transformation practice, DNA is introduced into only a small percentage of target cells in any one transformation experiment. Marker genes are generally used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant DNA. Commonly used selective marker genes include those conferring resistance to antibiotics such as kanamycin or paromomycin (nptII), hygromycin B (aph IV) and gentamycin (aac3 and aacC4) or resistance to herbicides such as glufosinate (bar or pat), glyphosate (EPSPS), and dicamba. Examples of useful selective marker genes and selection agents are illustrated in U.S. Pat. Nos. 5,550,318, 5,633,435, 5,780,708, and 6,118,047, all of which are specifically incorporated by reference. A particularly preferred herbicide resistance gene is a glyphosate acetyl transferase, disclosed as SEQ ID NO. 68 in U. S. Patent Application Publication 2007/0079393 A1, which is specifically incorporated by reference. Screenable markers or reporters, such as markers that provide an ability to visually identify transformants can also be employed. Non-limiting examples of useful screenable markers include, for example, a gene expressing a protein that produces a detectable color by acting on a chromogenic substrate (e. g., beta-glucuronidase (GUS) (uidA) or luciferase (luc)) or that itself is detectable, such as green fluorescent protein (GFP) (gfp) or an immunogenic molecule. Those of skill in the art will recognize that many other useful markers or reporters are available for use.

82) Detecting or measuring transcription of the recombinant DNA construct in the transgenic plant cell of the invention can be achieved by any suitable method, including protein detection methods (e. g., western blots, ELISAs, and other immunochemical methods), measurements of enzymatic activity, or nucleic acid detection methods (e. g., Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, N Y, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Peña (editor) "Transgenic Plants: Methods and Protocols", Humana Press, 2004.

83) Other suitable methods for detecting or measuring transcription of the recombinant DNA construct in the transgenic plant cell of the invention include measurement of any other trait that is a direct or proxy indication of suppression of the target gene in the transgenic plant cell in which the recombinant DNA construct is transcribed, relative to one in which the recombinant DNA is not transcribed, e. g., gross or microscopic morphological traits, growth rates, yield, reproductive or recruitment rates, resistance to pests or pathogens, or resistance to biotic or abiotic stress (e. g., water deficit stress, salt stress, nutrient stress, heat or cold stress). Such methods can use direct measurements of a phenotypic trait or proxy assays (e. g., in plants, these assays include plant part assays such as leaf or root assays to determine tolerance of abiotic stress). Non-limiting methods include direct measurements of resistance to the invertebrate pest (e. g., damage to plant tissues) or proxy assays (e. g., plant yield assays, or bioassays such as the Western corn rootworm (*Diabrotica virgifera virgifera* LeConte) larval bioassay described in International Patent Application Publication WO2005/110068 A2 and U. S. Patent Application Publication US 2006/0021087 A1, specifically incorporated by reference, or the soybean cyst nematode bioassay described by Steeves et al. (2006) *Funct. Plant Biol.*, 33:991-999, wherein cysts per plant, cysts per gram root, eggs per plant, eggs per gram root, and eggs per cyst are measured.

84) The recombinant DNA constructs of the invention can be stacked with other recombinant DNA for imparting additional traits (e. g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in U.S. Patent Application Publication 2004/0126845 A1, specifically incorporated by reference.

85) Seeds of transgenic, fertile plants can be harvested and used to grow progeny generations, including hybrid generations, of transgenic plants of this invention that include the recombinant DNA construct in their genome. Thus, in addition to direct transformation of a plant with a recombinant DNA construct of this invention, transgenic plants of the invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introgress the recombinant DNA into the resulting progeny. A transgenic plant of the invention can be crossed with a plant line having other recombinant DNA that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s).

86) Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e. g., usually 6 to 8 generations, to produce a progeny plant with substantially the same genotype as one original transgenic parental line but for the recombinant DNA of the other transgenic parental line.

87) Yet another aspect of the invention is a transgenic plant grown from the transgenic seed of the invention. This invention contemplates transgenic plants grown directly from transgenic seed containing the recombinant DNA as well as progeny generations of plants, including inbred or hybrid plant lines, made by crossing a transgenic plant grown directly from transgenic seed to a second plant not grown from the same transgenic seed.

88) Crossing can include, for example, the following steps:
    (a) plant seeds of the first parent plant (e. g., non-transgenic or a transgenic) and a second parent plant that is transgenic according to the invention;
    (b) grow the seeds of the first and second parent plants into plants that bear flowers;
    (c) pollinate a flower from the first parent with pollen from the second parent; and
    (d) harvest seeds produced on the parent plant bearing the fertilized flower.

89) It is often desirable to introgress recombinant DNA into elite varieties, e. g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i. e., one or more transformation events.

90) Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different hybrids with different combinations of DNA constructs. In this way, plants can be produced which have the desirable agronomic properties frequently associated with hybrids ("hybrid vigor"), as well as the desirable characteristics imparted by one or more DNA constructs.

91) Genetic markers can be used to assist in the introgression of one or more DNA constructs of the invention from one genetic background into another. Marker assisted selection offers advantages relative to conventional breeding in that it can be used to avoid errors caused by phenotypic variations. Further, genetic markers can provide data regarding the relative degree of elite germplasm in the individual progeny of a particular cross. For example, when a plant with a desired trait which otherwise has a non-agronomically desirable genetic background is crossed to an elite parent, genetic markers can be used to select progeny which not only possess the trait of interest, but also have a relatively large proportion of the desired germplasm. In this way, the number of generations required to introgress one or more traits into a particular genetic background is minimized. The usefulness of marker assisted selection in breeding transgenic plants of the current invention, as well as types of useful molecular markers, such as but not limited to SSRs and SNPs, are discussed in PCT Application Publication WO 02/062129 and U. S. Patent Application Publications Numbers 2002/0133852, 2003/0049612, and 2003/0005491, each of which is specifically incorporated by reference.

92) In certain transgenic plant cells and transgenic plants of the invention, it may be desirable to concurrently express (or suppress) a gene of interest while also regulating expression of a target gene. Thus, in some embodiments, the transgenic plant contains recombinant DNA including both a transgene transcription unit for expressing at least one gene of interest and a gene suppression element for suppressing a target gene.

93) Thus, as described herein, the transgenic plant cells or transgenic plants of the invention can be obtained by use of any appropriate transient or stable, integrative or non-integrative transformation method known in the art or presently disclosed. The recombinant DNA constructs can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood-, fiber-, pulp-, or cellulose-producing trees and plants, vegetable plants, fruit plants, and ornamental plants. Non-limiting examples of plants of interest include grain crop plants (such as wheat, oat, barley, maize, rye, triticale, rice, millet, sorghum, *quinoa*, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, macadamia, and the like); sugarcane, coconut, date palm, olive, sugarbeet, tea, and coffee; wood-, fiber-, pulp-, or cellulose-producing trees and plants (for example, cotton, flax, jute, ramie, sisal, kenaf, switchgrass, and bamboo); vegetable crop plants such as legumes (for example, beans, peas, lentils, alfalfa, peanut), lettuce, asparagus, artichoke, celery, carrot, radish, cassava, sweet potato, yam, cocoa, coffee, tea, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, *quinoa*, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, *papaya*, avocado, fig, mango, and berries; and ornamental plants including ornamental flowering plants, ornamental trees and shrubs, ornamental groundcovers, and ornamental grasses. Preferred dicot plants include, but are not limited to, canola, broccoli, cabbage, carrot, cauliflower, Chinese cabbage, cucumber, dry beans, eggplant, fennel, garden beans, gourds, lettuces, melons, okra, peas, peppers, pumpkin, radishes, spinach, squash, watermelon, cotton, potato, *quinoa*, amaranth, buckwheat, safflower, soybean, sugarbeet, and sunflower. Preferred monocots include, but are not limited to, wheat, oat, barley, maize (including sweet corn and other varieties), rye, triticale, rice, ornamental and forage grasses, sorghum, millet, onions, leeks, and sugarcane, more preferably maize, wheat, and rice.

94) The ultimate goal in plant transformation is to produce plants which are useful to man. In this respect, transgenic plants of the invention can be used for virtually any purpose deemed of value to the grower or to the consumer. For example, one may wish to harvest the transgenic plant itself, or harvest transgenic seed of the transgenic plant for planting purposes, or products can be made from the transgenic plant or its seed such as oil, starch, ethanol or other fermentation products, animal feed or human food, pharmaceuticals, and various industrial products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338, specifically incorporated by reference, and PCT Publications WO 95/06128 and WO 02/057471. Thus, this invention also provides commodity products produced from a transgenic plant cell, plant, or seed of this invention, including, but not limited to, harvested leaves, roots, shoots, tubers, stems, fruits, seeds, or other parts of a plant, meals, oils, extracts, fermentation or digestion products, crushed or whole grains or seeds of a plant, or any food or non-food product including such commodity products produced from a transgenic plant cell, plant, or seed of this invention. The detection of one or more of nucleic acid sequences of the recombinant DNA constructs of this invention in one or more commodity or commodity products contemplated herein is de facto evidence that the commodity or commodity product contains or is derived from a transgenic plant cell, plant, or seed of this invention.

95) In preferred embodiments, the transgenic plant prepared from the transgenic plant cell of this invention, i. e., a transgenic plant having in its genome a recombinant DNA construct of this invention has at least one additional altered trait, relative to a plant lacking the recombinant DNA construct, selected from the group of traits consisting of:

(a) improved abiotic stress tolerance;
(b) improved biotic stress tolerance;
(c) modified primary metabolite composition;
(d) modified secondary metabolite composition;
(e) modified trace element, carotenoid, or vitamin composition;
(f) improved yield;
(g) improved ability to use nitrogen or other nutrients;
(h) modified agronomic characteristics;
(i) modified growth or reproductive characteristics; and
(j) improved harvest, storage, or processing quality.

96) In particularly preferred embodiments, the transgenic plant is characterized by: improved tolerance of abiotic stress (e. g., tolerance of water deficit or drought, heat, cold, non-optimal nutrient or salt levels, non-optimal light levels) or of biotic stress (e. g., crowding, allelopathy, or wounding); by a modified primary metabolite (e. g., fatty acid, oil, amino acid, protein, sugar, or carbohydrate) composition; a modified secondary metabolite (e. g., alkaloids, terpenoids, polyketides, non-ribosomal peptides, and secondary metabolites of mixed biosynthetic origin) composition; a modified trace element (e. g., iron, zinc), carotenoid (e. g., beta-carotene, lycopene, lutein, zeaxanthin, or other carotenoids and xanthophylls), or vitamin (e. g., tocopherols) composition; improved yield (e. g., improved yield under non-stress conditions or improved yield under biotic or abiotic stress); improved ability to use nitrogen or other nutrients; modified agronomic characteristics (e. g., delayed ripening; delayed senescence; earlier or later maturity; improved shade tolerance; improved resistance to root or stalk lodging; improved resistance to "green snap" of stems; modified photoperiod response); modified growth or reproductive characteristics (e. g., intentional dwarfing; intentional male sterility, useful, e. g., in improved hybridization procedures; improved vegetative growth rate; improved germination; improved male or female fertility); improved harvest, storage, or processing quality (e. g., improved resistance to pests during storage, improved resistance to breakage, improved appeal to consumers); or any combination of these traits.

97) In one preferred embodiment, transgenic seed, or seed produced by the transgenic plant, has modified primary metabolite (e. g., fatty acid, oil, amino acid, protein, sugar, or carbohydrate) composition, a modified secondary metabolite (e. g., alkaloids, terpenoids, polyketides, non-ribosomal peptides, and secondary metabolites of mixed biosynthetic origin) composition, a modified trace element (e. g., iron, zinc, sulfur), organic phosphate (e. g, phytic acid), carotenoid (e. g., beta-carotene, lycopene, lutein, zeaxanthin, or other carotenoids and xanthophylls), or vitamin (e. g., tocopherols) composition, an improved harvest, storage, or processing quality, or a combination of these. For example, it can be desirable to modify the amino acid (e. g., lysine, methionine, tryptophan, or total protein), oil (e. g., fatty acid composition or total oil), carbohydrate (e. g., simple sugars or starches), trace element, carotenoid, or vitamin content of seeds of crop plants (e. g., canola, cotton, safflower, soybean, sugarbeet, sunflower, wheat, maize, or rice), preferably in combination with improved seed harvest, storage, or processing quality, and thus provide improved seed for use in animal feeds or human foods. In another example, it can be desirable to modify the quantity or quality of polysaccharides (e. g., starch, cellulose, or hemicellulose) in plant tissues for use in animal feeds or human foods or for fermentation or biofuel production. In another instance, it can be desirable to change levels of native components of the transgenic plant or seed of a transgenic plant, for example, to decrease levels of proteins with low levels of lysine, methionine, or tryptophan, or to increase the levels of a desired amino acid or fatty acid, or to decrease levels of an allergenic protein or glycoprotein (e. g., peanut allergens including ara h 1, wheat allergens including gliadins and glutenins, soybeanallergens including P34 allergen, globulins, glycinins, and conglycinins) or of a toxic metabolite (e. g., cyanogenic glycosides in cassava, *solanum* alkaloids in members of the Solanaceae).

Methods for Temporal Regulation of Gene Expression

98) Another aspect of this invention is a method of temporally regulating expression of a gene, including expressing in a plant the recombinant DNA construct of this invention, whereby the expression of at least one gene is modulated by part or all of a circadian miRNA gene of the plant, resulting in temporally specific expression of the at least one gene. The at least one gene is at least one selected from a gene endogenous to the plant, a transgene in the plant, and a gene endogenous to a pest or pathogen of the plant. The at least one gene is at least one selected from coding DNA and non-coding DNA. Non-limiting embodiments of the method include those wherein the circadian miRNA gene encodes a mature miRNA selected from the group consisting of a miR390, TAS3 ta-siRNAs, miR393, mir156, mir159, and miRMON1 (as described in the Examples).

99) In one embodiment of the method, the recombinant DNA construct includes (a) DNA encoding an exogenous miRNA recognition site that is recognizable by a mature miRNA natively transcribed from the circadian miRNA gene of the plant, and (b) DNA encoding the at least one gene; and the expression of at least one gene is decreased during time periods when the mature miRNA is transcribed relative to expression during time periods when the mature miRNA is not transcribed. In a non-limiting example, the recombinant DNA construct includes (a) DNA encoding an exogenous miRNA recognition site that is recognizable by Gm-miR-MON1 (SEQ ID NO. 1), and (b) DNA encoding the at least one gene; and the expression of at least one gene is substantially decreased at night relative to expression during the day.

100) In another embodiment of the method, the recombinant DNA construct includes a promoter of a circadian miRNA gene of the plant, operably linked to DNA encoding the at least one gene. In non-limiting examples, the promoter is a promoter of a circadian miRNA gene encoding a mature miRNA selected from the group consisting of a miR390, TAS3 ta-siRNAs, miR393, mir156, mir159, and miRMON1. In a specific, non-limiting example, the promoter includes SEQ ID NO. 30, or includes at least 100 contiguous nucleotides having at least 95% sequence identity to a fragment of at least 100 contiguous nucleotides from nucleotides 1-394 of SEQ ID NO. 30, and exhibits circadian promoter activity in a plant, and the expression of at least one gene is substantially nocturnal.

101) In another embodiment, the recombinant DNA construct encodes a transgene that is derived from a gene natively under the control of an endogenous circadian plant miRNA gene (i. e., a gene that natively includes in its transcript a miRNA recognition site that is recognized by an endogenous mature miRNA natively transcribed from a circadian plant miRNA gene), but that is engineered to lack that miRNA recognition site. This method permits expression of the engineered transgene free of control by the endogenous circadian plant miRNA (for example, free of control by an endogenous miR390, TAS3 ta-siRNAs, miR393, mir156, mir159, and miRMON1). In a further embodiment, the recombinant DNA construct is designed to suppress the endogenous circadian plant miRNA gene that natively causes circadian expression of the gene. Yet another embodiment of the method includes transcription of a recombinant DNA construct for expression of an endogenous circadian plant miRNA precursor under the control of a promoter other than its endogenous promoter. The mature miRNA (either as a native sequence or modified) is transcribed from the miRNA precursor in an expression pattern different from its native expression pattern; for example, a mature miRNA that is natively nocturnally expressed can be expressed under the control of a promoter having a different expression pattern, e. g., a constitutive or diurnal or inducible promoter. This method is useful for suppressing expression of endogenous genes natively containing recognition sites for the mature miRNA in an expression pattern different from the native pattern.

EXAMPLES

102) The entire disclosure, and especially the working Examples of U.S. patent application Ser. No. 11/303,745 and the sequence listing contained in the file named "38-15 (53429) C.rpt", filed by amendment on 29 Sep. 2006 as a replacement sequence listing for application Ser. No. 11/303,745, are specifically incorporated by reference in their entirety herein.

Example 1

103) This example describes non-limiting embodiments of a recombinant DNA construct transcribable in a plant cell for temporally specific expression of at least one gene, wherein the expression of at least one gene is modulated by part or all of a circadian plant miRNA gene. More particularly, this example describes a non-limiting procedure for identifying circadian plant miRNA genes useful in making the recombinant DNA constructs and non-natural transgenic plant cells, plants, and seeds of this invention.

104) Novel miRNAs were cloned by high-throughput sequencing (Margulies et al. (2005) *Nature*, 437:376-380) of a size-fractionized cDNA library constructed from soybean leaves, and the corresponding MIR sequences were identified. Criteria for miRNA identification included: (1) a cloned 21-nt small RNA, and possible miRNA* (strand corresponding to the miRNA) at a lower abundance, (2) containment of the miRNA/miRNA* duplex wholly within a short, imperfect foldback structure, (3) derivation of the miRNA from an RNA Pol II non-protein-coding transcript, and (4) presence of a complementary target site in a coding gene (Ambros et al. (2003) *RNA*, 9: 277-279).

105) Small RNAs were extracted from adaptor-containing raw sequences and their strands were determined. This sequence set was filtered to remove small RNA sequences that were virus, tRNA, rRNA, chloroplast and mitochondria RNAs, and transgene, resulting in a filtered set of 381,633 putative miRNA sequences. Small RNAs not originating from the above sources and not homologous to known miRNAs were mapped to reference soybean cDNA sequences. For the mapped cDNA sequences with low protein-coding content, a cDNA sequence fragment of about 250 nucleotides, containing the putative miRNA, was predicted by an algorithm ("RNAFolder", based on RNAfold, publicly available at www(dot)tbi(dot)univie(dot)ac(dot)at/~ivo/RNA/RNAfold(dot)html). The foldback structure was examined to check if the small RNA was located in the stem, and if an extensively (but not perfectly) complementary small RNA with lower abundance was located in the opposite side of the stem. Potential targets of the small RNA were predicted based on rules modified from Jones-Rhoades and Bartel (2004)*Mol. Cell*, 14:787-799, and Zhang (2005) *Nucleic Acids Res.*, 33:W701-704. Among the novel mature miRNAs identified, was a 21-mer assigned the trivial name "Gm-miRMON1", with the nucleotide sequence UGAGACCAAAUGAGCAGCUGA (SEQ ID NO. 1).

Figure 1:
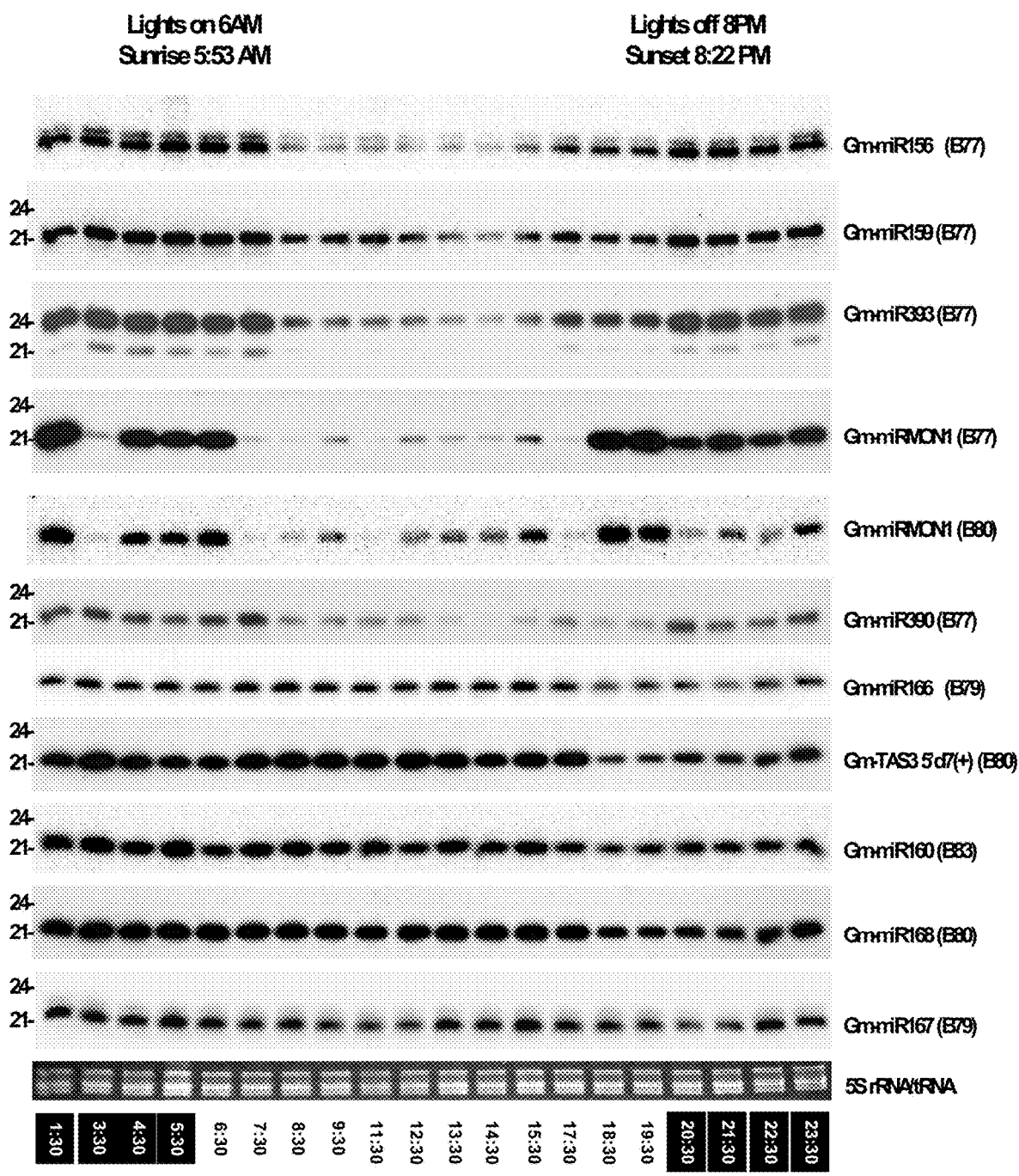
FIG. 1 depicts expression profiles of soybean miR-NAs in trifoliate leaves, analyzed by Northern blots of samples taken over a single day/night cycle (an artificial light/dark cycle over 24 hours), as described in Example 1. Blot numbers are indicated in parentheses next to the miRNA name. 5S rRNA and tRNA are shown as loading controls.

106) The expression profile of soybean miRNAs in trifoliate leaves was analyzed by Northern blots of samples taken over a single day/night cycle (an artificial light/dark cycle over 24 hours), as depicted in FIG. 1. Gm-miRMON1 (SEQ ID NO. 1) exhibits substantially nocturnal expression that did not appear to be substantially light-suppressed, as an increase in transcript abundance was observed at least 1.5 hours prior to the lights being turned off, and furthermore a decrease in transcript abundance did not occur for at least a half-hour after lights are turned on. Gm-miR393 (SEQ ID NO. 2) similarly exhibited substantially nocturnal expression that did not appear to be substantially light-suppressed, as an increase in transcript abundance was observed at least 2.5 hours prior to the lights being turned off, and furthermore a decrease in transcript abundance did not occur for at least 1.5 hours after lights are turned on. Gm-miR159 (SEQ ID NO. 3), Gm-miR390 (SEQ ID NO. 4), and Gm-miR156 (SEQ ID NO. 5) also exhibited substantially nocturnal expression. The expression of Gm-TAS3 (SEQ ID NO. 6) (ta-siRNAs) was diurnally increased.

107) Table 1 provides non-limiting examples of circadian plant miRNAs (mature miRNA sequences and miRNA precursors) useful in this invention.

TABLE 1

| miRNA | mature miRNA | precursors |
|---|---|---|
| Gm-miRMON1 | UGAGACCAAAUGAGCAGCUGA (SEQ ID NO. 1) | SEQ ID NO. 7 |
| Gm-miR393 | UCCAAAGGGAUCGCAUUGAUC (SEQ ID NO. 2) | miR393a (SEQ ID NO. 8); miR393b (SEQ ID NO. 9) |
| Gm-miR159 | UUUGGAUUGAAGGGAGCUCUA (SEQ ID NO. 3) | SEQ ID NO. 10 |
| Gm-miR390 | AAGCUCAGGAGGGAUAGCGCC (SEQ ID NO. 4) | SEQ ID NO. 11; SEQ ID NO. 12 |
| Gm-miR156 | UGACAGAAGAGAGUGAGCAC (SEQ ID NO. 5) | Gm-miR156a (SEQ ID NO. 13); Gm-miR156b (SEQ ID NO. 14); Gm-miR156c (SEQ ID NO. 15); Gm-miR156d (SEQ ID NO. 16); Gm-miR156e (SEQ ID NO. 17) |
| Gm-TAS3 5'D7(+) | UUCUUGACCUUGUAAGGCCUU (SEQ ID NO. 6) | SEQ ID NO. 18 |

108) The foldback structure of the miRNA precursor (SEQ ID NO. 7) of Gm-miRMON1 (SEQ ID NO. 1) was predicted using the program EINVERTED (Rice et al. (2000) *Trends Genet.*, 16:276-277) and is depicted in FIG. 2. A maize miR393 mature miRNA was similarly identified as Zm-miR393 (SEQ ID NO. 19), having the sequence UCCAAAGGGAUCGCAUUGAUCU, which was identical to that of the soybean miR393 (SEQ ID NO. 2) except for one additional nucleotide.

109) Any of the circadian plant miRNAs disclosed herein is also useful as a starting or scaffold sequence for use in designing novel engineered miRNAs for silencing a target gene, e. g., wherein the starting miRNA precursor is modified to yield engineered miRNA precursors that are processed to engineered mature miRNAs designed to silence a specific target gene or genes. Designing an engineered miRNA sequence can be as simple as substituting sequence that is complementary to the intended target for nucleotides in the miRNA stem region of the miRNA precursor, as demonstrated by Zeng et al. (2002) *Mol. Cell*, 9:1327-1333. One non-limiting example of a general method for determining nucleotide changes in a native miRNA sequence to produce the engineered miRNA precursor includes the following steps:
  (a) Selecting a unique target sequence of at least 18 nucleotides specific to the target gene, e. g., by using sequence alignment tools such as BLAST (see, for example, Altschul et al. (1990) *J Mol. Biol.*, 215:403-410; Altschul et al. (1997) *Nucleic Acids Res.*, 25:3389-3402), for example, of both maize cDNA and genomic DNA databases, to identify target transcript orthologues and any potential matches to unrelated genes, thereby avoiding unintentional silencing of non-target sequences.

(b) Analyzing the target gene for undesirable sequences (e. g., matches to sequences from non-target species), and score each potential 19-mer segment for GC content, Reynolds score (see Reynolds et al. (2004) *Nature Biotechnol.*, 22:326-330), and functional asymmetry characterized by a negative difference in free energy ("ΔΔG") (see Khvorova et al. (2003) *Cell*, 115:209-216). Preferably 19-mers are selected that have all or most of the following characteristics: (1) a Reynolds score >4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. Preferably multiple (3 or more) 19-mers are selected for testing. Positions at every third nucleotide in an siRNA have been reported to be especially important in influencing RNAi efficacy and an algorithm, "siExplorer" is publicly available at ma.chem.t.u-tokyo.ac.jp/siexplorer.htm (see Katoh and Suzuki (2007) *Nucleic Acids Res.*, 10.1093/nar/gkl1120).

(c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent transitive spreading of silencing on the target transcript or paired to the target sequence to promote transitive spreading of silencing on the target transcript.

(d) Testing the engineered miRNA precursor, for desirable characteristics, such as in planta expression levels of the miRNA precursor or of the mature miRNA (for example, in a transient *Nicotiana benthamiana* assay for miRNA expression and target repression) or efficacy in suppressing the target gene (which can be done using various direct or proxy assays as are known in the art, for example those described under the heading "Making and Using Transgenic Plant Cells and Transgenic Plants").

and (e) Cloning the most effective engineered miRNA precursor into a construct for stable transformation of a plant, e. g., maize (see the sections under the headings "Making and Using Recombinant DNA Constructs" and "Making and Using Transgenic Plant Cells and Transgenic Plants").

110) Recognition sites useful in recombinant DNA constructs of this invention can be designed for recognition by any of the circadian plant miRNAs disclosed herein, with a non-limiting example presented in Example 3. Recognition sites are preferably designed following the sequence requirements for mature miRNA binding to a recognition site, described in Llave et al. (2002) *Science*, 297:2053-2056, Rhoades et al. (2002) *Cell*, 110:513-520, Jones-Rhoades and Bartel (2004) *Mol. Cell*, 14:787-799, Schwab et al (2005) *Developmental Cell*, 8:517-527, and Xie et al. (2005) *Plant Physiol.*, 138:2145-2154. In preferred embodiments, the miRNA recognition site has high sequence complementarity to the intended circadian plant miRNA, e. g., perfect complementarity between 19, 20, or 21 out of 21 nucleotides (in the case of a mature miRNA that is 21 nucleotides in length), that is, complementarity of about 90% or greater.

Example 2

111) This example describes non-limiting embodiments of a recombinant DNA construct transcribable in a plant cell for temporally specific expression of at least one gene, wherein the expression of at least one gene is modulated by part or all of a circadian plant miRNA gene. More particularly, this example describes transcription profiling as another procedure for identifying circadian plant miRNA genes useful in making the recombinant DNA constructs and non-natural transgenic plant cells, plants, and seeds of this invention.

112) Transcription profiling was used to identify a circadian expression pattern exhibited by the mature soybean miRNA Gm-miR156, UGACAGAAGAGAGUGAGCAC (SEQ ID NO. 5). Gm-miR156 transcript accumulation in soybean V3 leaf was measured at 12 time points over a 24-hour period and was found exhibit substantially nocturnal expression, with transcript levels at 5 and 8 hours after sunset observed to be about 3-fold higher than levels during daytime hours. Precursors identified for this miRNA included Gm-miR156a (SEQ ID NO. 13), Gm-miR156b (SEQ ID NO. 14), Gm-miR156c (SEQ ID NO. 15), Gm-miR156d (SEQ ID NO. 16), and Gm-miR156e (SEQ ID NO. 17).

Example 3

113) This example describes non-limiting embodiments of a recombinant DNA construct transcribable in a plant cell for temporally specific expression of at least one gene, wherein the expression of at least one gene is modulated by part or all of a circadian plant miRNA gene. This example describes a recombinant DNA construct including (a) DNA encoding an exogenous miRNA recognition site that is recognizable by a mature miRNA natively transcribed from the circadian plant miRNA gene, and (b) DNA encoding the at least one gene; and the expression of at least one gene is decreased during time periods when the mature miRNA is transcribed relative to expression during time periods when the mature miRNA is not transcribed.

114) The soybean miRNA Gm-miRMON1, UGAGACCAAAUGAGCAGCUGA (SEQ ID NO. 1) was found to exhibit substantially nocturnal expression that did not appear to be substantially light-suppressed (see Example 1). Recognition sites are designed as described in Example 1. Examples of recognition sites recognized by the mature Gm-miRMON1 miRNA (SEQ ID NO. 1) natively transcribed from the endogenous miRNA gene, are provided in Table 2 and are useful in making recombinant DNA constructs of this invention.

TABLE 2

| Recognition sites for Gm-miRMON1 | Score | Mismatches |
|---|---|---|
| UCAGCUGCUCAUCUGUUCUCA (SEQ ID NO. 20) | 2.5 | 2 |
| CCAGCUGCUCAUUUGGUCACU (SEQ ID NO. 21) | 2.5 | 3 |
| UCAGCUCUUCUUUUGGUCUCU (SEQ ID NO. 22) | 2.5 | 4 |
| UCAGCUACUGAUCUGGUCUCA (SEQ ID NO. 23) | 3 | 3 |

TABLE 2-continued

| Recognition sites for Gm-miRMON1 | Score | Mismatches |
|---|---|---|
| UCAGCUGUUCCUUUGUUCUCU (SEQ ID NO. 24) | 3 | 4 |
| UCAGCUGUUCCUUUGUUCUCU (SEQ ID NO. 25) | 3 | 4 |
| GUAGCUUCUCACUUGGUCUUA (SEQ ID NO. 26) | 3 | 5 |
| UUAGCUGCUUCUUCGGUCUCU (SEQ ID NO. 27) | 3 | 5 |
| UUAGAUGCUUGUUUGGUCUUU (SEQ ID NO. 28) | 3 | 6 |

Figure 3:
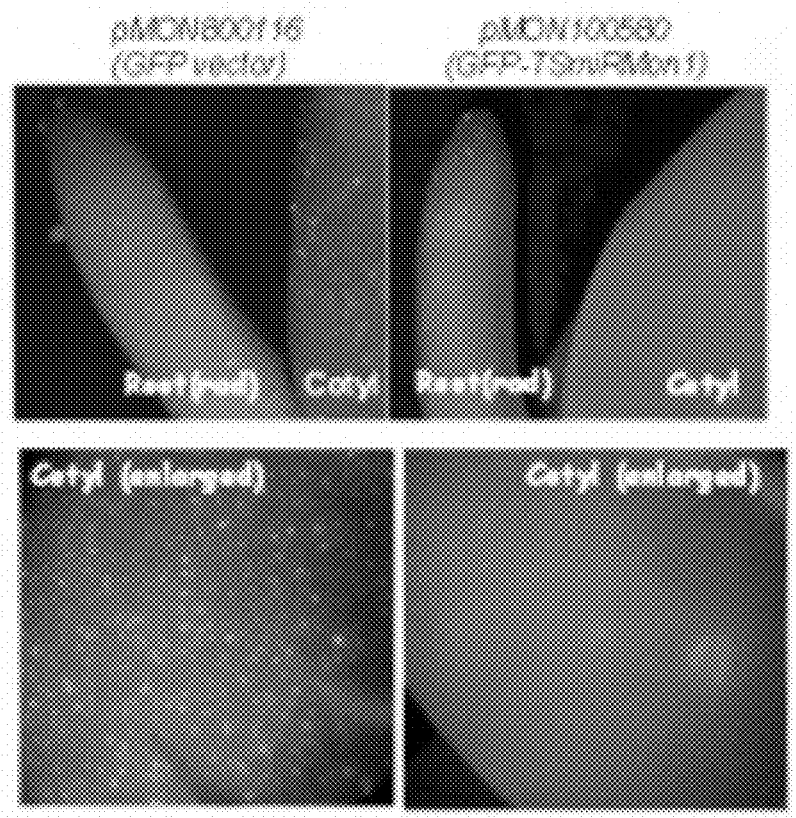
FIG. 3 depicts results of a transient assay useful in assessing spatial or temporal expression of a construct including DNA encoding a gene to be expressed (GFP), as described in Example 3. When the construct lacked an exogenous Gm-miRMON1 recognition site, GFP expression was observed in embryonic root or radicle ("rad") and embryonic leaf cotyledon ("cotyl"); when an exogenous Gm-miRMON1 recognition site was included in the construct, GFP expression was suppressed in the cotyledon.

115) In a non-limiting example, a recombinant DNA construct ("pMON100580") was designed to include DNA encoding an exogenous Gm-miRMON1 recognition site (SEQ ID NO. 20; alternatively any of those provided in Table 2) and DNA encoding green fluorescent protein (GFP); the miRNA recognition site was located in the 3' untranslated region of the GFP transcript. A control construct ("pMON800116") similarly encoded the GFP sequence but lacked an exogenous Gm-miRMON1 recognition site. These constructs were introduced into soybean embryos by microprojectile bombardment, and the resulting transient GFP expression was observed, as depicted in FIG. 3. With pMON800116, translation of GFP was observed in both the radicle (embryonic root) and cotyledon (embryonic leaf). With pMON100580, GFP translation (expression) was observed only in the radicle, where Gm-miRMON1, and not in the cotyledon. Gm-miRMON1 expression is thus both circadian (see Example 1) and tissue-specific. Translation of GFP is thus decreased where the mature Gm-miRMON1 miRNA is transcribed, in a spatially specific and temporally specific manner.

Figure 4:
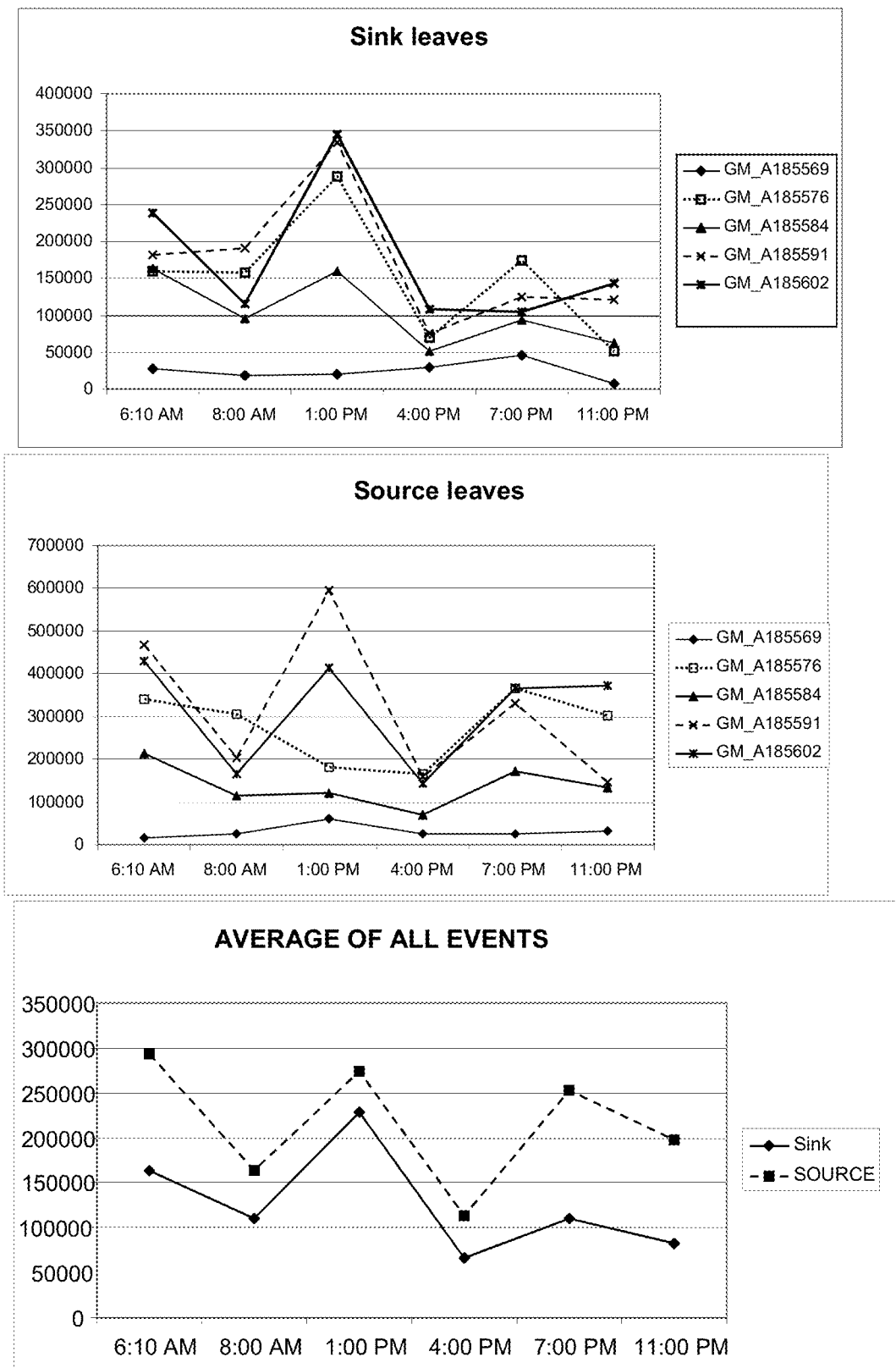
FIG. 4 depicts mRNA levels of GUS expressed in transgenic soybean plants having in their genome a recombinant DNA construct including DNA encoding GUS and an exogenous Gm-miRMON1 recognition site, as described in Example 3.

116) In another non-limiting example, a recombinant DNA construct ("pMON100571") including DNA encoding GUS and an exogenous miRNA recognition site (SEQ ID NO. 20; alternatively any of those provided in Table 2) recognizable by the endogenous mature Gm-miRMON1 (SEQ ID NO. 1) was transformed into soybean (*Glycine max*). Three samples each of "sink" (young/developing) and of "source" (mature) leaves from each of 5 separate transformation events (RO plants) were taken during six time points (6 a.m., 8 a.m., 1 p.m., 4 p.m., 7 p.m., and 11 p.m.) over a 24-hour period and GUS mRNA levels were determined by Invader assay. The results are depicted in FIG. 4. On average, GUS mRNA levels were observed to be highest during the day, when levels of Gm-miRMON1 mature miRNA are lowest.

Example 4

117) This example describes non-limiting embodiments of a recombinant DNA construct transcribable in a plant cell for temporally specific expression of at least one gene, wherein the expression of at least one gene is modulated by part or all of a circadian plant miRNA gene, where the construct includes a promoter of a circadian plant miRNA gene operably linked to DNA encoding the at least one gene. More particularly, this example describes identification of a promoter of the soybean leaf circadian miRNA gene, Gm-MIRMON1, and a recombinant DNA construct including this promoter operably linked to a transgene transcription unit for expressing coding DNA. In analogous constructs, the promoter of a circadian plant miRNA gene is operably linked to a non-coding gene suppression element, or both a non-coding gene suppression element and coding DNA.

118) Genomic DNA was isolated from soybean leaves and miRNA flanking sequence was obtained by inverse PCR amplification and cloning of circularized restriction enzyme fragments. To make inverse PCR libraries, 10 micrograms genomic DNA was digested separately with NotI, XhoI, HindIII, PstI, BamHI, and SpeI, followed by self-ligation. The genomic flanking regions were sequenced using primers complementary to regions of the known Gm-miRMON1 miRNA sequence. PCR-amplified products were cloned and sequenced using the pCR2.1 Topo TA cloning vector (Invitrogen, Carlsbad, Calif.) and M13F and M13R vector primers. The transcription start site (TSS) was obtained using soybean genomic leaf RNA and the GeneRacer Kit (Invitrogen, Carlsbad, Calif.), according to the manufacturer's instructions; the position of the TSS is shown in underlined font in the following sequence, which also includes Gm-miRMON1 precursor sequence including DNA encoding the mature Gm-miRMON1 miRNA (shown in italicized font in the following sequence):

```
                                          (SEQ ID NO. 29)
CTGCAGCTGATCCACTCTTGCATTAAGAAGACACGCTATTAACTTTTCTT

TTATCAAATTAATTATACATGTCTCTTTATAAGTTTTTTTTTCTTTTGA

TATATATTTATTAAATTCTACCTGAATCAATTATGTATATAATGTTTATA

ATTTTAAATATTTTTTTTTCTTTCTAGGTTATATTTTTTAATTTAAAA

TATTGACGAAGTCAACAATATTTGTGTTTTGCATTGACGTGCTGGCAACG

GGAAGTTGTACTATATACATAGCGTCTTAGATTTGTGTTCAAATCGGTAG

TACAAAGTACTAGTACTACATGTACATCTAACCTAGAAGAAGTACCACGC

TTGCTTGAGGCTATATATCCACTGAATCAAGTTGGATAAACATAAACTCA

TTACATTGATAAAACACAATTCAAAAGATCAATGTTCCACTTCATGCAAA

GACATTTCCAAAATATGTGTAGGTAGAGGGGTTTACAGGATCGTCCTGA

GACCAAATGAGCAGCTGACCACATGATGCAGCTATGTTTGCTATTCAGCT

GCTCATCTGTTCTCAGGTCGCCCTTGTTGGACTGTCCAACTCCTACTGAT

TGCGGATGCACTTGCCACAAATGAAAATCAAAGCGAGGGGAAAAGAATGT

AGAGTGTGACTACGATTGCATGCATGTGATTTAGGTAATTAAGTTACATG

ATTGTCTAATTGTGTTTATGGAATTGTATATTTTCAGACCAGGCACCTGT

GACTAATTATAGGTACCATACCTTAAAATAAGTCCAACTAAGTCCATGTC

TGTGATTTTTTAGTGTCACAAATCACAATCCATTGCCATtGGTTTTTtAA

TTTTTCATTGTCTGTTGTTTAACTAACTCTAGCTTTTTAGCTGCTTCAAG

TACAGATTCCTCAAAGTGGAAAATGTTCTTTGAAGTCAATAAAAAGAGCT

TTGATGATCATCTGCATTGTCTAAGTTGGATAAACTAATTAGAGAGAACT

TTTGAACTTTGTCTACCAAATATCTGTCAGTGTCATCTGTCAGTTCTGCA

AGCTGAAGTGTTGAATCCACGAGGTGCTTGTTGCAAAGTTGTGATATTAA

AAGACATCTACGAAGAAGTTCAAGCAAAACTCTTTTTGGCATACTTGCTG

CTGCAGAAGGAACAACTTTACCAAAAAAATTTGTTTTAAAAAAATGCTAT

GATAACAATAATGAAGAAACTAAGCATGCAAAACTGCAAAGTTGTGCTA
```

-continued

```
TAAAAAAAATCCAAACCAAAATGAAGGACAAAAGAATTTGAAACTCAATA

TCCTTTTACACAGATTATTTCACAAATCACAATTAAGTAGCAACTTGCAA

CAGATTAAAATATATTATTTTAACAAAaTATGAAACAAGGATATTTTCAT

ACACAGTGAGCACAGTGAGCGTGCTGCACTGCACTTGGAGTTGAGGAGAG

TCAGTTCAGTTCAGTGAAAGAGAAGATGGAATTTTTtGTTtGGGGAGAGC

CACAACAAAAACAGAGGATCAGTTCAGTGGATTTTTTTATTTTTATTTT

TGACAAAAATAGGCTATGCACTAGT
```

119) Gm-miRMON1 promoter sequence was identified, including the following sequence, which contained a TATA box (shown here in underlined font) located about 33 nucleotides upstream (5' from) the TSS (shown as the 3'-most nucleotide, in italicized font):

(SEQ ID NO. 30)
```
CTGCAGCTGATCCACTCTTGCATTAAGAAGACACGCTATTAACTTTTCTT

TTATCAAATTAATTATACATGTCTCTTTATAAGTTTTTTTTTCTTTTGA

TATATATTTATTAAATTCTACCTGAATCAATTATGTATATAATGTTTATA

ATTTTAAATATTTTTTTTTCTTTCTAGGTTATATTTTTTAATTTAAAA

TATTGACGAAGTCAACAATATTTGTGTTTTGCATTGACGTGCTGGCAACG

GGAAGTTGTACTATATACATAGCGTCTTAGATTTGTGTTCAAATCGGTAG

TACAAAGTACTAGTACTACATGTACATCTAACCTAGAAGAAGTACCACGC

TTGCTTGAGGCTATATATCCACTGAATCAAGTTGGATAAACATA.
```

120) Additional sequencing from soybean led to the identification of an alternative Gm-miRMON1A sequence as follows: Gm-miRMON1A promoter (up to the transcription start site) with the sequence (SEQ ID NO. 31)
```
CATAAACATGTGAAGATCATCAGTATGTGTCAACTAAATT

AAAAAAAAAATGAAAATAGAGAAGATGCCTCCAAAAGTGA

CAATTATTGGATTAATTAACAAAAAGGGAAGGTTTGAAAG

CTTTGTGGTTTTGTTAGTTAATGGTTCTGTAAATTGAAGA

ACAGAAACTGTGTTTCTTAAATGTTCTTTGGAAGTTGAGG

AGTTTTTAAGAGCAGCAACTGTACTTTCAATGGATGGCAT

AAACAGTCTTTACAAAAAAAGTGGTTTGTATAACCATCA

ACTTAATGCATAAAAAGCTTTCCTTTGAAGTTTATTAGCC

CCAAAATATTTTGTGTACCTCAGGCACGTTAATTTGCTT

CAGTATAGTATTTGTAAACACAAACATAATTCTACTGAAG

TCGGCTTCATATTATTTTTAAATTTTCCAATTAAAAATA

GCAAAACTATGAATTTGAAAGAGATATATATGATATGTT

ATGATGGGGTGATCAAATCAATCGTCTGCTATGAAAGTT

ATACGTCTAATTCTTTTTTTCTTTGTAATAAAAAATTAA

CTTACGAACTAAAAGAATAAAGATTAGCAATAGTTTACAA

AAAGTTGAGAGACTTGATTTTTACTTTGATATAATGAAAT

TTTGAATAATATAATATGTTCGATCTTTTTTCTTTATGTA

AGCATATGATTTCATTTCATCATTGCTTAGCACTTTTTGT

ATTTTTAAAAAATTCTCAAATCATTAATTATTTTAAATTT

TGTATTTTTTTTAAATCTCAGTTACTTGCACTAAAATAAT

TATATGTTGGTCCCTTTTTACATTAAATTTCTTTTTCTTTC

CCCAAACTTTAACTACTTAAATTCTCAAATTAATTATTTTT

AATAAAAAATTACTTTCTCAAATCTAAGCTGATCCACTCTT

ACATTAAGAAGACACGCTATTAACTTTTCTTTTATCAAATT

AATTATACATGTCTCTTTATAAGTTTTTTTTTCTTTTGAT

ATATATTTATTAAATTCTACCTGAATCAATTATGTATATAA

TGTTTATAATTTTAAATATTTTTTTTTCTTTCTAGGTTAT

ATTTTTTAATTTAAAATATTGACGAAGTCAACAATATTTG

TGTTTTGCATTGACGTGCTGGCAACGGGAAGTTGTACTATA

TACATAGCGTCTTAGATTTGTGTTCAAATCGGTAGTACAAA

GTACTAGTACTACATGTACATCTAACCTAGAAGAAGTACCA

CGCTTGCTTGAGGCTATATATCCACTGAATCAAGTTGGATA

AACAT,
```

5' leader from the transcription start site to the fold-back region of the miRNA primary transcript with the sequence AAACTCATTACATTGATAAAACACAATTCAAΔΔ GATCAATGTTCCACTTCATGCAAA GACATTTC-CAAAATATGTG (SEQ ID NO. 32), Gm-miRMON1A sequence (including the fold-back region, with the nucleotides encoding the mature miRMON1A 21-mer shown as underlined text), (SEQ ID NO. 33)
```
TAGGTAGAGGGGTTTTACAGGATCGTCCTGAGACCAAATGAGCAGCTGAC

CACATGATGCAGCTATGTTTGCTATTCAGCTGCTCATCTGTTCTCAGGTC

GCCCTTGTTGGACTGTCCAACTCCTACTGATTGCGGATGCACTTGCCACA

AATGAAAATCAAAGCGAGGGGAAAAGAATGTAGAGTGTGACTACGATTGC

ATGCATGTGATTTAGGTAATTAAGTTACATGATTGTCTAATTGTGTTTAT

GGAATTGTATATTTTCAGACCAGGCACCTGTGACTAATTATAGGTACCAT

ACCTTAAAATAAGTCCAACTAAGTCCATGTCTGTGATTTTTTAGTGTCAC

AAATCACAATCCATTGCCATTGGTTTTTTAATTTTTCATTGTCTGTTGTT

TAACTAACTCTAGCTTTTTAGCTGCTTCAAGTACAGATTCCTCAAAGTGG

AAAATGTTCTTTGAAGTCAATAAAAAGAGCTTTGATGATCATCTGCATTG

TCTAAGTTGGATAAACTAATTAGAGAGAACTTTTGAACTTTGTCTACCAA

ATATCTGTCAGTGTCATCTGTCAGTTCTGCAAGCTGAAGTGTTGAATCCA

CGAGGTGCTTGTTGCAAAGTTGTGATATTAAAAGACATCTACGAAGAAGT

TCAAGCAAAACTCTTTTTGGCATACTTGCTGCTGCAGAAGGAACAACTTT

ACCAAAAAATTTGTTTTAAAAAAATGCTATGATAACAATAATGAAGAAA

CTAAGCATGCAAAACTGCAAAAGTTGTGCTATAAAAAAAATCCAAACCAA

AATGAAGGACAAAAGAATTTGAAACTCAATATCCTTTTACACAGATTATT

TCACAAATCACAATTAAGTAGCAACTTGCAACAGATTAAAATATATTATT
```

-continued
TTAACAAAATATGAAACAAGGATATTTTCATACACAGTGAGCACAGTGAG

CGTGCTGCACTGCACTTGGAGTTGAGGAGAGTCAGTTCAGTTCAGTGAAA

GAGAAGATGGAATTTTTTGTTTGGGGAGAGCCACAACAAAAACAGAGGAT

CAGTTCAGTGGATTTTTTTATTTTTTATTTTTGACAAAAATAGGCTATGC

ACTAG;

the promoter, leader, and Gm-miRMON1A sequences were assembled to give the Gm-miRMON1A sequence (SEQ ID NO. 34)
CATAAACATGTGAAGATCATCAGTATGTGTCAACTAAATTAA

AAAAAAAATGAAAATAGAGAAGATGCCTCCAAAAGTGACAAT

TATTGGATTAATTAACAAAAAGGGAAGGTTTGAAAGCTTTGT

GGTTTTGTTAGTTAATGGTTCTGTAAATTGAAGAACAGAAAC

TGTGTTTCTTAAATGTTCTTTGGAAGTTGAGGAGTTTTTAAG

AGCAGCAACTGTACTTTCAATGGATGGCATAAACAGTCTTTA

CAAAAAAAAGTGGTTTGTATAACCATCAACTTAATGCATAAA

AAGCTTTCCTTTGAAGTTTATTAGCCCCAAAATATTTTGTG

TACCTCAGGCACGTTAATTTGCTTCAGTATAGTATTTGTAAA

CACAAACATAATTCTACTGAAGTCGGCTTCATATTATTTTTT

AAATTTTCCAATTAAAAATACAAAAACTGATGAATTTGAAAG

AGATATATATGATATGTTATGATGGGGGTGATCAAATCAATC

GTCTGCTATGAAAGTTATACGTCTAATTCTTTTTTTTCTTTG

TAATAAAAAATTAACTTACGAACTAAAAGAATAAAGATTAGC

AATAGTTTACAAAAGTTGAGAGACTTGAATTTTTACTTTGAT

ATAATGAAATTTTGAATAATATAATATGTTCGATCTTTTTTC

TTTATGTAAGCATATGATTTCATTTCATCATTGCTTAGCACT

TTTTGTATTTTTAAAAAATTCTCAAATCATTAATTATTTTAA

ATTTTGTATTTTTTTTAAATCTCAGTTACTTGCACTAAAAT

AATTATATGTTGGTCCCTTTTTACATTAAATTTCTTTTTCTT

TCCCCAAACTTTAACTACTTAAATTCTCAAATTAATTATTTT

TAATAAAAAATTACTTTCTCAAATCTAAGCTGATCCACTCTT

ACATTAAGAAGACACGCTATTAACTTTTCTTTTATCAAATTA

ATTATACATGTCTCTTTATAAGTTTTTTTTTCTTTTGATAT

ATATTTATTAAATTCTACCTGAATCAATTATGTATATAATGT

TTATAATTTTAAATATTTTTTTTTCTTTCTAGGTTATATTTT

TTTTAATTTAAAATATTGACGAAGTCAACAATATTTGTGTTT

TGCATTGACGTGCTGGCAACGGGAAGTTGTACTATATACATA

GCGTCTTAGATTTGTGTTCAAATCGGTAGTACAAAGTACTAG

TACTACATGTACATCTAACCTAGAAGAAGTACCACGCTTGCT

TGAGGCTATATATCCACTGAATCAAGTTGGATAAACATAAAC

TCATTACATTGATAAAACACAATTCAAAAGATCAATGTTCCA

CTTCATGCAAAGACATTTCCAAAATATGTGTAGGTAGAGGGG

TTTTACAGGATCGTCCTGAGACCAAATGAGCAGCTGACCACA

TGATGCAGCTATGTTTGCTATTCAGCTGCTCATCTGTTCTCA

GGTCGCCCTTGTTGGACTGTCCAACTCCTACTGATTGCGGAT

GCACTTGCCACAAATGAAAATCAAAGCGAGGGGAAAAGAATG

TAGAGTGTGACTACGATTGCATGCATGTGATTTAGGTAATTA

AGTTACATGATTGTCTAATTGTGTTTATGGAATTGTATATTT

TCAGACCAGGCACCTGTGACTAATTATAGGTACCATACCTTA

AAATAAGTCCAACTAAGTCCATGTCTGTGATTTTTTAGTGTC

ACAAATCACAATCCATTGCCATTGGTTTTTTAATTTTTCATT

GTCTGTTGTTTAACTAACTCTAGCTTTTTAGCTGCTTCAAGT

ACAGATTCCTCAAAGTGGAAAATGTTCTTTGAAGTCAATAAA

AAGAGCTTTGATGATCATCTGCATTGTCTAAGTTGGATAAAC

TAATTAGAGAGAACTTTTGAACTTTGTCTACCAAATATCTGT

CAGTGTCATCTGTCAGTTCTGCAAGCTGAAGTGTTGAATCCA

CGAGGTGCTTGTTGCAAAGTTGTGATATTAAAAGACATCTAC

GAAGAAGTTCAAGCAAAACTCTTTTTGGCATACTTGCTGCTG

CAGAAGGAACAACTTTACCAAAAAAATTTGTTTTAAAAAAAT

GCTATGATAACAATAATGAAGAAACTAAGCATGCAAAACTGC

AAAAGTTGTGCTATAAAAAAAATCCAAACCAAAATGAAGGAC

AAAAGAATTTGAAACTCAATATCCTTTTACACAGATTATTTC

ACAAATCACAATTAAGTAGCAACTTGCAACAGATTAAAATAT

ATTATTTTAACAAAATATGAAACAAGGATATTTTCATACACA

GTGAGCACAGTGAGCGTGCTGCACTGCACTTGGAGTTGAGGA

GAGTCAGTTCAGTTCAGTGAAAGAGAAGATGGAATTTTTTGT

TTGGGGAGAGCCACAACAAAAACAGAGGATCAGTTCAGTGGA

TTTTTTTATTTTTATTTTTGACAAAAATAGGCTATGCACTAG.

A segment of the Gm-miRMON1A sequence (SEQ ID NO. 34), including both promoter and 5' leader nucleotides and having the sequence (SEQ ID NO. 35)
GTTAATGGTTCTGTAAATTGAAGAACAGAAACTGTGTTTCTTA

AATGTTCTTTGGAAGTTGAGGAGTTTTTAAGAGCAGCAACTGT

ACTTTCAATGGATGGCATAAACAGTCTTTACAAAAAAAGTGG

TTTGTATAACCATCAACTTAATGCATAAAAAGCTTTCCTTTGA

AGTTTATTAGCCCCAAAATATTTTGTGTACCTCAGGCACGTT

AATTTGCTTCAGTATAGTATTTGTAAACACAAACATAATTCTA

CTGAAGTCGGCTTCATATTATTTTTAAATTTTCCAATTAAAA

ATACAAAAACTGATGAATTTGAAAGAGATATATATGATATGTT

ATGATGGGGTGATCAAATCAATCGTCTGCTATGAAAGTTATA

CGTCTAATTCTTTTTTTTCTTTGTAATAAAAAATTAACTTACG

AACTAAAAGAATAAAGATTAGCAATAGTTTACAAAAGTTGAGA

```
GACTTGAATTTTTACTTTGATATAATGAAATTTTGAATAATAT

AATATGTTCGATCTTTTTTCTTTATGTAAGCATATGATTTCAT

TTCATCATTGCTTAGCACTTTTTGTATTTTTAAAAAATTCTCA

AATCATTAATTATTTTAAATTTTGTATTTTTTTTAAATCTCA

GTTACTTGCACTAAAATAATTATATGTTGGTCCCTTTTTACAT

TAAATTTCTTTTTCTTTCCCCAAACTTTAACTACTTAAATTCT

CAAATTAATTATTTTTAATAAAAAATTACTTTCTCAAATCTAA

GCTGATCCACTCTTACATTAAGAAGACACGCTATTAACTTTTC

TTTTATCAAATTAATTATACATGTCTCTTTATAAGTTTTTTTT

TTCTTTTGATATATATTTATTAAATTCTACCTGAATCAATTAT

GTATATAATGTTTATAATTTTAAATATTTTTTTTTCTTTCTA

GGTTATATTTTTTAATTTAAAATATTGACGAAGTCAACAATA

TTTGTGTTTTGCATTGACGTGCTGGCAACGGGAAGTTGTACTA

TATACATAGCGTCTTAGATTTGTGTTCAAATCGGTAGTACAA

GTACTAGTACTACATGTACATCTAACCTAGAAGAAGTACCACG

CTTGCTTGAGGCTATATATCCACTGAATCAAGTTGGATAAACA

TAAACTCATTACATTGATAAAACACAATTCAAAAGATCAATGT

TCCACTTCATGCAAAGACATTTCCAAAATATGTG
``` was used to drive GUS expression in vector pMON118505, which was used to bombard soybean leaf and root tissues.

121) Alignment of the Gm-miRMON1 sequences SEQ ID NO. 29, SEQ ID NO. 30, SEQ ID NO. 31, SEQ ID NO. 34, and SEQ ID NO. 35 yielded the consensus sequence

```
                                    (SEQ ID NO. 36)
AGCTGATCCACTCTTNCATTAAGAAGACACGCTATTAACTTTT

CTTTTATCAAATTAATTATACATGTCTCTTTATAAGTTTTTTT

TTTCTTTTGATATATATTTATTAAATTCTACCTGAATCAATTA

TGTATATAATGTTTATAATTTTAAATATTTTTTTTTCTTTCT

AGGTTATATTTTTTAATTTAAAATATTGACGAAGTCAACAAT

ATTTGTGTTTGCATTGACGTGCTGGCAACGGGAAGTTGTACT

ATATACATAGCGTCTTAGATTTGTGTTCAAATCGGTAGTACAA

AGTACTAGTACTACATGTACATCTAACCTAGAAGAAGTACCAC

GCTTGCTTGAGGCTATATATCCACTGAATCAAGTTGGATAAAC

ATA,
```

Alignment of the longer genomic Gm-miRMON1 sequences SEQ ID NO. 29 and SEQ ID NO. 34 yielded the consensus sequence

```
                                    (SEQ ID NO. 37)
AGCTGATCCACTCTTNCATTAAGAAGACACGCTATTAACTTTT

CTTTTATCAAATTAATTATACATGTCTCTTTATAAGTTTTTTT

TTTCTTTTGATATATATTTATTAAATTCTACCTGAATCAATTA

TGTATATAATGTTTATAATTTTAAATATTTTTTTTTCTTTCT

AGGTTATATTTTTTAATTTAAAATATTGACGAAGTCAACAAT

ATTTGTGTTTGCATTGACGTGCTGGCAACGGGAAGTTGTACT

ATATACATAGCGTCTTAGATTTGTGTTCAAATCGGTAGTACAA

AGTACTAGTACTACATGTACATCTAACCTAGAAGAAGTACCAC

GCTTGCTTGAGGCTATATATCCACTGAATCAAGTTGGATAAAC

ATAAACTCATTACATTGATAAAACACAATTCAAAAGATCAATG

TTCCACTTCATGCAAAGACATTTCCAAAATATGTGTAGGTAGA

GGGGTTTTACAGGATCGTCCTGAGACCAAATGAGCAGCTGACC

ACATGATGCAGCTATGTTTGCTATTCAGCTGCTCATCTGTTCT

CAGGTCGCCCTTGTTGGACTGTCCAACTCCTACTGATTGCGGA

TGCACTTGCCACAAATGAAAATCAAAGCGAGGGGAAAAGAATG

TAGAGTGTGACTACGATTGCATGCATGTGATTTAGGTAATTAA

GTTACATGATTGTCTAATTGTGTTTATGGAATTGTATATTTTC

AGACCAGGCACCTGTGACTAATTATAGGTACCATACCTTAAAA

TAAGTCCAACTAAGTCCATGTCTGTGATTTTTTAGTGTCACAA

ATCACAATCCATTGCCATTGGTTTTTTAATTTTTCATTGTCTG

TTGTTTAACTAACTCTAGCTTTTTAGCTGCTTCAAGTACAGAT

TCCTCAAAGTGGAAAATGTTCTTTGAAGTCAATAAAAAGAGCT

TTGATGATCATCTGCATTGTCTAAGTTGGATAAACTAATTAGA

GAGAACTTTTGAACTTTGTCTACCAAATATCTGTCAGTGTCAT

CTGTCAGTTCTGCAAGCTGAAGTGTTGAATCCACGAGGTGCTT

GTTGCAAAGTTGTGATATTAAAAGACATCTACGAAGAAGTTCA

AGCAAAACTCTTTTTGGCATACTTGCTGCTGCAGAAGGAACAA

CTTTACCAAAAAAATTTGTTTTAAAAAAATGCTATGATAACAA

TAATGAAGAAACTAAGCATGCAAAACTGCAAAAGTTGTGCTAT

AAAAAAAATCCAAACCAAAATGAAGGACAAAAGAATTTGAAAC

TCAATATCCTTTTACACAGATTATTTCACAAATCACAATTAAG

TAGCAACTTGCAACAGATTAAAATATATTATTTTAACAAAATA

TGAAACAAGGATATTTTCATACACAGTGAGCACAGTGAGCGTG

CTGCACTGCACTTGGAGTTGAGGAGAGTCAGTTCAGTTCAGTG

AAAGAGAAGATGGAATTTTTTGTTTGGGGAGAGCCACAACAAA

AACAGAGGATCAGTTCAGTGGATTTTTTATTTTTATTTTTG

ACAAAAATAGGCTATGCACTAG,
``` wherein N is A or G). 122) In situ hybridization experiments indicated that Gm-miRMON1A expression was highly specific to mesophyll cells. Thus, an additional aspect of this invention is a recombinant DNA construct for modulating mesophyll expression of a transgene, including: (a) a promoter of a miRNA gene encoding a mature miRNA characterized as having mesophyll-specific expression, operably linked to DNA encoding the transgene, wherein expression of the at least one transgene is mesophyll-specific; or (b) DNA encoding (i) an exogenous miRNA recognition site that is recognizable by a mature miRNA characterized as having mesophyll-specific expression, and (ii) DNA encoding the transgene, wherein expression of the transgene is decreased in mesophyll cells relative to expression in non-mesophyll cells; non-limiting examples of an exogenous miRNA recognition site that is recognizable by a mature miRNA characterized as having mesophyll-specific expression are provided in Table 2. Still further aspects of this invention are non-natural transgenic plant cells having in their genome a recombinant DNA construct of this invention for modulating mesophyll expression of a transgene, a non-natural transgenic plant containing the transgenic plant cell, a non-natural transgenic plant grown from the transgenic plant cell, and non-natural transgenic seed produced by the transgenic plants, as well as commodity products produced from non-natural transgenic plant cells, plants, or seeds of this invention.

123) Recombinant DNA constructs including the Gm-miRMON1 promoter (SEQ ID NO. 30) or the Gm-miRMON1A promoter sequences (SEQ ID NO. 31 or SEQ ID NO. 35) or the Gm-miRMON1 promoter consensus sequence (SEQ ID NO. 36) operably linked to DNA encoding at least one gene to be expressed are useful for expression of the at least one gene in a pattern similar to the substantially nocturnal expression pattern of the endogenous Gm-miRMON1 transcript. In a non-limiting example, a recombinant DNA construct, including the Gm-miRMON1 promoter (SEQ ID NO. 30) or the Gm-miRMON1A promoter sequences (SEQ ID NO. 31 or SEQ ID NO. 35) or the Gm-miRMON1 promoter consensus sequence (SEQ ID NO. 36) operably linked to a transgene transcription unit encoding green fluorescent protein (GFP), is transformed into a soybean plant; the pattern of GFP expression is observed to be preferential in leaf tissue and substantially nocturnal. In another non-limiting example, a recombinant DNA construct, including the Gm-miRMON1 promoter (SEQ ID NO. 30) or the Gm-miRMON1A promoter sequences (SEQ ID NO. 31 or SEQ ID NO. 35) or the Gm-miRMON1 promoter consensus sequence (SEQ ID NO. 36) operably linked to a gene suppression element for suppressing an endogenous soybean plant gene known to be expressed during both night and day, is transformed into a soybean plant; expression of the endogenous soybean plant gene is observed to be substantially silenced during the night.

124) Recombinant DNA constructs of this invention include those using a derivative Gm-miRMON1 promoter, such as a fragment including at least about 50, at least about 100, at least about 150, at least about 200, at least about 250, at least about 300, or at least about 350, contiguous nucleotides of SEQ ID NO. 30 or SEQ ID NO. 36, or a fragment including at least about 50, at least about 100, at least about 150, at least about 200, at least about 250, at least about 300, at least about 350, at least about 400, at least about 500, at least about 600, at least about 800, at least about 1000, or at least about 1200 contiguous nucleotides of SEQ ID NO. 31 or SEQ ID NO. 35, wherein the fragment exhibits promoter activity similar to that of the endogenous Gm-miRMON1 promoter in a plant cell. Promoter activity is routinely assayed, for example, by placing a reporter gene such as GUS or GFP under the control of the derivative promoter and observing expression of the reporter gene. Non-limiting examples include a promoter that includes a fragment of at least 100 contiguous nucleotides (for example, at least about 100, at least about 150, at least about 200, at least about 250, at least about 300, at least about 350, or at least about 400 contiguous nucleotides) having at least 85%, at least 90%, or at least 95% identity to a segment of equivalent length of SEQ ID NO. 30, SEQ ID NO. 31, SEQ ID NO. 35, or SEQ ID NO. 36 and that exhibits promoter activity similar to that of the endogenous Gm-miRMON1 promoter in a plant cell—that is to say, substantially nocturnal promoter activity and/or substantially mesohyll-specific promoter activity. Non-limiting preferred embodiments of this invention include (1) a promoter including SEQ ID NO. 30, SEQ ID NO. 31, SEQ ID NO. 35, or SEQ ID NO. 36 that exhibits substantially nocturnal promoter activity, (2) a promoter including SEQ ID NO. 30, SEQ ID NO. 31, SEQ ID NO. 35, or SEQ ID NO. 36 that exhibits substantially mesohyll-specific promoter activity, (3) a promoter including at least 100 contiguous nucleotides having at least 95% sequence identity to a fragment of at least 100 contiguous nucleotides from nucleotides 1-394 of SEQ ID NO. 30 and that exhibits substantially nocturnal promoter activity, (4) a promoter including at least 100 contiguous nucleotides having at least 95% sequence identity to a fragment of at least 100 contiguous nucleotides from nucleotides 1-394 of SEQ ID NO. 30 that exhibits substantially mesohyll-specific promoter activity, (5) a promoter including at least 100 contiguous nucleotides having at least 95% sequence identity to a fragment of at least 100 contiguous nucleotides from nucleotides 1-1298 of SEQ ID NO. 31 that exhibits substantially nocturnal promoter activity, (6) a promoter including at least 100 contiguous nucleotides having at least 95% sequence identity to a fragment of at least 100 contiguous nucleotides from nucleotides 1-1298 of SEQ ID NO. 31 that exhibits substantially mesohyll-specific promoter activity, (7) a promoter including at least 100 contiguous nucleotides having at least 95% sequence identity to a fragment of at least 100 contiguous nucleotides from nucleotides 1-1238 of SEQ ID NO. 35 that exhibits substantially nocturnal promoter activity, (8) a promoter including at least 100 contiguous nucleotides having at least 95% sequence identity to a fragment of at least 100 contiguous nucleotides from nucleotides 1-1238 of SEQ ID NO. 35 that exhibits substantially mesohyll-specific promoter activity, (9) a promoter including at least 100 contiguous nucleotides having at least 95% sequence identity to a fragment of at least 100 contiguous nucleotides from nucleotides 1-394 of SEQ ID NO. 36 and that exhibits substantially nocturnal promoter activity, and (10) a promoter including at least 100 contiguous nucleotides having at least 95% sequence identity to a fragment of at least 100 contiguous nucleotides from nucleotides 1-394 of SEQ ID NO. 36 that exhibits substantially mesohyll-specific promoter activity. Yet another aspect of this invention is a recombinant DNA construct including (a) SEQ ID NO. 30, or (b) at least 100 contiguous nucleotides having at least 95% sequence identity to a fragment of at least 100 contiguous nucleotides from nucleotides 1-394 of SEQ ID NO. 30, or (c) SEQ ID NO. 31, or (d) at least 100 contiguous nucleotides having at least 95% sequence identity to a fragment of at least 100 contiguous nucleotides from nucleotides 1-1298 of SEQ ID NO. 31, or (e) SEQ ID NO. 35, or (f) at least 100 contiguous nucleotides having at least 95% sequence identity to a fragment of at least 100 contiguous nucleotides from nucleotides 1-1238 of SEQ ID NO. 35, or (g) SEQ ID NO. 36, or (h) at least 100 contiguous nucleotides having at least 95% sequence identity to a fragment of at least 100 contiguous nucleotides from nucleotides 1-390 of SEQ ID NO. 36.

Example 5

125) In many embodiments of this invention, the recombinant DNA construct includes a gene suppression element. This example further illustrates non-limiting embodiments of gene suppression elements, which are discussed in detail in U.S. patent application Ser. No. 11/303,745, specifically incorporated by reference herein.

126) FIG. 5, Panel A schematically depicts non-limiting examples of recombinant DNA constructs that illustrate arrangement of components of the construct. In these non-limiting examples, the constructs include at least one first gene suppression element ("GSE" or "GSE1") for suppressing at least one first target gene, wherein the first gene suppression element is embedded in an intron flanked on one or on both sides by non-protein-coding DNA. These constructs utilize an intron (in many embodiments, an intron derived from a 5' untranslated region or an expression-enhancing intron is preferred) to deliver a gene suppression element without requiring the presence of any protein-coding exons (coding sequence). The constructs can optionally include at least one second gene suppression element ("GSE2") for suppressing at least one second target gene, at least one gene expression element ("GEE") for expressing at least one gene of interest (which can be coding or non-coding sequence or both), or both. In embodiments containing an optional gene expression element, the gene expression element can be located outside of (e. g., adjacent to) the intron. In some embodiments, the intron containing the first gene suppression element is 3' to a terminator.

127) To more clearly differentiate recombinant DNA constructs of the invention (containing at least one gene suppression element embedded within a single intron flanked on one or on both sides by non-protein-coding DNA) from the prior art, FIG. 5, Panel B schematically depicts examples of prior art recombinant DNA constructs. These constructs can contain a gene suppression element that is located adjacent to an intron flanked by protein-coding sequence, or between two discrete introns (wherein the gene suppression element is not embedded in either of the two discrete introns), or can include a gene expression element including a gene suppression element embedded within an intron which is flanked by multiple exons (e. g., exons including the coding sequence of a protein).

128) FIG. 6 depicts various non-limiting examples of gene suppression elements useful in the recombinant DNA constructs of the invention. Where drawn as a single strand (Panels A through E), these are conventionally depicted in 5' to 3' (left to right) transcriptional direction; the arrows indicate anti-sense sequence (arrowhead pointing to the left), or sense sequence (arrowhead pointing to the right). These gene suppression elements can include: DNA that includes at least one anti-sense DNA segment that is anti-sense to at least one segment of at least one first target gene, or DNA that includes multiple copies of at least one anti-sense DNA segment that is anti-sense to at least one segment of at least one first target gene (Panel A); DNA that includes at least one sense DNA segment that is at least one segment of at least one first target gene, or DNA that includes multiple copies of at least one sense DNA segment that is at least one segment of at least one first target gene (Panel B); DNA that transcribes to RNA for suppressing at least one first target gene by forming double-stranded RNA and includes at least one anti-sense DNA segment that is anti-sense to at least one segment of at least one first target gene and at least one sense DNA segment that is at least one segment of at least one first target gene (Panel C); DNA that transcribes to RNA for suppressing at least one first target gene by forming a single double-stranded RNA and includes multiple serial anti-sense DNA segments that are anti-sense to at least one segment of at least one first target gene and multiple serial sense DNA segments that are at least one segment of at least one first target gene (Panel D); DNA that transcribes to RNA for suppressing at least one first target gene by forming multiple double strands of RNA and includes multiple anti-sense DNA segments that are anti-sense to at least one segment of at least one first target gene and multiple sense DNA segments that are at least one segment of at least one first target gene, and wherein said multiple anti-sense DNA segments and the multiple sense DNA segments are arranged in a series of inverted repeats (Panel E); and DNA that includes nucleotides derived from a miRNA (including, but not limited to, nucleotides derived from the invertebrate mature miRNAs and miRNA precursors of this invention), or DNA that includes nucleotides of a siRNA (Panel F).

129) Panel F depicts various non-limiting arrangements of double-stranded RNA that can be transcribed from embodiments of the gene suppression elements useful in the recombinant DNA constructs of the invention. When such double-stranded RNA is formed, it can suppress one or more target genes, and can form a single double-stranded RNA or multiple double strands of RNA, or a single double-stranded RNA "stem" or multiple "stems". Where multiple double-stranded RNA "stems" are formed, they can be arranged in "hammerheads" or "cloverleaf" arrangements. In some embodiments, the double-stranded stems can form a "pseudoknot" arrangement (e. g., where spacer or loop RNA of one double-stranded stem forms part of a second double-stranded stem); see, for example, depictions of pseudoknot architectures in Staple and Butcher (2005) *PLoS Biol.*, 3(6):e213. Spacer DNA (located between or adjacent to dsRNA regions) is optional but commonly included and generally includes DNA that does not correspond to the target gene (although in some embodiments can include sense or anti-sense DNA of the target gene). Spacer DNA can include sequence that transcribes to single-stranded RNA or to at least partially double-stranded RNA (such as in a "kissing stem-loop" arrangement), or to an RNA that assumes a secondary structure or three-dimensional configuration (e. g., a large loop of antisense sequence of the target gene or an aptamer) that confers on the transcript an additional desired characteristic, such as increased stability, increased half-life in vivo, or cell or tissue specificity.

130) All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for providing temporal or leaf specific expression of a gene in a plant, comprising:
   (i) operably linking to the gene a recombinant DNA construct encoding a promoter comprising:
   a. SEQ ID NO. 31,
   b. a sequence having at least 95% sequence identity to SEQ ID NO. 31,
   c. SEQ ID NO. 35,
   d. a sequence having at least 95% sequence identity to SEQ ID NO. 35,
   e. SEQ ID NO. 36, or
   f. a sequence having at least 95% sequence identity to SEQ ID NO. 36,
      wherein the promoter exhibits temporal or leaf specific activity; and
   (ii) transforming the recombinant DNA construct in the plant.

2. The method of claim 1, wherein the gene is selected from the group consisting of a gene endogenous to the plant, a transgene in the plant, a gene conferring herbicide tolerance, a gene conferring pest resistance, a gene encoding a gene suppression element, and a gene encoding a microRNA.

3. The method of claim 2, wherein the microRNA is selected from the group consisting of miRMON1, miR393, miR159, miR390, miR156, and TAS3 5'D7(+).

4. The method of claim 2, wherein the microRNA is a mature microRNA.

5. The method of claim 2, wherein the gene suppression element comprises a sequence that is complementary to 22 contiguous nucleotides of a target RNA.

6. The method of claim 1, wherein the plant is a soybean plant.

7. A recombinant DNA construct transcribable in a plant cell for providing temporal or leaf specific expression of a gene, comprising a gene operably linked to a promoter comprising:
   a. SEQ ID NO. 31,
   b. a sequence having at least 95% sequence identity to SEQ ID NO. 31,
   c. SEQ ID NO. 35,
   d. a sequence having at least 95% sequence identity to SEQ ID NO. 35,
   e. SEQ ID NO. 36, or
   f. a sequence having at least 95% sequence identity to SEQ ID NO. 36,
      wherein the promoter exhibits temporal or leaf specific activity.

8. The recombinant DNA construct of claim 7, wherein the gene is selected from the group consisting of a gene endogenous to the plant, a transgene in the plant, a gene conferring herbicide tolerance, a gene conferring pest resistance, a gene encoding a gene suppression element, and a gene encoding a microRNA.

9. The recombinant DNA construct of claim 8, wherein the microRNA is selected from the group consisting of miRMON1, miR393, miR159, miR390, miR156, and TAS3 5'D7(+).

10. The recombinant DNA construct of claim 8, wherein the microRNA is a mature microRNA.

11. The recombinant DNA construct of claim 8, wherein the gene suppression element comprises a sequence that is complementary to 22 contiguous nucleotides of a target RNA.

12. A plant comprising in its genome the recombinant DNA construct of claim 7.

13. A seed comprising in its genome the recombinant DNA construct of claim 7.

\* \* \* \* \*

SEQUENCE LISTING

```
<160> NUMBER OF SEQ ID NOS: 37

<210> SEQ ID NO 1
<211> LENGTH: 21
<212> TYPE: RNA
<213> ORGANISM: Glycine max
```

<400> SEQUENCE: 1
ugagaccaaa ugagcagcug a                                                      21

<210> SEQ ID NO 2
<211> LENGTH: 21
<212> TYPE: RNA
<213> ORGANISM: Glycine max

<400> SEQUENCE: 2
uccaaaggga ucgcauugau c                                                      21

<210> SEQ ID NO 3
<211> LENGTH: 21
<212> TYPE: RNA
<213> ORGANISM: Glycine max

<400> SEQUENCE: 3
uuuggauuga agggagcucu a                                                      21

<210> SEQ ID NO 4
<211> LENGTH: 21
<212> TYPE: RNA
<213> ORGANISM: Glycine max

<400> SEQUENCE: 4
aagcucagga gggauagcgc c                                                      21

<210> SEQ ID NO 5
<211> LENGTH: 20
<212> TYPE: RNA
<213> ORGANISM: Glycine max

<400> SEQUENCE: 5
ugacagaaga gagugagcac                                                        20

<210> SEQ ID NO 6
<211> LENGTH: 21
<212> TYPE: RNA
<213> ORGANISM: Glycine max

<400> SEQUENCE: 6
uucuugaccu uguaaggccu u                                                      21

<210> SEQ ID NO 7
<211> LENGTH: 762
<212> TYPE: DNA
<213> ORGANISM: Glycine max

<400> SEQUENCE: 7
aaaattcatt acattgataa aacacaattc aaaagatcaa tgttccactt catgcaaaga      60
catttccaaa atatgtgtag gtagaggggt tttacaggat cgtcctgaga ccaaatgagc     120
agctgaccac atgatgcagc tatgtttgct attcagctgc tcatctgttc tcaggtcgcc     180
cttgttggac tgtccaactc ctactgattg cggatgcact tgccacaaat gaaaatcaaa     240
gcgaggggaa aagaatgtag agtgtgacta cgattgcatg catgtgattt aggtaattaa     300
gttacatgat tgtctaattg tgtttatgga attgtatatt ttcagaccag gcacctgtaa     360
ctaattatag gtaccatacc ttaaaataag tccaactaag tccatgtctg tgattttta      420 gtgtcacaaa tcacaatcca ttgccattgg tttttaatt tttcattgtc tgttgtttaa      480

-continued

| ctaactctag cttttagct gcttcaagta cagattcctc aaagtggaaa atgttctttg | 540 |
| aagtcaataa aaagagcttt gatgatcatc tgcattgtct aagttggata aactaattag | 600 |
| agagaacttt tgaactttgt ctaccaaata tctgtcagtg tcatctgtca gttctgcaag | 660 |
| ctgaagtgtt gaatccacga ggtgcttgtt gcaaagttgt gatattaaaa gacatctacg | 720 |
| aagaagttca agcaaaactc tttttggcaa aaaaaaaaaa aa | 762 |

<210> SEQ ID NO 8
<211> LENGTH: 739
<212> TYPE: DNA
<213> ORGANISM: Glycine max
<220> FEATURE:
<221> NAME/KEY: misc_feature
<222> LOCATION: (35)..(35)
<223> OTHER INFORMATION: n is a, t, g, or c

<400> SEQUENCE: 8

| gtaccccctc gagggcgcgg ccccgggggt tggtnggggg ttgttaatat aagcactagc | 60 |
| aatagctctc ttttggtatg aaagcctctc cttcaaccct caaactcaga gccatccatg | 120 |
| atccttctac tttccttcag cacaaaagcc tgcagagaga ggagagaagg gttacacaca | 180 |
| cttatatata tctatgtgaa acaccaaaga attaagaagg tgaagtttgg ttattatatt | 240 |
| ccactgcaac tggaggaggc atccaaaggg atcgcattga tcccaaattt cagatttata | 300 |
| aatttgtctt tctcttccct tgtcaatatt tgggatcatt tctcttccct tctcaatatt | 360 |
| tgggatcatg ctatcccttt ggattcctcc tttggtggct tctactgtat acaatggtta | 420 |
| attttggtgg actgcctcta attactgcat cagaaaccat cagatgttta atacccagtt | 480 |
| catggcctag aaactgcatt ctgcatatga aagagagtgg tatgattcat gtaagtccat | 540 |
| attatatatt gaccttggta ttgctctctt ggtcttacaa aaccaattta tttaatcttt | 600 |
| cctttcttct ttttatttat ttatttttatt tttattttta actgtgctag atgggattgt | 660 |
| ggtgtgattc atgtaatcaa ttcaatttca gtagtcagtg aataagact tttgttgttg | 720 |
| ccaaaaaaaa aaaaaaaaa | 739 |

<210> SEQ ID NO 9
<211> LENGTH: 2143
<212> TYPE: DNA
<213> ORGANISM: Glycine max

<400> SEQUENCE: 9

| cacaatacaa ttaagctcat catctggtcc tgaaattggt gaataaagtt gttttgtggt | 60 |
| ggatgagtac tgagtagtgg tgccttattg tgggtggaga gttccaaagg gatcgcattg | 120 |
| atctaattct tgtagatgtt tacacttgca agctttgcat gcaattcctg gattcagatg | 180 |
| tgattcagtg gttcacttat tggatcatgc gatcccttag gaactttcca tcaactctaa | 240 |
| acatcttgtt gatccatttg aggaattaat ttcataggtt catataatgg cgactgattc | 300 |
| ttctaatggt aatggacatc accaaacaac aacaaagcaa ccttctttgt cgtctacact | 360 |
| gcgcttatcc aaatttttc agtccaacat gagaatcttg gttactggag gagctggatt | 420 |
| cattgcgtct tacttagttg acagattgat ggaaaatgaa aaaatgaggt tattgctgc | 480 |
| tgacaactac ttcactggat ccaaagacaa ccttaaaaaa tggatagggg gtgaaaaatc | 540 |
| tgagcttatc gcttgcgatg actctaatat cttattccct ccacgcgttt tgtccctatg | 600 |
| atcttttgat atttcgaaca ggatttgagc ttcagtgggt tttttttttt ttacaatggc | 660 |
| aacgaattct tctaatggag caacaaagca acctcccatg ccatctccct tgcgtttttc | 720 |

```
caagttcttt cagtccaata tgagaattct ggttactgga ggagctggat ttattggctc      780
tcacctagtt gacaaattga tggaaaatga aaaaaatgag gtcattgttg ctgacaacta      840
cttcactgga tctaaagaca accttaaaag atggattggc catccaagat ttgagctaat      900
tcgtcatgat gtcacagagc aattgttgat tgaggttgat caaatctatc atcttgcatg      960
ccctgcttct ccaatcttct acaaatacaa ccctgtaaag acaataaaga caaatgtgat     1020
tggaacactg aacatgcttg ggcttgctaa gcgtgtggga gcaaggattt tgcttacatc     1080
tacttcagaa gtatatgggg accctcttgt gcatccacaa ccagaaagct attggggcaa     1140
tgtaaacccc attggagttc ggagttgtta tgatgagggc aagcgtgttg caaaaacttt     1200
gatgtttgat tatcataggc agcatggaat cgaaatacgc attgcgagaa tcttcaacac     1260
atatggacca cgcatgaata ttgatgatgg gcgtgttgtc agtaacttca ttgctcaagc     1320
aattcgtggt gaaccttga ctgtccaagt tccaggaact caaactcgca gtttctgcta     1380
tgtctctgac atggttgatg gacttatacg tctaatggaa ggggaaaaca ctggtccaat     1440
caacattggg aacccaggtg aatttacaat gattgaactt gccgagaatg tgaaagagct     1500
tatcaatcca aaagtgcaga taaatatggt tgagaacact cctgacgatc ctcgtcagag     1560
aaaaccagac attacaaaag caaggaatt gctgagatgg gaaccaaagg tcaagttgta     1620
tgatggcctt cctctcatgg aagaggattt ccgtcagagg cttggagttc caagagcaa     1680 ctaagctcct tttactcctt catttcttat catataatca taatgaatat tttgatagta     1740
acggggatgt ggatgaacct gttaagtgtt aagagatgtt ttatattgaa aattatggag     1800
aggaaggtta aacttgcagc cggcaaagcc aacttgaact tgctcttcaa attgatacaa     1860
taagattgct tctccaccca acttctattg gaaatgctgt tgttgagatg agttgaaatt     1920 atttttatt gaaatttagg tgttacaagt tctctttcga cttctttac ccattgtatg     1980 tcagggtagg tgtgtcttaa tgtgttctct gtaccgaaat acaattcaga ttgtgtttgg     2040
tgggttcata tttggattg aggaggtttg aatctcctta agaaataaag ttacgatgtt     2100
ctgatatgaa tgtgaaatag gttctacttg aaatgtgttt ctc                       2143
```

<210> SEQ ID NO 10
<211> LENGTH: 1370
<212> TYPE: DNA
<213> ORGANISM: Glycine max
<220> FEATURE:
<221> NAME/KEY: misc_feature
<222> LOCATION: (12)..(12)
<223> OTHER INFORMATION: n is a, t, g, or c

<400> SEQUENCE: 10

```
atctagtttg cnttgtgttg tgttgttagt ttgccttgga gtttcatgtt cttatccaga       60
tgatgagagc ttacagatca ggtttctagt tcctcgcgtc cggtggttat gtagatatga      120
gtctttgtga tgaggttcat ggtcttgtg ctttggtgtt tttctttatg gggtggttct       180
agctagctag ggtttgggta gtgagtgtaa taaagttgca aagtttttgg ttaggttacg      240
ttttgacctt attattatag ttcaaaggga aacattaatt aaagggggatt atgaagtgga     300 gctccttgaa gtccaattga ggatcttact gggtgaattg agctgcttag ctatggatcc      360
cacagttcta cccatcaata agtgcttttg tggtagtctt gtggcttcca tatctgggga     420
gcttcatttg cctttatagt attaaccttc tttggattga agggagctct acacccttct     480
cttcttttct ctcataataa tttaaatttg ttatagactc taaactttaa atgtttttt      540
```

```
tttaagtttt tccatttttc tcttttgcca tgatcccgtt cttgctgtgg agtaaccttg      600
tccgaggtat gtgcatgatt agatccatac ttaatttgtg tgcatcacga aggtgaggtt      660
gaaatgaact ttgcttttt tgacctttag gaaagttctt ttgttgcagt aatcaatttt      720
aattagtttt aattgacact attacttta ttgtcatctt tgttagtttt attgttgaat      780
tgagtgcata tttcctagga aattctctta cctaacattt tttatacaga tctatgctct      840
tggctcttgc ccttattctt ggccttgtgt tggttatttg tctacatatt tattgactgg      900
tcgatgagac atgtcacaat tcttgggctt atttgttggt ctaataaaag gagtgcttat      960
tgaaagatca agacggagat tcggttttat ataaataaac taagatgac atattagtgt     1020 tttgatgtct cttcaggata attttgttt gaaataatat ggtaatgtct tgtctaaatt     1080
tgtatacata attcttactg attttttgga ttgttggatt tcataaaata aatcttcaat     1140
tcgttggcaa ttgtaaaatc gtttaagttt ttttgttttt tgattgttta ttatagggtg     1200
tataggttct acaggaagga cttctgaaaa tacttaattt tctgtaagg gagattgatt     1260 tttgcgaaac attatagtcg ataggatttt tgtattccta aaattgcaga ctgggatata     1320
ttctcatgcc ctaaatcgat ttgtgaagaa tattatcgtg ttttacactc              1370

<210> SEQ ID NO 11
<211> LENGTH: 592
<212> TYPE: DNA
<213> ORGANISM: Glycine max

<400> SEQUENCE: 11
cccgcgtccg ttatgttcct aatggtagct agcttagcca gcttttttt aagaaaaggg       60 ttattagctt tgctgcacct tgtgtgtgtg ctgttgtgtt gtgctgctct tgttttttag      120
tgtggaagaa tctgtaaagc tcaggaggga tagcgccatg gatgatcttc tcttcactct      180
tgatcttctc ttgcgctatc catcctgagt ttcatggctt ctatctacac acaatggatc      240
ttcagttttc aggagaaacc ccccaaaaga aaaaaaaaa aataaaaata aaattgttgg      300
tcttaatctt catgcactac tctacactac tcaaaggttc tttcagtttt actacttctt      360
ttgtcgttct acttctttca tttttgtttg ttatgtcaat tttaatgact aacatctttt      420 ctttctttt tgttttccta agtgaaagag agagcctaaa gatgaagtaa gtggaagaaa      480
ggtagaaacc aaaatgtgtc aaatcctctt gggttgtgta gagtgactct ttatttactt      540
caaagttttc tcttttaaa gtgggtttaa aaggtggtga ctagcccaaa aa              592

<210> SEQ ID NO 12
<211> LENGTH: 690
<212> TYPE: DNA
<213> ORGANISM: Glycine max
<220> FEATURE:
<221> NAME/KEY: misc_feature
<222> LOCATION: (9)..(9)
<223> OTHER INFORMATION: n is a, t, g, or c

<400> SEQUENCE: 12
attcccggng tcgacccacg cgtccgttaa tgttccataa tggtagctag ctatagccag       60
cttttttttt ttaaagggt tattagcttt gctgcacctt cctcgtgtgt gctgttgtgc      120
tgctcttgtt tttagtgtg aagaatctg taaagctcag gagggatagc gccatggatg      180
atctcttctc cactcttgat cttctcttgc gctatccatc ctgagtttca tggcttctat      240
ccacacacaa tggaagaagc tcctctctgt ttttgcctc tatatttgcc tgaatcttga      300
cttttcagga gacacccccc aaaggaaaaa gaaattggtc tcttaatcat catgccctac      360
```

```
tctatacact agtcaagttt tgtttcccca agtgaaagag agtgcctaag gatgaagtaa      420
taagtggaag aaagtagaca ccaaaatgtg ttaagcctct tgggttgtgt agagtgattc      480
tctctttaat ttgcttcaaa gttttctctt tttaaagtgt attttaaaag ttgatgacta      540
gccaaaattt ggtatctgtt aatgtctatc taacactata tccatatatg ctacaatata      600
agttcaagta agtaaactca gaagatcaaa tgaatggttc tctttacaaa aaaaaaaaa      660 aagggcggcc gctcgcgatc tagaactagt                                      690

<210> SEQ ID NO 13
<211> LENGTH: 122
<212> TYPE: RNA
<213> ORGANISM: Glycine max

<400> SEQUENCE: 13
cacaccagau ugagagaggc ugacagaaga gagugagcac augcuagugg uauuuguaug      60
agggcauaca auugcgggug cgugcucacu ucucuaucug ucagcuuccc auucuuuuuu     120
ac                                                                   122

<210> SEQ ID NO 14
<211> LENGTH: 120
<212> TYPE: RNA
<213> ORGANISM: Glycine max

<400> SEQUENCE: 14
ugaugugaga uaucucaugu ugacagaaga gagagagcac aacccgggaa uggcuaaagg      60
agucuuugcc uuuguuggga gugugcccuc ucuuccucug ucaucaucac auucacaugc     120

<210> SEQ ID NO 15
<211> LENGTH: 185
<212> TYPE: RNA
<213> ORGANISM: Glycine max

<400> SEQUENCE: 15
acuugaccac uaggcuuauc ucuuuccguu ucugagcaug cauacucauu cacagcauca      60
aaaugcacag auccugaugg agauugcaca gggcagguga ugcuagauug caccauacuc     120
aaaucuggac uuugugauug aaguguugac agaagauaga gagcacaacc ugaucaaag     180 gaucc                                                                185

<210> SEQ ID NO 16
<211> LENGTH: 151
<212> TYPE: RNA
<213> ORGANISM: Glycine max

<400> SEQUENCE: 16
cuacuuggua auuaagguug uugacagaag auagagagca cagaugauga uaugcauauu      60
auauaauaua uagcagggaa ucaugauga auugugcauc uuacuccuuu gugcucucua     120
uacuucuguc aucaccuuca gccuccauuu c                                   151

<210> SEQ ID NO 17
<211> LENGTH: 124
<212> TYPE: RNA
<213> ORGANISM: Glycine max

<400> SEQUENCE: 17
aggagguguu ggugaugcug uugacagaag auagagagca cugaugauga aaugcaugaa      60
```

| agggaauggc aucucacucc uuugugcucu cuagucuucu gcaucaucc uucucccucc | 120 |
| ccuc | 124 |

<210> SEQ ID NO 18
<211> LENGTH: 1275
<212> TYPE: DNA
<213> ORGANISM: Glycine max

<400> SEQUENCE: 18

| aatcttacca taacaaaaag tcctctccct ctctctctct ttcacactct cactttttct | 60 |
| gtgcttctct tctctctcct ttaccctct tggaataata gagtagggag aaaaaaaagg | 120 |
| gtctcaaaga tgagaccaaa agacgggttt ttcattaaag gtccctataa gggagggttt | 180 |
| tttctcatgc atgtggctag cagcagcagc aagtgcaagg tggccatgag catgaccatg | 240 |
| gtcaacgacc ctttgaggag aattgggagg tgtgaccaaa aaaagaagc cattagtggc | 300 |
| tctgaaattg gagctgacaa ttcctgca gcaggagcag cttcttcatt ctaatctggt | 360 |
| gctatcctat ctgagctttt tactactact actacccttt ctttcttcat ctaatttcta | 420 |
| ccacactttt ctctttgttt ttcccttgga gtcttcttct tgaccttgta agaccttttc | 480 |
| ttgaccttgt aagacctcac accctatctc ttctctttgt ttttgctttt gtggaagacc | 540 |
| ctgtatcact atccactgat atagagttg atctccttct ttccccgtta ccacccaact | 600 |
| catactttcc ttccttgtct atccctcctg agctgttcca atttaattaa tttggcctac | 660 |
| catatatgat gcaacaattt aatgtaatat tatgccatac catggtatca tatggtatgg | 720 |
| tatagcttca tagaaattaa ttaaggacct taccttaacc ttagaagtta caacctctgc | 780 |
| caaatgtgtt gttagctatt tggagaccat ggcttccaag agagtacaac aattggggta | 840 |
| tattattttt atttttattg atatttttt tttatcttgg tgagaaatta atgtagttcg | 900 |
| tgcagcatca tggttggtcg tggtccttaa ggtatctgtg gtaagttgta aagagtggcc | 960 |
| atagttaata ataaatcaat gctgctagta ttcagaggaa attcaaaagc caaatctgta | 1020 |
| tcatatatat ttctgttatg gcaatcaatt tcgcttgtat cattgtgtgc agaataaaaa | 1080 |
| atttatgctg tgttgcagaa catctgtttc gttgttttat atgatgtttg gctgagaaag | 1140 |
| tgtgcaacaa ctgcatacat attcttttag atctaagcaa gagtttccct cgtgattgct | 1200 |
| ccaatgtaca aatatccact gtattattgg agttatctct tttctctctc tctctaaaaa | 1260 |
| aaaaaaaaaa aaaaa | 1275 |

<210> SEQ ID NO 19
<211> LENGTH: 22
<212> TYPE: RNA
<213> ORGANISM: Zea mays

<400> SEQUENCE: 19

| uccaaaggga ucgcauugau cu | 22 |

<210> SEQ ID NO 20
<211> LENGTH: 21
<212> TYPE: RNA
<213> ORGANISM: artificial sequence
<220> FEATURE:
<223> OTHER INFORMATION: synthetic construct

<400> SEQUENCE: 20

| ucagcugcuc aucuguucuc a | 21 |

```
<210> SEQ ID NO 21
<211> LENGTH: 21
<212> TYPE: RNA
<213> ORGANISM: artificial sequence
<220> FEATURE:
<223> OTHER INFORMATION: synthetic construct

<400> SEQUENCE: 21
ccagcugcuc auuuggucac u                                              21

<210> SEQ ID NO 22
<211> LENGTH: 21
<212> TYPE: RNA
<213> ORGANISM: artificial sequence
<220> FEATURE:
<223> OTHER INFORMATION: synthetic construct

<400> SEQUENCE: 22
ucagcucuuc uuuuggucuc u                                              21

<210> SEQ ID NO 23
<211> LENGTH: 21
<212> TYPE: RNA
<213> ORGANISM: artificial sequence
<220> FEATURE:
<223> OTHER INFORMATION: synthetic construct

<400> SEQUENCE: 23
ucagcuacug aucuggucuc a                                              21

<210> SEQ ID NO 24
<211> LENGTH: 21
<212> TYPE: RNA
<213> ORGANISM: artificial sequence
<220> FEATURE:
<223> OTHER INFORMATION: synthetic construct

<400> SEQUENCE: 24
ucagcuguuc cuuuguucuc u                                              21

<210> SEQ ID NO 25
<211> LENGTH: 21
<212> TYPE: RNA
<213> ORGANISM: artificial sequence
<220> FEATURE:
<223> OTHER INFORMATION: synthetic construct

<400> SEQUENCE: 25
ucagcuguuc cuuuguucuc u                                              21

<210> SEQ ID NO 26
<211> LENGTH: 21
<212> TYPE: RNA
<213> ORGANISM: artificial sequence
<220> FEATURE:
<223> OTHER INFORMATION: synthetic construct

<400> SEQUENCE: 26
guagcuucuc acuuggucuu a                                              21

<210> SEQ ID NO 27
<211> LENGTH: 21
<212> TYPE: RNA
<213> ORGANISM: artificial sequence
<220> FEATURE:
<223> OTHER INFORMATION: synthetic construct
```

<400> SEQUENCE: 27
uuagcugcuu cuucggucuc u                                          21

<210> SEQ ID NO 28
<211> LENGTH: 21
<212> TYPE: RNA
<213> ORGANISM: artificial sequence
<220> FEATURE:
<223> OTHER INFORMATION: synthetic construct

<400> SEQUENCE: 28
uuagaugcuu guuuggucuu u                                          21

<210> SEQ ID NO 29
<211> LENGTH: 1575
<212> TYPE: DNA
<213> ORGANISM: Glycine max

<400> SEQUENCE: 29
ctgcagctga tccactcttg cattaagaag acacgctatt aacttttctt ttatcaaatt    60
aattatacat gtctctttat aagttttttt tttcttttga tatatattta ttaaattcta   120
cctgaatcaa ttatgtatat aatgtttata atttttaaata ttttttttttt ctttctaggt  180
tatatttttt taatttaaaa tattgacgaa gtcaacaata tttgtgtttt gcattgacgt   240
gctggcaacg ggaagttgta ctatatacat agcgtcttag atttgtgttc aaatcggtag   300
tacaaagtac tagtactaca tgtacatcta acctagaaga agtaccacgc ttgcttgagg   360
ctatatatcc actgaatcaa gttggataaa cataaactca ttacattgat aaaacacaat   420
tcaaaagatc aatgttccac ttcatgcaaa gacatttcca aaatatgtgt aggtagaggg   480
gttttacagg atcgtcctga gaccaaatga gcagctgacc acatgatgca gctatgtttg   540
ctattcagct gctcatctgt tctcaggtcg cccttgttgg actgtccaac tcctactgat   600
tgcggatgca cttgccacaa atgaaaatca aagcgagggg aaaagaatgt agagtgtgac   660
tacgattgca tgcatgtgat ttaggtaatt aagttacatg attgtctaat tgtgtttatg   720
gaattgtata ttttcagacc aggcacctgt gactaattat aggtaccata ccttaaaata   780
agtccaacta agtccatgtc tgtgattttt tagtgtcaca aatcacaatc cattgccatt   840
ggttttttaa tttttcattg tctgttgttt aactaactct agcttttag ctgcttcaag    900
tacagattcc tcaaagtgga aaatgttctt tgaagtcaat aaaaagagct ttgatgatca   960
tctgcattgt ctaagttgga taaactaatt agagagaact tttgaacttt gtctaccaaa  1020
tatctgtcag tgtcatctgt cagttctgca agctgaagtg ttgaatccac gaggtgcttg  1080
ttgcaaagtt gtgatattaa aagacatcta cgaagaagtt caagcaaaac tcttttggc   1140
atacttgctg ctgcagaagg aacaacttta ccaaaaaaat ttgttttaaa aaaatgctat  1200
gataacaata atgaagaaac taagcatgca aaactgcaaa agttgtgcta taaaaaaaat  1260
ccaaaccaaa atgaaggaca aaagaatttg aaactcaata tccttttaca cagattattt  1320
cacaaatcac aattaagtag caacttgcaa cagattaaaa tatattattt taacaaaata  1380
tgaaacaagg atattttcat acacagtgag cacagtgagc gtgctgcact gcacttggag  1440
ttgaggagag tcagttcagt tcagtgaaag agaagatgga attttttgtt tggggagagc  1500
cacaacaaaa acagaggatc agttcagtgg atttttttat tttttatttt tgacaaaaat  1560
aggctatgca ctagt                                                    1575

<210> SEQ ID NO 30
<211> LENGTH: 394
<212> TYPE: DNA
<213> ORGANISM: Glycine max

<400> SEQUENCE: 30

| | | | | | | |
|---|---|---|---|---|---|---|
| ctgcagctga | tccactcttg | cattaagaag | acacgctatt | aacttttctt | ttatcaaatt | 60 |
| aattatacat | gtctctttat | aagttttttt | tttcttttga | tatatattta | ttaaattcta | 120 |
| cctgaatcaa | ttatgtatat | aatgtttata | attttaaata | ttttttttt | ctttctaggt | 180 |
| tatattttt | taatttaaaa | tattgacgaa | gtcaacaata | tttgtgtttt | gcattgacgt | 240 |
| gctggcaacg | ggaagttgta | ctatatacat | agcgtcttag | atttgtgttc | aaatcggtag | 300 |
| tacaaagtac | tagtactaca | tgtacatcta | acctagaaga | agtaccacgc | ttgcttgagg | 360 |
| ctatatatcc | actgaatcaa | gttggataaa | cata | | | 394 |

<210> SEQ ID NO 31
<211> LENGTH: 1298
<212> TYPE: DNA
<213> ORGANISM: Glycine max

<400> SEQUENCE: 31

| | | | | | | |
|---|---|---|---|---|---|---|
| cataaacatg | tgaagatcat | cagtatgtgt | caactaaatt | aaaaaaaaaa | tgaaaataga | 60 |
| gaagatgcct | ccaaaagtga | caattattgg | attaattaac | aaaaagggaa | ggtttgaaag | 120 |
| ctttgtggtt | ttgttagtta | atggttctgt | aaattgaaga | acagaaactg | tgtttcttaa | 180 |
| atgttctttg | gaagttgagg | agtttttaag | agcagcaact | gtactttcaa | tggatggcat | 240 |
| aaacagtctt | tacaaaaaaa | agtggtttgt | ataaccatca | acttaatgca | taaaaagctt | 300 |
| tcctttgaag | tttattagcc | ccaaaatatt | tttgtgtacc | tcaggcacgt | taatttgctt | 360 |
| cagtatagta | tttgtaaaca | caaacataat | tctactgaag | tcggcttcat | attattttt | 420 |
| aaattttcca | attaaaaata | caaaaactga | tgaatttgaa | agagatatat | atgatatgtt | 480 |
| atgatggggg | tgatcaaatc | aatcgtctgc | tatgaaagtt | atacgtctaa | ttcttttttt | 540 |
| tctttgtaat | aaaaaattaa | cttacgaact | aaaagaataa | agattagcaa | tagtttacaa | 600 |
| aagttgagag | acttgaattt | ttactttgat | ataatgaaat | tttgaataat | ataatatgtt | 660 |
| cgatctttt | tctttatgta | agcatatgat | ttcatttcat | cattgcttag | cactttttgt | 720 |
| attttaaaa | aattctcaaa | tcattaatta | ttttaaattt | tgtattttt | tttaaatctc | 780 |
| agttacttgc | actaaaataa | ttatatgttg | gtcccttttt | acattaaatt | tcttttttctt | 840 |
| tccccaaact | ttaactactt | aaattctcaa | attaattatt | tttaataaaa | aattactttc | 900 |
| tcaaatctaa | gctgatccac | tcttacatta | agaagacacg | ctattaactt | ttcttttatc | 960 |
| aaattaatta | tacatgtctc | tttataagtt | tttttttct | tttgatatat | atttattaaa | 1020 |
| ttctacctga | atcaattatg | tatataatgt | ttataatttt | aaatattttt | tttttctttc | 1080 |
| taggttatat | tttttaatt | taaaatattg | acgaagtcaa | caatatttgt | gttttgcatt | 1140 |
| gacgtgctgg | caacgggaag | ttgtactata | tacatagcgt | cttagatttg | tgttcaaatc | 1200 |
| ggtagtacaa | agtactagta | ctacatgtac | atctaaccta | gaagaagtac | cacgcttgct | 1260 |
| tgaggctata | tatccactga | atcaagttgg | ataaacat | | | 1298 |

<210> SEQ ID NO 32
<211> LENGTH: 76
<212> TYPE: DNA
<213> ORGANISM: Glycine max

<400> SEQUENCE: 32

```
aaactcatta cattgataaa acacaattca aaagatcaat gttccacttc atgcaaagac    60
atttccaaaa tatgtg                                                   76
```

<210> SEQ ID NO 33
<211> LENGTH: 1105
<212> TYPE: DNA
<213> ORGANISM: Glycine max

<400> SEQUENCE: 33

```
taggtagagg ggttttacag gatcgtcctg agaccaaatg agcagctgac cacatgatgc    60
agctatgttt gctattcagc tgctcatctg ttctcaggtc gcccttgttg gactgtccaa   120
ctcctactga ttgcggatgc acttgccaca aatgaaaatc aaagcgaggg gaaaagaatg   180
tagagtgtga ctacgattgc atgcatgtga tttaggtaat taagttacat gattgtctaa   240
ttgtgtttat ggaattgtat attttcagac caggcacctg tgactaatta taggtaccat   300
accttaaaat aagtccaact aagtccatgt ctgtgatttt ttagtgtcac aaatcacaat   360
ccattgccat tggttttttta attttcatt gtctgttgtt taactaactc tagcttttta   420
gctgcttcaa gtacagattc ctcaaagtgg aaaatgttct ttgaagtcaa taaaaagagc   480
tttgatgatc atctgcattg tctaagttgg ataaactaat tagagagaac ttttgaactt   540
tgtctaccaa atatctgtca gtgtcatctg tcagttctgc aagctgaagt gttgaatcca   600
cgaggtgctt gttgcaaagt tgtgatatta aagacatct acgaagaagt tcaagcaaaa   660
ctcttttttgg catacttgct gctgcagaag gaacaacttt accaaaaaaa tttgttttaa   720
aaaaatgcta tgataacaat aatgaagaaa ctaagcatgc aaaactgcaa agttgtgct   780
ataaaaaaaa tccaaaccaa aatgaaggac aaaagaattt gaaactcaat atccttttac   840
acagattatt tcacaaatca caattaagta gcaacttgca acagattaaa atatattatt   900
ttaacaaaat atgaaacaag gatattttca tacacagtga gcacagtgag cgtgctgcac   960
tgcacttgga gttgaggaga gtcagttcag ttcagtgaaa gagaagatgg aattttttgt  1020
ttggggagag ccacaacaaa aacagaggat cagttcagtg gatttttta ttttttattt  1080
ttgacaaaaa taggctatgc actag                                        1105
```

<210> SEQ ID NO 34
<211> LENGTH: 2479
<212> TYPE: DNA
<213> ORGANISM: Glycine max

<400> SEQUENCE: 34

```
cataaacatg tgaagatcat cagtatgtgt caactaaatt aaaaaaaaaa tgaaaataga    60
gaagatgcct ccaaaagtga caattattgg attaattaac aaaaagggaa ggtttgaaag   120
ctttgtggtt tgttagtta atggttctgt aaattgaaga acagaaactg tgtttcttaa   180
atgttctttg gaagttgagg agttttttaag agcagcaact gtactttcaa tggatggcat   240
aaacagtctt tacaaaaaaa agtggtttgt ataaccatca acttaatgca taaaaagctt   300
tcctttgaag tttattagcc ccaaaatatt tttgtgtacc tcaggcacgt taatttgctt   360
cagtatagta tttgtaaaca caaacataat tctactgaag tcggcttcat attattttt   420
aaattttcca attaaaaata caaaaactga tgaatttgaa agagatatat atgatatgtt   480
atgatggggg tgatcaaatc aatcgtctgc tatgaaagtt atacgtctaa ttctttttt   540
tctttgtaat aaaaaattaa cttacgaact aaaagaataa agattagcaa tagtttacaa   600
```

```
aagttgagag acttgaattt ttactttgat ataatgaaat tttgaataat ataatatgtt    660 cgatctttt tctttatgta agcatatgat ttcatttcat cattgcttag cactttttgt     720 attttaaaa aattctcaaa tcattaatta ttttaaattt tgtattttt tttaaatctc      780 agttacttgc actaaaataa ttatatgttg gtccctttt acattaaatt tcttttctt     840 tccccaaact ttaactactt aaattctcaa attaattatt tttaataaaa aattactttc    900
tcaaatctaa gctgatccac tcttacatta agaagacacg ctattaactt ttcttttatc    960
aaattaatta tacatgtctc tttataagtt ttttttttct tttgatatat atttattaaa   1020
ttctacctga atcaattatg tatataatgt ttataattt aaatatttt tttttctttc     1080 taggttatat ttttttaatt taaaatattg acgaagtcaa caatatttgt gttttgcatt   1140
gacgtgctgg caacgggaag ttgtactata tacatagcgt cttagatttg tgttcaaatc   1200
ggtagtacaa agtactagta ctacatgtac atctaaccta gaagaagtac cacgcttgct   1260
tgaggctata tatccactga atcaagttgg ataaacataa actcattaca ttgataaaac   1320
acaattcaaa agatcaatgt tccacttcat gcaaagacat ttccaaaata tgtgtaggta   1380 gagggttt acaggatcgt cctgagacca aatgagcagc tgaccacatg atgcagctat    1440
gtttgctatt cagctgctca tctgttctca ggtcgccctt gttggactgt ccaactccta   1500
ctgattgcgg atgcacttgc cacaaatgaa aatcaaagcg aggggaaaag aatgtagagt   1560
gtgactacga ttgcatgcat gtgatttagg taattaagtt acatgattgt ctaattgtgt   1620
ttatggaatt gtatatttc agaccaggca cctgtgacta attataggta ccatacctta   1680
aaataagtcc aactaagtcc atgtctgtga tttttagtg tcacaaatca caatccattg    1740
ccattggttt tttaattttt cattgtctgt tgtttaacta actctagctt tttagctgct   1800
tcaagtacag attcctcaaa gtggaaaatg ttctttgaag tcaataaaaa gagctttgat   1860
gatcatctgc attgtctaag ttggataaac taattagaga gaactttga actttgtcta    1920 ccaaatatct gtcagtgtca tctgtcagtt ctgcaagctg aagtgttgaa tccacgaggt   1980
gcttgttgca aagttgtgat attaaaagac atctacgaag aagttcaagc aaaactcttt   2040
ttggcatact tgctgctgca gaaggaacaa ctttaccaaa aaaattgtt ttaaaaaaat    2100 gctatgataa caataatgaa gaaactaagc atgcaaaact gcaaagttg tgctataaaa    2160 aaaatccaaa ccaaaatgaa ggacaaaaga atttgaaact caatatcctt ttacacagat   2220 tattcacaa atcacaatta agtagcaact tgcaacagat taaaatatat tatttaaca    2280 aaaatatgaaa caaggatatt ttcatacaca gtgagcacag tgagcgtgct gcactgcact   2340
tggagttgag gagagtcagt tcagttcagt gaaagagaag atggaatttt tgtttgggg    2400 agagccacaa caaaaacaga ggatcagttc agtggatttt tttattttt attttgaca    2460 aaaataggct atgcactag                                                2479
```

<210> SEQ ID NO 35
<211> LENGTH: 1238
<212> TYPE: DNA
<213> ORGANISM: Glycine max

<400> SEQUENCE: 35

```
gttaatggtt ctgtaaattg aagaacagaa actgtgtttc ttaaatgttc tttggaagtt     60
gaggagtttt taagagcagc aactgtactt tcaatggatg gcataaacag tctttacaaa   120 aaaagtggt ttgtataacc atcaacttaa tgcataaaaa gctttccttt gaagtttatt    180
```

| | |
|---|---|
| agccccaaaa tattttgtg tacctcaggc acgttaattt gcttcagtat agtatttgta | 240 |
| aacacaaaca taattctact gaagtcggct tcatattatt ttttaaattt tccaattaaa | 300 |
| aatacaaaaa ctgatgaatt tgaaagagat atatatgata tgttatgatg ggggtgatca | 360 |
| aatcaatcgt ctgctatgaa agttatacgt ctaattcttt ttttctttg taataaaaaa | 420 |
| ttaacttacg aactaaaaga ataaagatta gcaatagttt acaaaagttg agagacttga | 480 |
| attttactt tgatataatg aaattttgaa taatataata tgttcgatct ttttctttta | 540 |
| tgtaagcata tgatttcatt tcatcattgc ttagcacttt ttgtattttt aaaaaattct | 600 |
| caaatcatta attattttaa attttgtatt ttttttaaa tctcagttac ttgcactaaa | 660 |
| ataattatat gttggtccct ttttacatta aatttctttt tctttcccca aactttaact | 720 |
| acttaaattc tcaaattaat tatttttaat aaaaaattac tttctcaaat ctaagctgat | 780 |
| ccactcttac attaagaaga cacgctatta acttttcttt tatcaaatta attatacatg | 840 |
| tctctttata agttttttt ttcttttgat atatatttat taaattctac ctgaatcaat | 900 |
| tatgtatata atgtttataa ttttaaatat ttttttttc tttctaggtt atattttttt | 960 |
| aatttaaaat attgacgaag tcaacaatat ttgtgttttg cattgacgtg ctggcaacgg | 1020 |
| gaagttgtac tatatacata gcgtcttaga tttgtgttca aatcggtagt acaaagtact | 1080 |
| agtactacat gtacatctaa cctagaagaa gtaccacgct tgcttgaggc tatatatcca | 1140 |
| ctgaatcaag ttggataaac ataaactcat tacattgata aaacacaatt caaagatca | 1200 |
| atgttccact tcatgcaaag acatttccaa aatatgtg | 1238 |

<210> SEQ ID NO 36
<211> LENGTH: 390
<212> TYPE: DNA
<213> ORGANISM: Glycine max
<220> FEATURE:
<221> NAME/KEY: misc_feature
<222> LOCATION: (16)..(16)
<223> OTHER INFORMATION: n is a, t, g, or c

<400> SEQUENCE: 36

| | |
|---|---|
| agctgatcca ctcttncatt aagaagacac gctattaact tttctttat caaattaatt | 60 |
| atacatgtct ctttataagt ttttttttc ttttgatata tatttattaa attctacctg | 120 |
| aatcaattat gtatataatg tttataattt taaatatttt ttttttcttt ctaggttata | 180 |
| ttttttaat ttaaaatatt gacgaagtca acaatatttg tgttttgcat tgacgtgctg | 240 |
| gcaacgggaa gttgtactat atacatagcg tcttagattt gtgttcaaat cggtagtaca | 300 |
| aagtactagt actacatgta catctaacct agaagaagta ccacgcttgc ttgaggctat | 360 |
| atatccactg aatcaagttg gataaacata | 390 |

<210> SEQ ID NO 37
<211> LENGTH: 1570
<212> TYPE: DNA
<213> ORGANISM: Glycine max
<220> FEATURE:
<221> NAME/KEY: misc_feature
<222> LOCATION: (16)..(16)
<223> OTHER INFORMATION: n is a, t, g, or c

<400> SEQUENCE: 37

| | |
|---|---|
| agctgatcca ctcttncatt aagaagacac gctattaact tttctttat caaattaatt | 60 |
| atacatgtct ctttataagt ttttttttc ttttgatata tatttattaa attctacctg | 120 |
| aatcaattat gtatataatg tttataattt taaatatttt ttttttcttt ctaggttata | 180 |

-continued

```
ttttttttaat ttaaaatatt gacgaagtca acaatatttg tgttttgcat tgacgtgctg      240
gcaacgggaa gttgtactat atacatagcg tcttagattt gtgttcaaat cggtagtaca      300
aagtactagt actacatgta catctaacct agaagaagta ccacgcttgc ttgaggctat      360
atatccactg aatcaagttg gataaacata aactcattac attgataaaa cacaattcaa      420
aagatcaatg ttccacttca tgcaaagaca tttccaaaat atgtgtaggt agagggttt       480 tacaggatcg tcctgagacc aaatgagcag ctgaccacat gatgcagcta tgtttgctat      540
tcagctgctc atctgttctc aggtcgccct tgttggactg tccaactcct actgattgcg     600
gatgcacttg ccacaaatga aaatcaaagc gaggggaaaa gaatgtagag tgtgactacg     660
attgcatgca tgtgatttag gtaattaagt tacatgattg tctaattgtg tttatggaat    720
tgtatatttt cagaccaggc acctgtgact aattataggt accataccttc aaaataagtc   780 caactaagtc catgtctgtg atttttagt gtcacaaatc acaatccatt gccattggtt     840
ttttaatttt tcattgtctg ttgtttaact aactctagct ttttagctgc ttcaagtaca    900
gattcctcaa agtggaaaat gttctttgaa gtcaataaaa agagctttga tgatcatctg   960
cattgtctaa gttggataaa ctaattagag agaacttttg aactttgtct accaaatatc   1020
tgtcagtgtc atctgtcagt tctgcaagct gaagtgttga atccacgagg tgcttgttgc   1080
aaagttgtga tattaaaaga catctacgaa gaagttcaag caaaactctt tttggcatac   1140
ttgctgctgc agaaggaaca actttaccaa aaaaatttgt tttaaaaaaa tgctatgata  1200
acaataatga agaaactaag catgcaaaac tgcaaaagtt gtgctataaa aaaaatccaa   1260
accaaaatga aggacaaaag aatttgaaac tcaatatcct tttacacaga ttatttcaca   1320
aatcacaatt aagtagcaac ttgcaacaga ttaaaatata ttattttaac aaaatatgaa   1380
acaaggatat tttcatacac agtgagcaca gtgagcgtgc tgcactgcac ttggagttga   1440
ggagagtcag ttcagttcag tgaaagagaa gatggaattt tttgtttggg gagagccaca   1500
acaaaaacag aggatcagtt cagtggattt ttttattttt tattttttgac aaaaataggc   1560 tatgcactag                                                           1570
```